US007557244B2

(12) United States Patent
Wilson et al.

(10) Patent No.: US 7,557,244 B2
(45) Date of Patent: Jul. 7, 2009

(54) SUBSTITUTED BIPHENYL CARBOXYLIC ACIDS AND DERIVATIVES THEREOF

(75) Inventors: Francis Wilson, Hertz (GB); Alison Reid, Cottenham (GB); Valerie Reader, Linton (GB); Richard John Harrison, Saffron Walden (GB); Mihiro Sunose, Pampisford (GB); Remedios Hernadez-Perni, Stalybridge (GB); Jeremy Major, Cambridge (GB); Cyrille Boussard, Saffron Walden (GB); Kathryn Smelt, London (GB); Jess Taylor, Hitchin (GB); Adeline LeFormal, Saffron Walden (GB); Andrew Cansfield, Harston (GB); Svenja Burckhardt, Boxworth (GB); Chih Yung Ho, Lansdale, PA (US); Yan Zhang, Fort Washington, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 139 days.

(21) Appl. No.: 11/737,938

(22) Filed: Apr. 20, 2007

(65) Prior Publication Data

US 2007/0293567 A1 Dec. 20, 2007

(30) Foreign Application Priority Data

Apr. 21, 2006 (EP) .................................. 06112938

(51) Int. Cl.
*C07C 321/00* (2006.01)
*C07C 229/00* (2006.01)
*C07C 59/00* (2006.01)
*C07D 249/08* (2006.01)
*A01N 43/64* (2006.01)
*A01N 37/10* (2006.01)

(52) U.S. Cl. ...................... 562/457; 562/471; 562/431; 548/265.8; 514/381; 514/532

(58) Field of Classification Search ...................... None
See application file for complete search history.

(56) References Cited

U.S. PATENT DOCUMENTS 5,877,399 A 3/1999 Hsiao et al.
2002/0128319 A1 9/2002 Koo et al.

FOREIGN PATENT DOCUMENTS

| WO | WO 01/78721 | 10/2001 |
| WO | 03/008635 A2 | 1/2003 |
| WO | WO 05/110963 A | 11/2005 |
| WO | 2007039736 | * 4/2007 |
| WO | WO 07/039736 A1 | 4/2007 |

OTHER PUBLICATIONS

Kobrina et al., Journal of Fluorine Chemistry (1993), 62(2-3), 243-58.*

Nesmejanow, E. et al. "Immediate Cyanization of Ferricinium Salts", Department of Organic Chemistry of the Moscow State University, Jul. 11, 1960 (translation of document forwarded with IDS of Jun. 12, 2008.

Buchwald, H. et al. "Long-Term, Continuous Intravenous Heparin Administration by an Implantable Infusion Pump in Ambulatory Patients with Recurrent Venous Thrombosis", Surgery 88, p. 507 (1980).

During, M. et al. "Controlled Release of Dopamine from a Polymeric Brain Implant: In Vivo Characterization", Ann. Neurol. 25, p. 351 (1989).

Eriksen, et al. "NSAIDs and Enantiomers of Flurbiprofen Target Gamma-Secretase and Lower A-beta-42 in vivo" Journal of Clinical Investigation, New York, NY US, vol. 112, No. 3, Aug. 2003 pp. 440-449 XP002311406.

Evans, D., et al. "Synthesis of Diaryl Ethers through the Copper-Promoted Arylation of Phenols with Arylboronic Acids. An Expedient Synthesis of Thyronixe", Tetrahedron Letters, 39(19), p. 2937 (1990).

Frautschy, S., et al. "Microglial Response to Amyloid Plaques in APPsw Transgenic Mice", Am. J. of Pathology, VI. 52, No. I, p. 307 (1998).

Frlan, R., et al. "Recent Progress in Diaryl Ether Synthesis", Synthesis, No. 14, p. 2271 (2006).

Goodson, In: Medical Applications of Controlled Release, vol. 2 (1984) (Book).

Hartwig, I.F., Modern Arene Chemistry p. 107 (2005).

Hosseinzadeh, R., et al. Copper-Catalyzed Etherification of Aryl Iodides Using KF/A12)3, 1101 (2005).

Howard, M. et al. "Acute Subdural Hematomas: An Age-Dependent Clinical Entity", J. Neurosurgery. vol. 71, p. 858 (1989).

Hsiako, K., et al. "Correlative Memory Deficits, Aβ Elevation and Amyloid Plaques in Transgenic Mice", Science 274, p. 99 (1996).

IDA, et al. "Analysis of Heterogeneous βA4 Peptides in Human Cerebrospinal Fluid and Blood by a Newly Developed Sensitive Western Blot Assay", J. Biol. Chem. 271, p. 22908 (1996).

Irizarry, M., et al. "APP$_{AW}$ Transgenic Mice Develop Age-Related Aβ Deposits and Neuropil Abnormalities, but no Neuronal Loss in CA1", J. of Neuropathology and Experimental Neurology, vol. 56(9), p. 965 (1997).

Jensen, M. et al. "Quantification of Alzheimer Amyloid β Peptides Ending at Residues 40 and 42 by Novel ELISA Systems", Mol. Med. 6 p. 291 (2000).

Kawarabayahsim T. T. "Age-Dependent Changes in Brain, CSF, and Plasma Amyloid β Protein in the Tg2576 Transgenic Mouse Model of Alzheimer's Disease", J. Neurosci. 21 p. 372 (2001).

Langer, R. "New Methods of Drug Delivery", Science 249 p. 1527 (1990).

(Continued)

*Primary Examiner*—Karl J Puttlitz

(57) ABSTRACT

The present invention relates to compounds having the general Formula (I) with the definitions of X, Y, $R_1$, $R_2$, $R_3$, $R_4$, $R_9$, and $R_{10}$ given below, and/or a salt or ester thereof. Furthermore the invention relates to the use of said compounds for the treatment of Alzheimer's disease and their use for the modulation of γ-secretase activity.

15 Claims, No Drawings

OTHER PUBLICATIONS

Larner, A. "Secretases as Therapeutic Targets in Alzheimer's Disease: Patents 2000-2004", Expert Opin. Ther. Patents 14, p. 1403 (2004).

Lehman, J. H. et al. "Alterations in β-Amylid Production and Deposition and Brain Regions of Two Trangenic Models", Neurobiol. Aging 24, p. 645 (2003).

Levy, R., et al., "Inhibition of Calcification of Bioprostethetic Heart Valves by Local Controlled-Releas Diphosphonate", Science 228 p. 190 (1985) LIM, G. et al. "Ibuprofen Effects on Alzheimer Pathology and Open Field Activity in APPsw Transenic Mice", Neuribiol. Aging 22 p. 645 (2001).

Lim, G. et al. "Ibuprofen Effects on Alzheimer Pathology and Open Field Activity in APPsw Transonic Mice", Neuribiol. Aging 22 p. 645 (2001).

Lim, G. et al. J. "Ibuprofen Suppresses Plaque Pathology and Inflammation in a Mouse Model for Alzheimer' Disease", Neursci. 20. p. 5709 (2000).

Marjaux, E., et al. γ-Secetase Inhibitors: Still in the Running as Alheimer's Therapeutics, Drug Discovery Today: Therapeutics Strategies 1, p. 1 (2004).

Martin, E.W., Remington's Pharmaceutical Sciences (BOOK).

Moechars, D. et al. "Early Phenotypic Changes in Transgenic Mice That Overexpress Different Mutants of Amyloid Precursor Protein in Brain", J. Bil. Chem. 274, p. 6483 (1999).

Morihara, T. et al. "Selective Inhibition of Aβ42 Production b NSAID R-Enantiomer" .J. Neurochem 83, p. 1009 (2002).

Nesmejanow, E. et al. "Unmittelbare Cyanierung der Ferriciniumsalze", (Translation Will Follow).

Peretto, D., et al. "Synthesis and Biological Activity of Flurbiprofen Analogues as Selective Inhibitors of β-Amylid 1-42 Secretion"J. Med. Chem. 48 p. 5705 (2005).

Ranger, R., et al. "Chemical and Physical Structure of Polymers as Carriers for Controlled Release of Bioactive Agents: A Review", Macrombl Sci. Rev. Macromonl. Chem 23 p. 61 (1983).

Saudek, C., et al. "A Preliminary Trial of the Programmable Implantable Medication System for Insulin Delivery", K, et al. N. Engl. J. MEd. 321p. 574 (1989).

Schweisguth, F, "Regulation of Notch Signaling Activity", Curr. Biol. 14, p. R129 (2004).

Sefton, M. "Implantable Pumps", CRC Crit. Ref. Biomed. Eng. 14, p. 201 (1987).

Shimizu, K., et al. "Binding of Dentall1, Jagged1, and Jagged2 to Notch2 Rapidly Induces Cleavage, Nuclear Translocation, and Hyperphosphorylation of Notch2", Mol. Cell. Biol. 20, p. 6913 (2000).

Steiner, H. "Uncovering γ-Sucretase", Curr. Alzheimer Research 1(3), p. 175 (2004).

Tamura, V., "Nonsteroidal Anti-inflammatory Agents, 1,5-Alkoxy-3—biphenyllacetic Acids and Related Compounds New Potential Anti-inflammatory Agents", J. of Medicinal Chemistry, vol. 20, No. 5 (1977).

Tanzi, R. et al. "Twenty Years of the Alzheimer's Disease Amyloid Hypothesis: A Genetic Perspective" Cell 120, p. 545 (2005).

Thompson, A., et al. "Conversion of Phenols to the Corresponding Aryl Halies Under Mild Conditions", Synthesis, p. 547 (2005).

Vassar, R., et al. "β-Secretase Cleavageof Alzheimer's Amyloid Precursor Protein by the Transmembrane Aspartic Protese BACE", Science 286, p. 735 (199).

Wang, R. et al. "The Profile of Soluble Amyloid β Protein in Cultured Cell Media", J. Biol. Chem. 271 p. 31894 (1996).

Weggen, S., et al. "A subset of NSAIDs Lower Amylidogenic Aβ42 Independently of Cyclooxygenase Activity", Nature 414, p. 212 (2001).

Yan R., et al. "Membrane-Anchored Aspartyl Protease with Alzheimer's Disease β-Secretase Activity", Nature 402, p. 533 (1999).

Yan, Correction. J. Neurosci. 23, p. 7504 (2003).

Xia, W., et al. "Preselin 1 Regulates the Processing of β-Amyloid Precursor Protein C-Terminal Fragments and the Generation of Amyloid β-Protein in Endoplasmic Reticulum and Golgi", Biochemistry 3 . 16465 (1998).

\* cited by examiner

SUBSTITUTED BIPHENYL CARBOXYLIC ACIDS AND DERIVATIVES THEREOF

CROSS REFERENCE TO RELATED APPLICATIONS

This application claims priority of the benefits of the filing of EPO Application Serial No. 06112938.3, filed Apr. 21, 2006. The complete disclosures of the aforementioned related European patent application are hereby incorporated herein by reference for all purposes.

The present invention relates to compounds having the general formula (I) with the definitions of A, X, $R_1$-$R_4$ given below, and/or a salt or ester thereof.

Furthermore, the invention relates to the use of said compounds for the treatment of Alzheimer's disease and their use for the modulation of γ-secretase activity.

Alzheimer's Disease (AD) is a progressive neurodegenerative disorder marked by loss of memory, cognition, and behavioral stability. AD afflicts 6-10% of the population over age 65 and up to 50% over age 85. It is the leading cause of dementia and the third leading cause of death after cardiovascular disease and cancer. There is currently no effective treatment for AD. The total net cost related to AD in the U.S. exceeds $100 billion annually.

AD does not have a simple etiology, however, it has been associated with certain risk factors including (1) age, (2) family history (3) and head trauma; other factors include environmental toxins and low level of education. Specific neuropathological lesions in the limbic and cerebral cortices include intracellular neurofibrillary tangles consisting of hyperphosphorylated tau protein and the extracellular deposition of fibrillar aggregates of amyloid beta peptides (amyloid plaques). The major component of amyloid plaques are the amyloid beta (A-beta, Abeta or Aβ) peptides of various lengths. A variant thereof, which is the Aβ1-42-peptide (Abeta-42), is believed to be the major causative agent for amyloid formation. Another variant is the Aβ1-40-peptide (Abeta-40). Amyloid beta is the proteolytic product of a precursor protein, beta amyloid precursor protein (beta-APP or APP).

Familial, early onset autosomal dominant forms of AD have been linked to missense mutations in the β-amyloid precursor protein (β-APP or APP) and in the presenilin proteins 1 and 2. In some patients, late onset forms of AD have been correlated with a specific allele of the apolipoprotein E (ApoE) gene, and, more recently, the finding of a mutation in alpha2-macroglobulin, which may be linked to at least 30% of the AD population. Despite this heterogeneity, all forms of AD exhibit similar pathological findings. Genetic analysis has provided the best clues for a logical therapeutic approach to AD. All mutations, found to date, affect the quantitative or qualitative production of the amyloidogenic peptides known as Abeta-peptides (Aβ), specifically Aβ42, and have given strong support to the "amyloid cascade hypothesis" of AD (Tanzi and Bertram, 2005, Cell 120, 545). The likely link between Aβ peptide generation and AD pathology emphasizes the need for a better understanding of the mechanisms of Aβ production and strongly warrants a therapeutic approach at modulating Aβ levels.

The release of Aβ peptides is modulated by at least two proteolytic activities referred to as β- and γ-secretase cleaving at the N-terminus (Met-Asp bond) and the C-terminus (residues 37-42) of the Aβ peptide, respectively. In the secretory pathway, there is evidence that β-secretase cleaves first, leading to the secretion of s-APPβ (sβ) and the retention of a 11 kDa membrane-bound carboxy terminal fragment (CTF). The latter is believed to give rise to Aβ peptides following cleavage by γ-secretase. The amount of the longer isoform, Aβ42, is selectively increased in patients carrying certain mutations in a particular protein (presenilin), and these mutations have been correlated with early-onset familial Alzheimer's disease. Therefore, Aβ42 is believed by many researchers to be the main culprit of the pathogenesis of Alzheimer's disease.

It has now become clear that the γ-secretase activity cannot be ascribed to a single particular protein, but is in fact associated with an assembly of different proteins. The gamma-secretase activity resides within a multiprotein complex containing at least four components: the presenilin (PS) heterodimer, nicastrin, aph-1 and pen-2. The PS heterodimer consists of the amino- and carboxyterminal PS fragments generated by endoproteolysis of the precursor protein. The two aspartates of the catalytic site are at the interface of this heterodimer. It has recently been suggested that nicastrin serves as a gamma-secretase-substrate receptor. The functions of the other members of gamma-secretase are unknown, but they are all required for activity (Steiner, 2004. Curr. Alzheimer Research 1(3): 175-181).

Thus, although the molecular mechanism of the second cleavage-step has remained elusive until present, the γ-secretase-complex has become one of the prime targets in the search for compounds for the treatment of Alzheimer's disease.

Various strategies have been proposed for targeting gamma-secretase in Alzheimer's disease, ranging from targeting the catalytic site directly, developing substrate-specific inhibitors and modulators of gamma-secretase activity (Marjaux et al., 2004. Drug Discovery Today Therapeutic Strategies, Volume 1, 1-6). Accordingly, a variety of compounds were described that have secretases as targets (Lamer, 2004. Secretases as therapeutics targets in Alzheimer's disease: patents 2000-2004. Expert Opin. Ther. Patents 14, 1403-1420.)

Indeed, this finding was recently supported by biochemical studies in which an effect of certain NSAIDs on γ-secretase was shown (Weggen et al (2001) Nature 414, 6860, 212 and WO 01/78721 and US 2002/0128319; Morihara et al (2002) J. Neurochem. 83, 1009; Eriksen (2003) J. Clin. Invest. 112, 440). Potential limitations for the use of NSAIDs to prevent or treat AD are their inhibition activity of Cox enzymes, which can lead to unwanted side effects, and their low CNS penetration (Peretto et al., 2005, J. Med. Chem. 48, 5705-5720).

Thus, there is a strong need for novel compounds which modulate γ-secretase activity thereby opening new avenues for the treatment of Alzheimer's disease.

The object of the present invention is to provide such compounds.

The object is achieved by a compound having the general Formula (I)

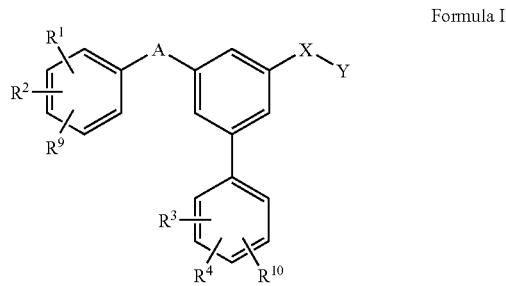

Formula I wherein

A is O, S or NH,

X is a bond or a group —$CR_5R_6$ wherein $R_5$ and $R_6$ are independently, selected from the group consisting of H, alkyl selected from the group $CH_3$, $C_2H_5$, i-$C_3H_7$, n-$C_3H_7$, i-C$_4$H$_9$, n-C$_4$H$_9$, sec-C$_4$H$_9$, tert-C$_4$H$_9$; alkenyl selected from C$_2$H$_3$, i-C$_3$H$_5$, n-C$_3$H$_5$, n-C$_4$H$_7$, i-C$_4$H$_7$, sec-C$_4$H$_7$; wherein in any of the alkyl or alkenyl groups one or more H atoms optionally can be substituted with one or more substituents independently selected from the group consisting of OH, F, Cl, Br, I and CF$_3$; or R$_5$, R$_6$ may jointly form together with the carbon atom to which they are attached a ring, either saturated or unsaturated, substituted or unsubstituted, having 3 to 6 C-atoms, and which may contain in the ring one or more heteroatoms from the group N, S or O, and which heteroatom may be identical or different if more than one heteroatom is present;

R$_1$, R$_2$, R$_3$ and R$_4$ are independently selected from the group consisting of H; F; Cl; Br; I; CN; OH; C(O)N(R$_7$R$_8$); S(O)$_2$R$_7$; SO$_2$N(R$_7$R$_8$); S(O)N(R$_7$R$_8$); N(R$_7$)S(O)$_2$R$_8$; N(R$_8$)S(O)R$_8$; S(O)$_2$R$_7$; N(R$_7$)S(O)$_2$N(R$_8$R$_{8a}$); SR$_7$; N(R$_7$R$_8$); N(R$_7$)C(O)R$_8$; N(R$_7$)C(O)N(R$_8$R$_{8a}$); N(R$_7$)C(O)OR$_8$; OC(O)N(R$_7$R$_8$); C(O)R$_7$; substituted and unsubstituted C$_1$-C$_4$-alkyl and substituted and unsubstituted C$_1$-C$_4$-alkoxy, and wherein the substituents of both groups C$_1$-C$_4$-alkyl and C$_1$-C$_4$-alkoxy are selected from F, Cl, Br, I, CF$_3$;

R$_7$, R$_8$, R$_{8a}$ are independently selected from the group consisting of H; C$_1$-C$_4$-alkyl; heterocyclyl; and C$_{3-7}$ cycloalkyl, wherein C$_1$-C$_4$-alkyl; heterocyclyl; and C$_{3-7}$ cycloalkyl are optionally substituted with one or more substituents independently selected from the group consisting of F, Cl, Br, I and CF$_3$;

Y is a carboxy group —C(O)OH or a substituted or unsubstituted tetrazole group

R$_9$ and R$_{10}$ are independently selected from the group consisting of: H, F, and CF$_3$;

and solvates, hydrates, esters, and pharmaceutically acceptable salts thereof.

The term "substituted" as used herein includes both part and full substitution. Substituents can be either saturated or unsaturated.

In case R$_5$ and R$_6$ are part of a ring, the ring can be substituted by C$_1$-C$_4$-alkyl or OH, F, Cl, Br, I and CF$_3$ Esters are those according to formula (I) in which H of the carboxy group is replaced by an organic residue R$_{7a}$. Suitable organic residues are known to a person skilled in the art. Preferred R$_{7a}$ include the following: an unsubstituted or at least monosubstituted alkyl, preferably a C$_1$-C$_{10}$ alkyl, an alkenyl, preferably C$_2$-C$_{10}$-alkenyl, an alkynyl, preferably C$_3$-C$_{10}$-alkynyl, and an unsubstituted or at least monosubstituted, saturated or unsaturated, non-aromatic or aromatic ring having 3 to 6 C-atoms, and which may contain in the ring one or more heteroatoms from the group N, S or O, and which heteroatom may be identical or different if more than one heteroatom is present. Said substituents being selected from the group consisting of halogen, alkyl, alkenyl, alkynyl, N, S, O, carboxy, sulphonyl, and the like and which can be further substituted.

Examples for current aromatic groups include aryl groups, for example phenyl groups, and heteroaryl groups, which aryl and heteroaryl groups may be substituted, preferably by the substituents given above.

In another embodiment of the invention:
A is O or NH;
X is —CR$_5$R$_6$ wherein R$_5$ and R$_6$ are independently selected from the group consisting of H, CH$_3$, C$_2$H$_5$, i-C$_3$H$_7$, n-C$_3$H$_7$, i-C$_4$H$_9$, n-C$_4$H$_9$, sec-C$_4$H$_9$, and tert-C$_4$H$_9$; wherein in any of the alkyl groups one or more H atoms optionally can be substituted with one or more substituents independently selected from the group consisting of OH, F, Cl, Br and I; or R$_5$, R$_6$ jointly form together with the carbon atom to which they are attached a cyclopropyl ring;

R$_1$, R$_2$, R$_3$ and R$_4$ are independently selected from the group consisting of H, OH, C$_{(1-4)}$alkyl, C$_{(1-4)}$alkoxy, —N(CH$_3$)$_2$, —SO$_2$CH$_3$, CN, OCF$_3$, —C(O)CH$_3$, OCH$_3$, CF$_3$, F, and Cl; wherein said C$_{(1-4)}$alkyl and C$_{(1-4)}$alkoxy are optionally independently substituted with one, two, or three substituents selected from the group consisting of I, Br, F, and Cl;

Y is CO$_2$H;

R$_9$ and R$_{10}$ are independently selected from the group consisting of: H, F, and CF$_3$;

and solvates, hydrates, esters, and pharmaceutically acceptable salts thereof.

In another embodiment of the invention:
A is O or NH;
X is —CR$_5$R$_6$ wherein R$_5$ and R$_6$ are H, CH$_3$, C$_2$H$_5$, i-C$_3$H$_7$, n-C$_3$H$_7$, i-C$_4$H$_9$, n-C$_4$H$_9$, sec-C$_4$H$_9$, or tert-C$_4$H$_9$;

R$_1$, R$_2$, R$_3$ and R$_4$ are independently selected from the group consisting of H, OH, C$_{(1-4)}$alkyl, C$_{(1-4)}$alkoxy, —N(CH$_3$)$_2$, —SO$_2$CH$_3$, CN, OCF$_3$, —C(O)CH$_3$, OCH$_3$, CF$_3$, F, and Cl; wherein said C$_{(1-4)}$alkyl and C$_{(1-4)}$alkoxy are optionally independently substituted with one, two, or three substituents selected from the group consisting of I, Br, F, and Cl;

Y is CO$_2$H;

R$_9$ and R$_{10}$ are independently selected from the group consisting of: H, F, and CF$_3$;

and solvates, hydrates, esters, and pharmaceutically acceptable salts thereof.

In another embodiment of the invention:
A is O or NH;
X is —CR$_5$R$_6$ wherein R$_5$ and R$_6$ are H, CH$_3$, C$_2$H$_5$, i-C$_3$H$_7$, n-C$_3$H$_7$, i-C$_4$H$_9$, n-C$_4$H$_9$, sec-C$_4$H$_9$, or tert-C$_4$H$_9$;
Y is CO$_2$H;
R$_1$, and R$_2$ are independently selected from the group consisting of CF$_3$, H, F, Cl, OCH$_3$, C$_{(1-4)}$alkyl, and CN.
R$_3$ and R$_4$ are independently selected from the group consisting of H, CF$_3$, F, and Cl;
R$_9$ is H or F;
R$_{10}$ is H;

and solvates, hydrates, esters, and pharmaceutically acceptable salts thereof.

In another embodiment of the invention, the object is achieved by a compound having the general Formula (I*)

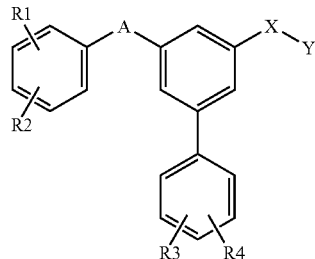

Formula I* wherein
A is O, S or NH,
X is a bond or a group —CR$_5$R$_6$ wherein R$_5$ and R$_6$ are, independently of each other, selected from the group consisting of H; alkyl selected from the group CH$_3$, C$_2$H$_5$, i-C$_3$H$_7$, n-C$_3$H$_7$, i-C$_4$H$_9$, n-C$_4$H$_9$, sec-C$_4$H$_9$, tert-C$_4$H$_9$; alkenyl selected from C$_2$H$_3$, i-C$_3$H$_5$, n-C$_3$H$_5$, n-C$_4$H$_7$, i-C$_4$H$_7$, sec-C$_4$H$_7$; wherein in any of the alkyl or alkenyl groups one or more H atoms optionally can be substituted with one or more substituents independently selected from the group consisting of OH, F, Cl, Br, I and $CF_3$; or $R_5$ and $R_6$ being part of a ring, either saturated or unsaturated, substituted or unsubstituted, having 3 to 6 C-atoms, and which may contain in the ring one or more heteroatoms from the group N, S or O, and which heteroatom may be identical or different if more than one heteroatom is present;

$R_1$, $R_2$, $R_3$ and $R_4$ are independently selected from the group consisting of H; F; Cl; Br; I; CN; OH; $C(O)N(R_7R_8)$; $S(O)_2R_7$; $SO_2N(R_7R_8)$; $S(O)N(R_7R_8)$; $N(R_7)S(O)_2R_8$; $N(R_8)S(O)R_8$; $S(O)_2R_7$; $N(R_7)S(O)_2N(R_8R_{8a})$; $SR_7$; $N(R_7R_8)$; $N(R_7)C(O)R_8$; $N(R_7)C(O)N(R_8R_{8a})$; $N(R_7)C(O)OR_8$; $OC(O)N(R_7R_8)$; $C(O)R_7$; substituted and unsubstituted $C_1$-$C_4$-alkyl and substituted and unsubstituted $C_1$-$C_4$-alkoxy, and wherein the substituents of both groups $C_1$-$C_4$-alkyl and $C_1$-$C_4$-alkoxy are selected from F, Cl, Br, I, $CF_3$;

$R_7$, $R_8$, $R_{8a}$ are independently selected from the group consisting of H; $C_1$-$C_4$-alkyl; heterocyclyl; and $C_{3-7}$ cycloalkyl, wherein $C_1$-$C_4$-alkyl; heterocyclyl; and $C_{3-7}$ cycloalkyl are optionally substituted with one or more substituents independently selected from the group consisting of F, Cl, Br, I and $CF_3$;

Y is a carboxy group —C(O)OH or a substituted or unsubstituted tetrazole group and/or a salt or ester thereof.

The term "substituted" as used herein includes both part and full substitution. Substituents can be either saturated or unsaturated.

In case $R_5$ and $R_6$ are part of a ring, the ring can be substituted by $C_1$-$C_4$-alkyl or OH, F, Cl, Br, I and $CF_3$ Esters are those according to formula (I) in which H of the carboxy group is replaced by an organic residue $R_{7a}$. Suitable organic residues are known to a person skilled in the art. Preferred $R_{7a}$ include the following: an unsubstituted or at least monosubstituted alkyl, preferably a $C_1$-$C_{10}$ alkyl, an alkenyl, preferably $C_2$-$C_{10}$-alkenyl, an alkynyl, preferably $C_3$-$C_{10}$-alkynyl, and an unsubstituted or at least monosubstituted, saturated or unsaturated, non-aromatic or aromatic ring having 3 to 6 C-atoms, and which may contain in the ring one or more heteroatoms from the group N, S or O, and which heteroatom may be identical or different if more than one heteroatom is present. Said substituents being selected from the group consisting of halogen, alkyl, alkenyl, alkynyl, N, S, O, carboxy, sulphonyl, and the like and which can be further substituted.

Examples for current aromatic groups include aryl groups, for example phenyl groups, and heteroaryl groups, which aryl and heteroaryl groups may be substituted, preferably by the substituents given above.

The term "$C_1$-$C_4$-alkyl" refers to methyl, ethyl, n-propyl, iso-propyl, n-butyl, iso-butyl, sec-butyl, and tert.-butyl.

"$C_{3-7}$ cycloalkyl" or "$C_{3-7}$ cycloalkyl ring" means a cyclic alkyl chain having 3-7 carbon atoms, e.g. cyclopropyl, cyclobutyl, cyclopentyl, cyclohexyl, cyclohexenyl, cycloheptyl. Each hydrogen of a cycloalkyl carbon may be replaced by a substituent.

"Heterocyclyl" or "heterocycle" means a cyclopentane, cyclohexane or cycloheptane ring that may contain up to the maximum number of double bonds (aromatic or non-aromatic ring which is fully, partially or un-saturated) wherein at least one carbon atom up to 4 carbon atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a heterocycle include but are not restricted to furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, azepine or homopiperazine. "Heterocycle" means also azetidine.

In preferred embodiments, the invention relates to a compound having the general formula (I) wherein A, X; Y; $R_1$ and $R_2$; and $R_3$, $R_4$, $R_5$ and $R_6$ independently of each other have the following meanings:

A is O; and/or

X is a group —$CR_5R_6$ wherein $R_5$ and $R_6$ are, independently of each other, selected from the group consisting of H; alkyl selected from the group $CH_3$, $C_2H_5$, i-$C_3H_7$, n-$C_3H_7$, i-$C_4H_9$, n-$C_4H_9$, sec-$C_4H_9$, tert-$C_4H_9$; wherein in any of the alkyl groups one or more H atoms optionally can be substituted with one or more substituents independently selected from the group consisting of OH, F, Cl, Br and I; and/or $R_1$, $R_2$, $R_3$ and $R_4$ are independently selected from the group consisting of H; OH; $C_1$-$C_4$-alkyl or $C_1$-$C_4$-alkoxy, substituted partly or fully by F, Cl, Br, I; and/or $R_5$ and $R_6$ being H; or $R_5$ being H and $R_6$ being $CH_3$, $C_2H_5$, $C_3H_7$ or $C_4H_9$ or isomers thereof, or $R_1$ and $R_2$ being $CH_3$ or $R_1$, $R_2$ jointly form together with the carbon atom to which they are attached a cyclopropyl ring; and/or Y is a carboxy group and/or a salt or ester thereof.

Within this group of embodiments, it is even more preferred if all the groups A; X; Y; $R_1$, $R_2$, $R_3$, $R_4$, $R_5$ and $R_6$ have the meanings defined beforehand.

It is even more preferred if A; X; Y; $R_1$ and $R_2$; and $R_3$, $R_4$, $R_5$ and $R_6$ independently of each other have the following meanings:

A is O; X is a group —$CR_5R_6$ with $R_5$ and $R_6$ being H; or $R_5$ being H and $R_6$ being $CH_3$, $C_2H_5$, $C_3H_7$ or $C_4H_9$ or isomers thereof, or $R_5$ and $R_6$ being $CH_3$ or $R_5$, $R_6$ jointly form together with the carbon atom to which they are attached a cyclopropyl ring; and/or $R_1$, $R_2$, $R_3$ and $R_4$ are independently selected from the group consisting of H; OH; $C_1$-$C_4$-alkyl or $C_1$-$C_4$-alkoxy, substituted partly or fully by F, Cl, Br, I; and/or and/or Y is a carboxy group and/or a salt or ester thereof.

Within this group of embodiments, it is even more preferred if all the groups A; X; Y; $R_1$, $R_2$, $R_3$, $R_4$, $R_5$ and $R_6$ have the meanings defined beforehand.

It is still more preferred if A; X; Y; $R_1$ and $R_2$; and $R_3$, $R_4$, $R_5$ and $R_6$ independently of each other have the following meanings:

A is O;

X is a group —$CR_5R_6$, with $R_5$ and $R_6$ being H; or $R_5$ being H and $R_6$ being $CH_3$, $C_2H_5$, $C_3H_7$ or $C_4H_9$ or isomers thereof;

Y is a carboxy group $R_1$, $R_2$, $R_3$ and $R_4$ are independently selected from the group consisting of H, OH, $CH_3$, $OCH_3$, $CF_3$, F, and Cl; and/or and/or a salt or ester thereof.

Within this group of embodiments, it is even more preferred if all the groups A; X; Y; $R_1$ and $R_2$; and $R_3$, $R_4$, $R_5$ and $R_6$ have the meanings defined beforehand.

In another embodiment, the invention relates to compounds selected from the group consisting of
2-(5-(4-fluorophenoxy)-4'-trifluoromethyl-biphenyl-3-yl)-pentanoic acid (I)

2-(5-(phenoxy)-4'-trifluoromethyl-biphenyl-3-yl)-pentanoic acid (II)

and solvates, hydrates, esters, and pharmaceutically acceptable salts thereof.

In another embodiment, the invention relates to compounds selected from the group consisting of:

| Compound # | Structure | Chemical Name |
|---|---|---|
| 1 | 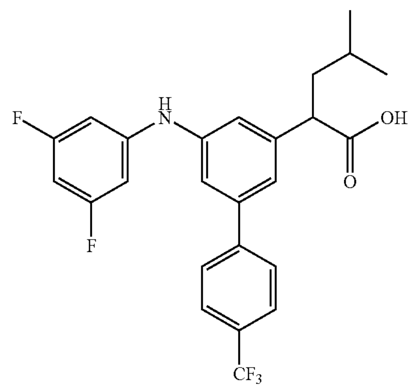 | 2-[5-(3,5-Difluoro-phenylamino)-4'-trifluoromethyl-biphenyl-3-yl]-4-methyl-pentanoic acid |
| 2 | 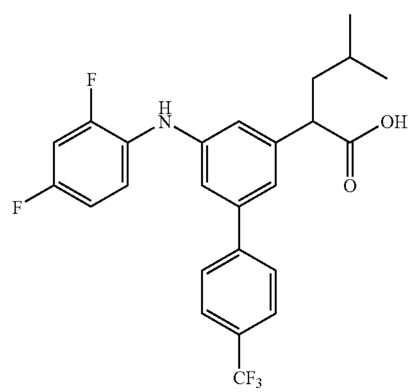 | 2-[5-(2,4-Difluoro-phenylamino)-4'-trifluoromethyl-biphenyl-3-yl]-4-methyl-pentanoic acid |
| 3 | 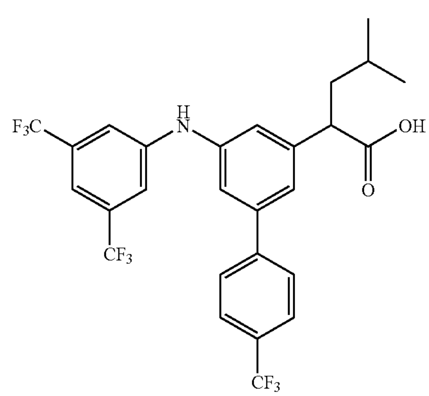 | 2-[5-(3,5-Bis-trifluoromethyl-phenylamino)-4'-trifluoromethyl-biphenyl-3-yl]-4-methyl-pentanoic acid |

-continued

| Compound # | Structure | Chemical Name |
|---|---|---|
| 4 | 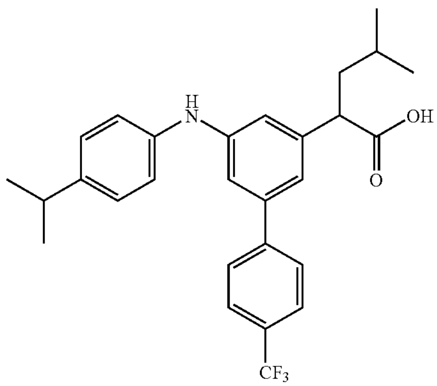 | 2-[5-(4-Isopropyl-phenylamino)-4'-trifluoromethyl-biphenyl-3-yl]-4-methyl-pentanoic acid |
| 5 | 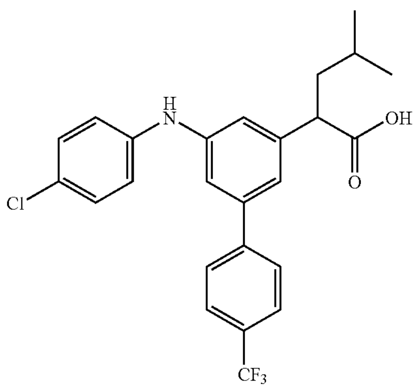 | 2-[5-(4-Chloro-phenylamino)-4'-trifluoromethyl-biphenyl-3-yl]-4-methyl-pentanoic acid |
| 6 | 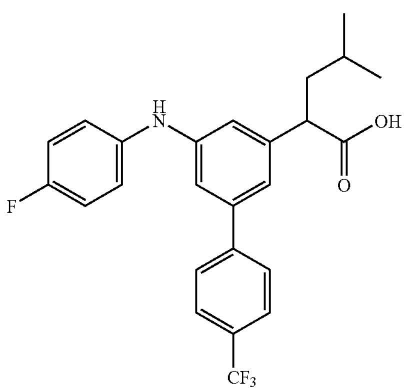 | 2-[5-(4-Fluoro-phenylamino)-4'-trifluoromethyl-biphenyl-3-yl]-4-methyl-pentanoic acid |
| 7 | 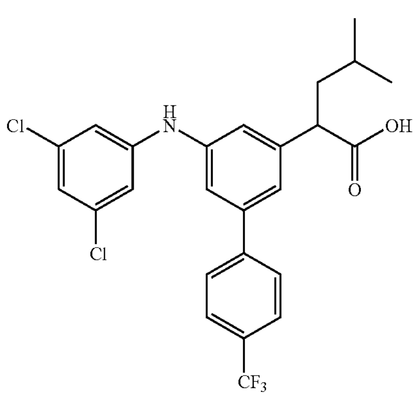 | 2-[5-(3,5-Dichloro-phenylamino)-4'-trifluoromethyl-biphenyl-3-yl]-4-methyl-pentanoic acid |

-continued

| Compound # | Structure | Chemical Name |
|---|---|---|
| 8 | 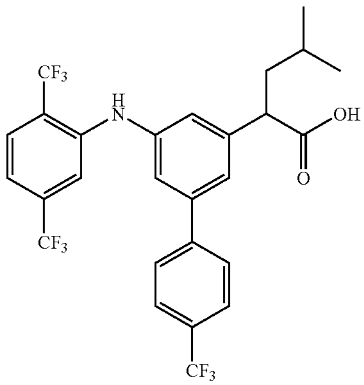 | 2-[5-(2,5-Bis-trifluoromethyl-phenylamino)-4'-trifluoromethyl-biphenyl-3-yl]-4-methyl-pentanoic acid |
| 9 | 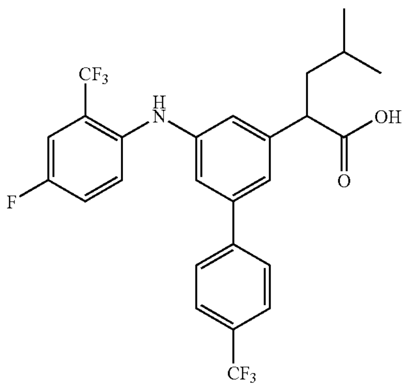 | 2-[5-(4-Fluoro-2-trifluoromethyl-phenylamino)-4'-trifluoromethyl-biphenyl-3-yl]-4-methyl-pentanoic acid |
| 10 | 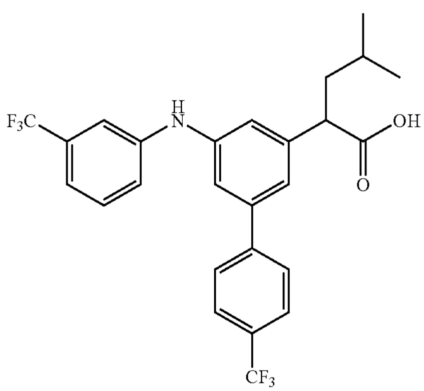 | 4-Methyl-2-[4'-trifluoromethyl-5-(3-trifluoromethyl-phenylamino)-biphenyl-3-yl]-pentanoic acid |
| 11 | 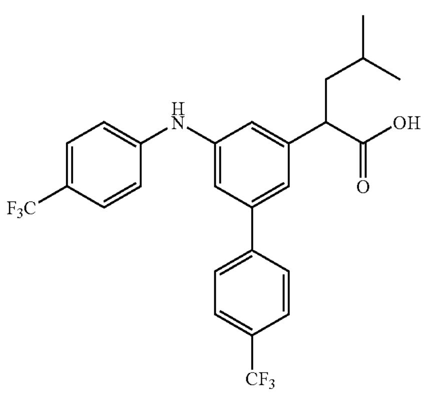 | 4-Methyl-2-[4'-trifluoromethyl-5-(4-trifluoromethyl-phenylamino)-biphenyl-3-yl]-pentanoic acid |

-continued
| Compound # | Structure | Chemical Name |
|---|---|---|
| 12 | 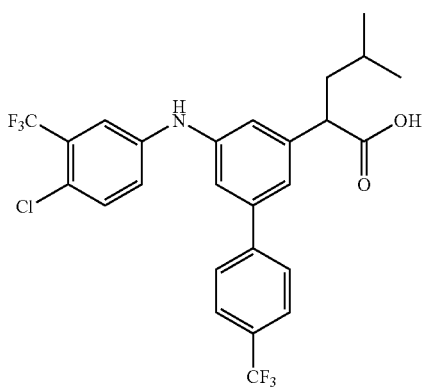 | 2-[5-(4-Chloro-3-trifluoromethyl-phenylamino)-4'-trifluoromethyl-biphenyl-3-yl]-4-methyl-pentanoic acid |
| 13 | 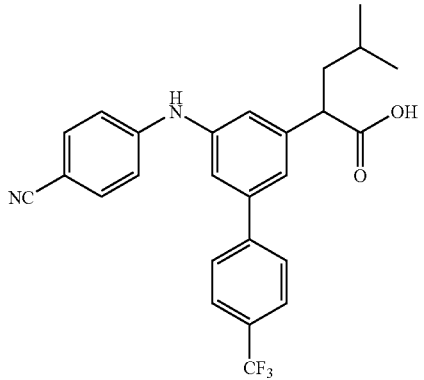 | 2-[5-(4-Cyano-phenylamino)-4'-trifluoromethyl-biphenyl-3-yl]-4-methyl-pentanoic acid |
| 14 | 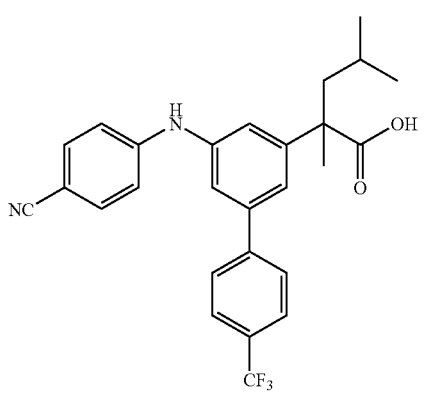 | 2-[5-(4-Cyano-phenylamino)-4'-trifluoromethyl-biphenyl-3-yl]-2,4-dimethyl-pentanoic acid |

-continued
| Compound # | Structure | Chemical Name |
|---|---|---|
| 15 | 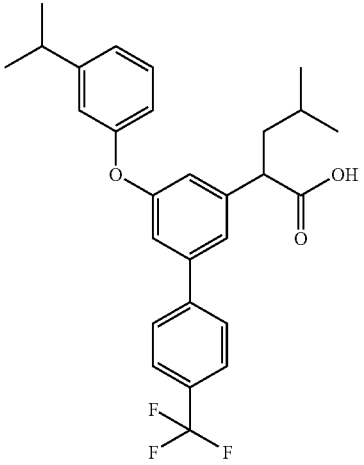 | 2-[5-(3-Isopropyl-phenoxy)-4'-trifluoromethyl-biphenyl-3-yl]-4-methyl-pentanoic acid |
| 16 | 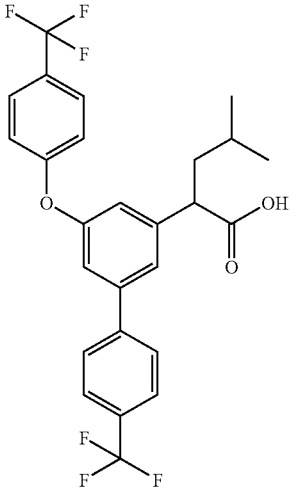 | 4-Methyl-2-[4'-trifluoromethyl-5-(4-trifluoromethyl-phenoxy)-biphenyl-3-yl]-pentanoic acid |
| 17 | 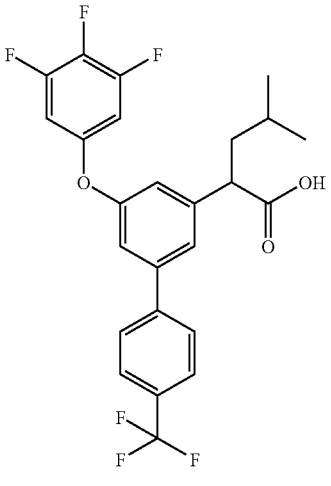 | 4-Methyl-2-[4'-trifluoromethyl-5-(3,4,5-trifluoro-phenoxy)-biphenyl-3-yl]-pentanoic acid |

-continued
| Compound # | Structure | Chemical Name |
|---|---|---|
| 18 | 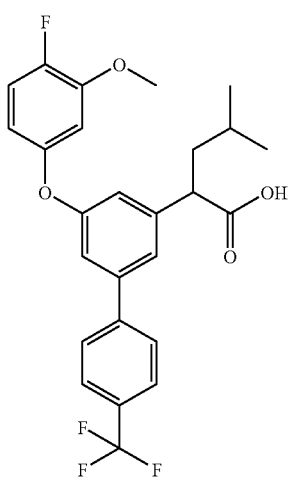 | 2-[5-(4-Fluoro-3-methoxy-phenoxy)-4'-trifluoromethyl-biphenyl-3-yl]-4-methyl-pentanoic acid |
| 19 | 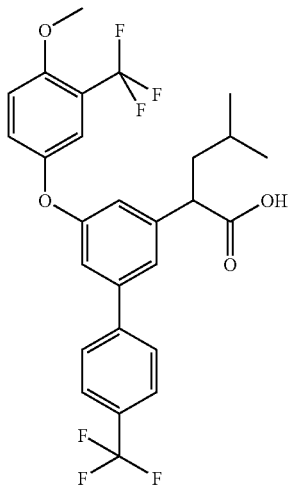 | 2-[5-(4-Methoxy-3-trifluoromethyl-phenoxy)-4'-trifluoromethyl-biphenyl-3-yl]-4-methyl-pentanoic acid |
| 20 | 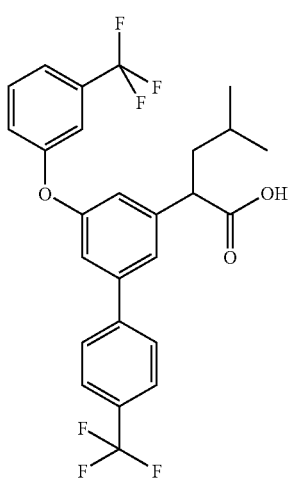 | 2 4-Methyl-2-[4'-trifluoromethyl-5-(3-trifluoromethyl-phenoxy)-biphenyl-3-yl]-pentanoic acid |

| Compound # | Structure | Chemical Name |
|---|---|---|
| 21 | 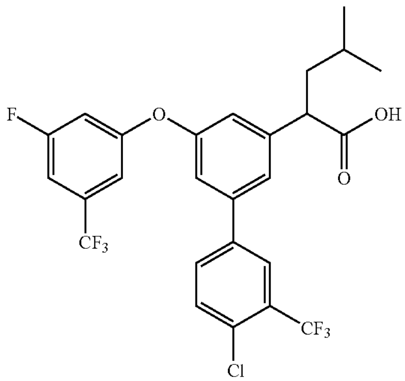 | 4-Methyl-2-[4'-chloro-3'-trifluoromethyl-5-(3-fluoro-5-trifluoromethylphenoxy)-biphenyl-3-yl]-pentanoic acid |
| 22 | 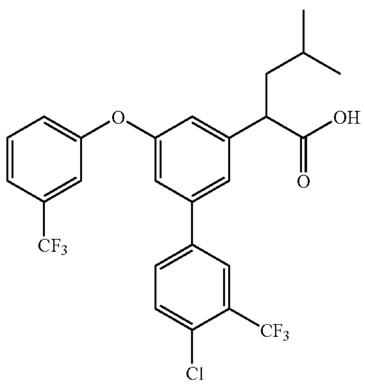 | 4-Methyl-2-[4'-chloro-3'-trifluoromethyl-5-(3-trifluoromethylphenoxy)-biphenyl-3-yl]-pentanoic acid |
| 23 | 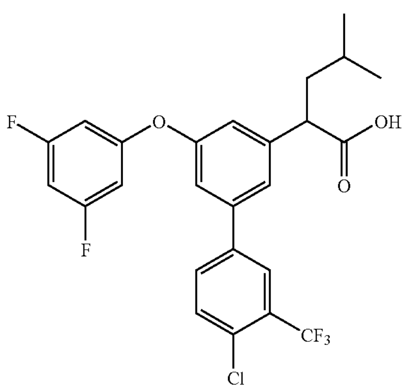 | 4-Methyl-2-[4'-chloro-3'-trifluoromethyl-5-(3,5-difluorophenoxy)-biphenyl-3-yl]-pentanoic acid |
| 24 | 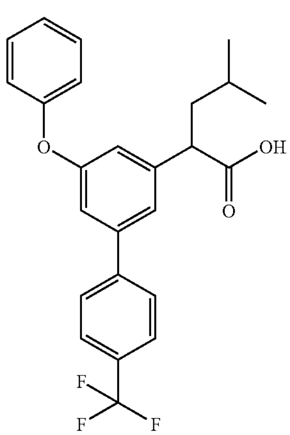 | 4-Methyl-2-(5-phenoxy-4'-trifluoromethyl-biphenyl-3-yl)-pentanoic acid |

-continued
| Compound # | Structure | Chemical Name |
|---|---|---|
| 25 | 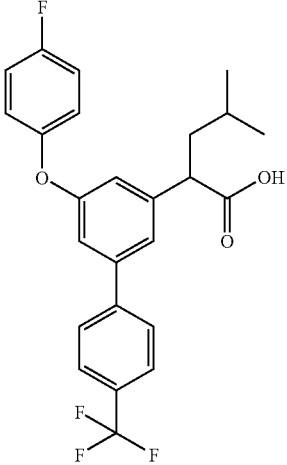 | 2-[5-(4-Fluoro-phenoxy)-4'-trifluoromethyl-biphenyl-3-yl]-4-methyl-pentanoic acid |
| 26 | 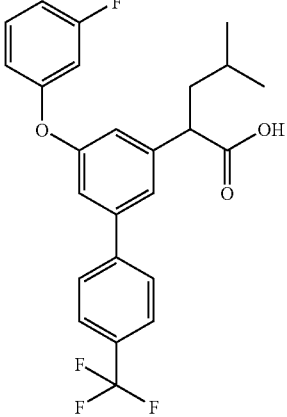 | 2-[5-(3-Fluoro-phenoxy)-4'-trifluoromethyl-biphenyl-3-yl]-4-methyl-pentanoic acid |
| 27 | 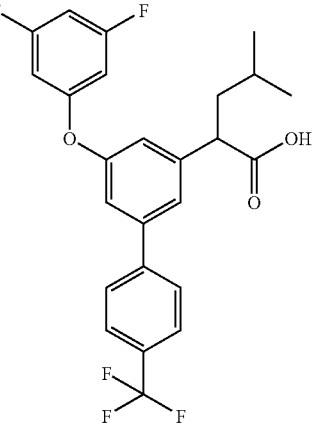 | 2-[5-(3,5-Difluoro-phenoxy)-4'-trifluoromethyl-biphenyl-3-yl]-4-methyl-pentanoicacid |

-continued
| Compound # | Structure | Chemical Name |
|---|---|---|
| 28 | 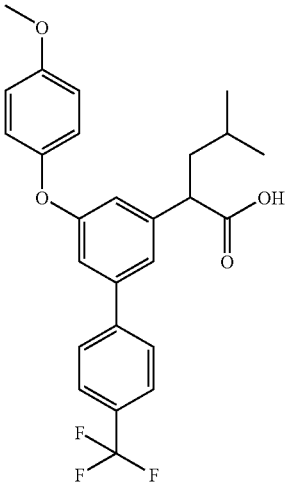 | 2-[5-(4-Methoxy-phenoxy)-4'-trifluoromethyl-biphenyl-3-yl]-4-methyl-pentanoic acid |
| 29 | 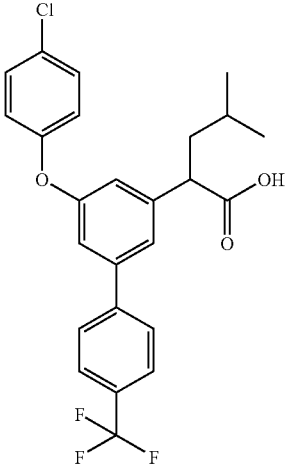 | 2-[5-(4-Chloro-phenoxy)-4'-trifluoromethyl-biphenyl-3-yl]-4-methyl-pentanoic acid |
| 30 | 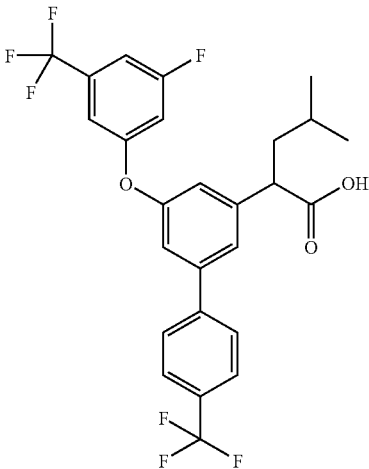 | 2-[5-(3-Fluoro-5-trifluoromethyl-phenoxy)-4'-trifluoromethyl-biphenyl-3-yl]-4-methyl-pentanoic acid |

-continued

| Compound # | Structure | Chemical Name |
|---|---|---|
| 31 | 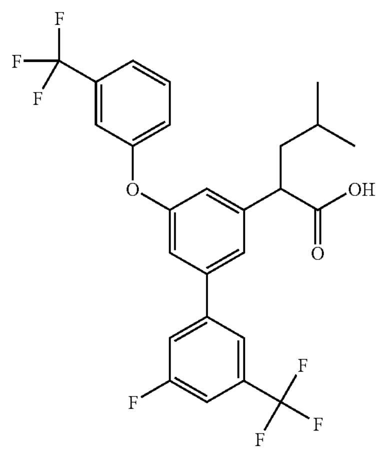 | 2-[3'-Fluoro-5'-trifluoromethyl-5-(3-trifluoromethyl-phenoxy)-biphenyl-3-yl]-4-methyl-pentanoic acid |
| 32 | 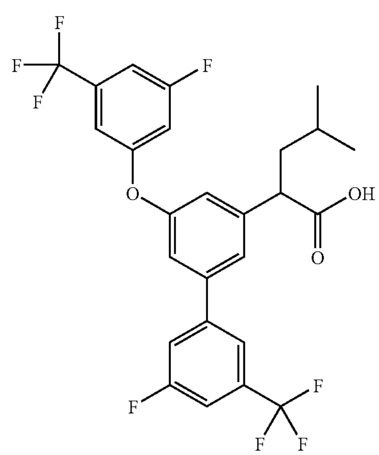 | 2-[3'-Fluoro-5-(3-fluoro-5-trifluoromethyl-phenoxy)-5'-trifluoromethyl-biphenyl-3-yl]-4-methyl-pentanoic acid |
| 33 | 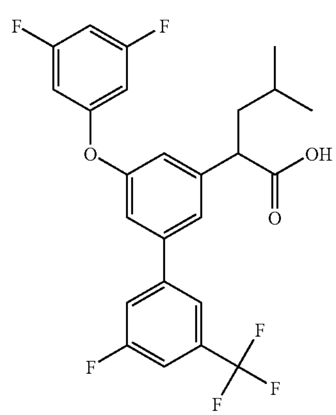 | 2-[5-(3,5-Difluoro-phenoxy)-3'-fluoro-5'-trifluoromethyl-biphenyl-3-yl]-4-methyl-pentanoic acid |

-continued

| Compound # | Structure | Chemical Name |
|---|---|---|
| 34 | 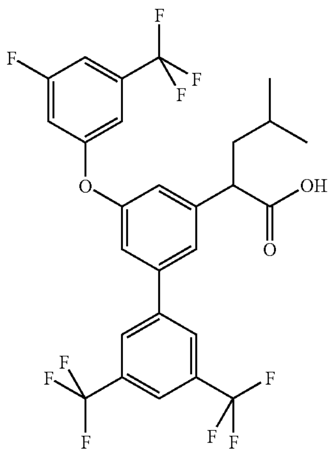 | 2-[5-(3-Fluoro-5-trifluoromethyl-phenoxy)-3',5'-bis-trifluoromethyl-biphenyl-3-yl]-4-methyl-pentanoic acid |
| 35 | 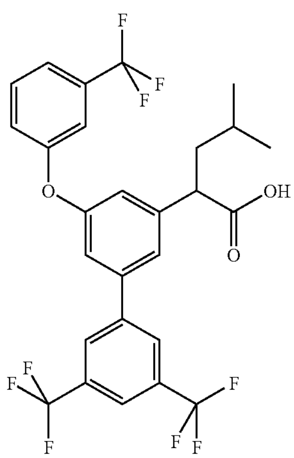 | 2-[3',5'-Bis-trifluoromethyl-5-(3-trifluoromethyl-phenoxy)-biphenyl-3-yl]-4-methyl-pentanoic acid |
| 36 | 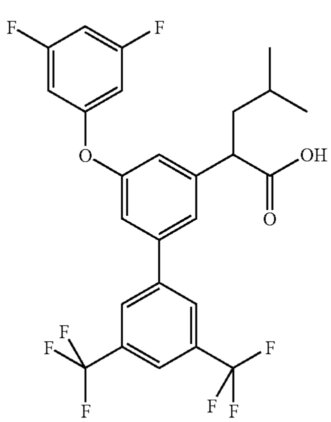 | 2-[5-(3,5-Difluoro-phenoxy)-3',5'-bis-trifluoromethyl-biphenyl-3-yl]-4-methyl-pentanoic acid |

| Compound # | Structure | Chemical Name |
|---|---|---|
| 37 | 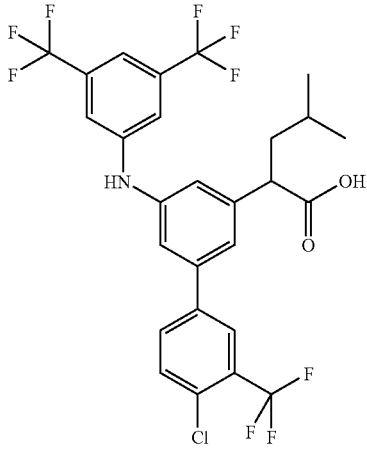 | 2-[5-(3,5-Bis-trifluoromethyl-phenylamino)-4'-chloro-3'-trifluoromethyl-biphenyl-3-yl]-4-methyl-pentanoic acid |
| 38 | 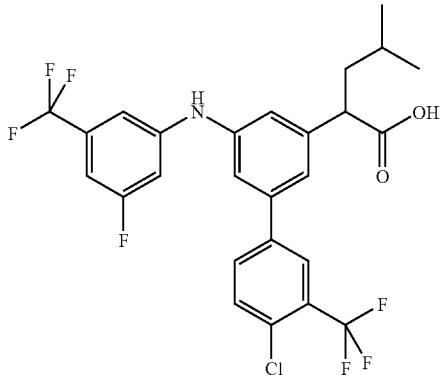 | 2-[4'-Chloro-5-(3-fluoro-5-trifluoromethyl-phenylamino)-3'-trifluoromethyl-biphenyl-3-yl]-4-methyl-pentanoic acid |
| 39 | 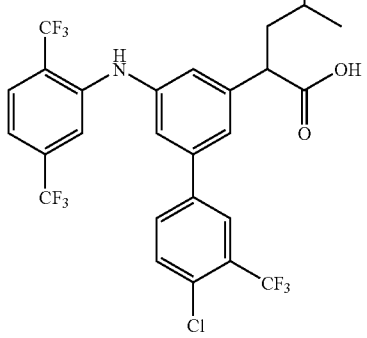 | 2-[4'-Chloro-5-(2,5-bis-trifluoromethyl-phenylamino)-3'-trifluoromethyl-biphenyl-3-yl]-4-methyl-pentanoic acid |
| 40 | 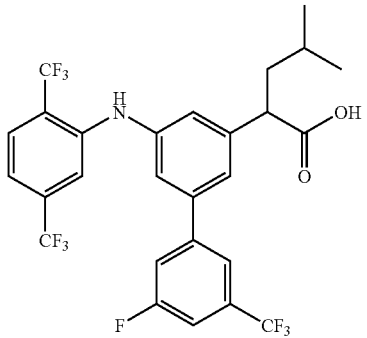 | 2-[5'-Fluoro-5-(2,5-bis-trifluoromethyl-phenylamino)-3'-trifluoromethyl-biphenyl-3-yl]-4-methyl-pentanoic acid |

| Compound # | Structure | Chemical Name |
|---|---|---|
| 41 | 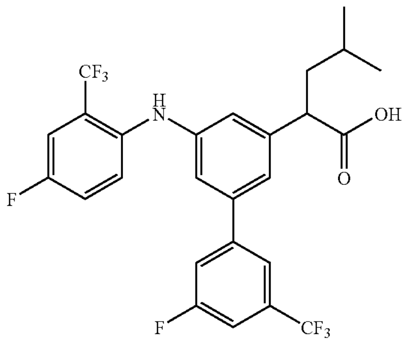 | 2-[5'-Fluoro-5-(4-fluoro-2-trifluoromethyl-phenylamino)-3'-trifluoromethyl-biphenyl-3-yl]-4-methyl-pentanoic acid |
| 42 | 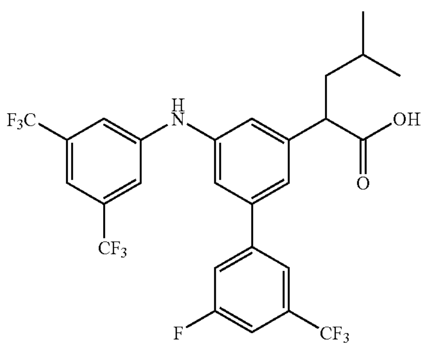 | 2-[5'-Fluoro-5-(3,5-bis-trifluoromethyl-phenylamino)-3'-trifluoromethyl-biphenyl-3-yl]-4-methyl-pentanoic acid |
| 43 | 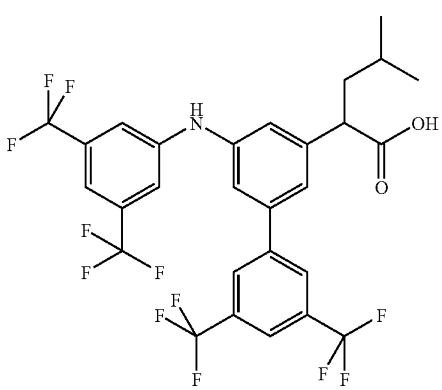 | 2-[5-(3,5-Bis-trifluoromethyl-phenylamino)-3',5'-bis-trifluoromethyl-biphenyl-3-yl]-4-methyl-pentanoic acid |
| 44 | 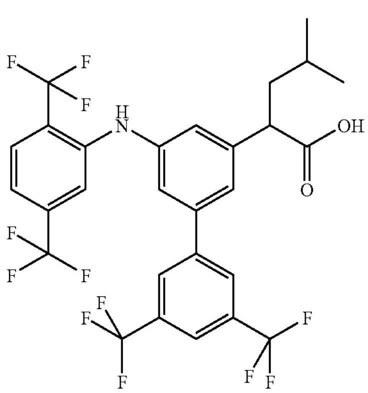 | 2-[5-(2,5-Bis-trifluoromethyl-phenylamino)-3',5'-bis-trifluoromethyl-biphenyl-3-yl]-4-methyl-pentanoic acid |

-continued

| Compound # | Structure | Chemical Name |
| --- | --- | --- |
| 45 | 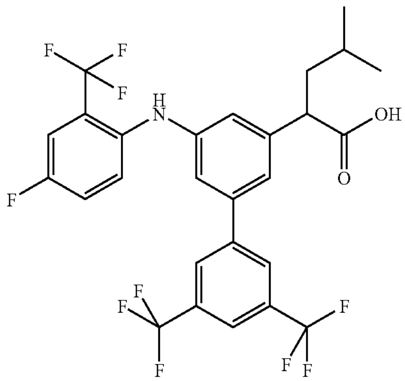 | 2-[5-(4-Fluoro-2-trifluoromethyl-phenylamino)-3',5'-bis-trifluoromethyl-biphenyl-3-yl]-4-methyl-pentanoic acid |
| 46 | | (R)-2-[5-(2,5-Bis-trifluoromethyl-phenylamino)-4'-trifluoromethyl-biphenyl-3-yl]-4-methyl-pentanoic acid | and solvates, hydrates, esters, and pharmaceutically acceptable salts thereof.

Some of the compounds of the inventions and/or salts or esters thereof will exist in different stereoisomeric forms. All of these forms are subjects of the invention.

Described below are exemplary salts of the compounds according to the invention which are included herein. The list of the different salts stated below is not meant to be complete and limiting.

Compounds according to the invention which contain one or more acidic groups can be used according to the invention, e.g. as their alkali metal salts, alkaline earth metal salts or ammonium salts. More precise examples of such salts include sodium salts, potassium salts, calcium salts, magnesium salts or salts with ammonia or organic amines such as, e.g. ethylamine, ethanolamine, triethanolamine or amino acids.

Compounds according to the invention which contain one or more basic groups, i.e. groups which can be protonated, can be used according to the invention in the form of their addition salts with inorganic or organic acids.

Examples for suitable acids include hydrogen chloride, hydrogen bromide, phosphoric acid, sulfuric acid, nitric acid, methanesulfonic acid, p-toluenesulfonic acid, napthalenedisulfonic acid, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid and other acids known to a person skilled in the art.

The term "pharmaceutically acceptable" means approved by a regulatory agency such as the EMEA (Europe) and/or the FDA (US) and/or any other national regulatory agency for use in animals, preferably in humans.

Compounds according to the invention which contain several basic groups can simultaneously form different salts.

If a compound according to the invention simultaneously contains acidic and basic groups in the molecule, the invention also includes, in addition to the salt forms mentioned, inner salts or betaines.

The respective salts of the compounds according to the invention can be obtained by customary methods which are known to the person skilled in the art, for example by contacting these with an organic or inorganic acid or base in a solvent or dispersant, or by anion exchange or cation exchange with other salts.

Furthermore, the invention includes all salts of the compounds according to the invention which, owing to low physiological compatibility, are not directly suitable for use in pharmaceuticals but which can be used, for example, as intermediates for chemical reactions or for the preparation of pharmaceutically acceptable salts or which might be suitable for studying γ-secretase modulating activity of a compound according of the invention in any suitable manner, such as any suitable in vitro assay.

The present invention furthermore includes all solvates of the compounds according to the invention.

The present invention furthermore includes derivatives/prodrugs (including the salts thereof) of the compounds according to the invention which contain physiologically tolerable and cleavable groups and which are metabolized in animals, preferably mammals, most preferably humans into a compound according to the invention.

The present invention furthermore includes the metabolites of the compounds according to the invention.

The term "metabolites" refers to all molecules derived from any of the compounds according to the invention in a cell or organism, preferably mammal.

Preferably the term "metabolites" relates to molecules which differ from any molecule which is present in any such cell or organism under physiological conditions.

The structure of the metabolites of the compounds according to the invention will be obvious to any person skilled in the art, using the various appropriate methods.

The compounds according to general formula (I) can be prepared according to methods published in the literature or by analogous methods.

Depending on the circumstances of the individual case, in order to avoid side reactions during the synthesis of a compound of the general formula (I), it can be necessary or advantageous to temporarily block functional groups by introducing protective groups and to deprotect them in a later stage of the synthesis, or to introduce functional groups in the form of precursor groups and at a later stage to convert them into the desired functional groups. Suitable synthetic strategies, protective groups and precursor groups are known to the person skilled in the art.

If desired, the compounds of the formula (I) can be purified by customary purification procedures, for example by recrystallization or chromatography. The starting materials for the preparation of the compounds of the formula (I) are commercially available or can be prepared according to or analogously to literature procedures.

These can serve as a basis for the preparation of the other compounds according to the invention by several methods well known to the person skilled in the art.

The invention also relates to a compound of the invention for use as a medicament. The compounds are as defined above, furthermore with respect to the medicament the embodiments as described below with respect to the use of the invention, e.g. formulation, application and combination, also apply to this aspect of the invention.

In particular the compounds according to the invention are suitable for the treatment of Alzheimer's disease.

Details relating to said use are further disclosed below.

The compounds can be used for modulation of γ-secretase activity.

As used herein, the term "modulation of γ-secretase activity" refers to an effect on the processing of APP by the γ-secretase-complex. Preferably it refers to an effect in which the overall rate of processing of APP remains essentially as without the application of said compounds, but in which the relative quantities of the processed products are changed, more preferably in such a way that the amount of the Aβ42-peptide produced is reduced. For example a different Abeta species can be produced (e.g. Abeta-38 or other Abeta peptide species of shorter amino acid sequence instead of Abeta-42) or the relative quantities of the products are different (e.g. the ratio of Abeta-40 to Abeta-42 is changed, preferably increased).

Gamma secretase activity can e.g. be measured by determining APP processing, e.g. by determining the levels of Abeta petide species produced, most importantly levels of It has been previously shown that the γ-secretase complex is also involved in the processing of the Notch-protein. Notch is a signaling protein which plays a crucial role in developmental processes (e.g. reviewed in Schweisguth F (2004) Curr. Biol. 14, R129).

With respect to the use of said compounds for the modulation of γ-secretase activity in therapy, it seems particularly advantageous not to interfere with the Notch-processing activity of the γ-secretase activity in order to avoid putative undesired side-effects.

Thus, compounds are preferred which do not show an effect on the Notch-processing activity of the γ-secretase-complex.

Within the meaning of the invention, "effect on the Notch processing activity" includes both an inhibition or an activation of the Notch-processing activity by a certain factor.

A compound is defined as not having an effect on the Notch processing activity, if said factor is smaller than 20, preferably smaller than 10, more preferably smaller than 5, most preferably smaller than 2 in the respective assay as described in Shimizu et al (2000) Mol. Cell. Biol, 20: 6913 at a concentration of 30 µM.

Such a γ-secretase modulation can be carried out, e.g. in animals such as mammals. Exemplary mammals are mice, rats, guinea pigs, monkeys, dogs, cats. The modulation can also be carried out in humans. In a particular embodiment of the invention, said modulation is performed in vitro or in cell culture. As known to the person skilled in the art, several in vitro and cell culture assays are available.

Exemplary assays useful for measuring the production of C-terminal APP fragments in cell lines or transgenic animals by Western blot analysis include but are not limited to those described in Yan et al., 1999, Nature 402, 533-537.

An example of an in vitro γ-secretase assay is described in WO-03/008635. In this assay a suitable peptide substrate is contacted with a γ-secretase preparation and the ability to cleave the substrate is measured.

Concentrations of the various products of the γ-secretase cleavage (the Aβ-peptides) can be determined by various methods known to a person skilled in the art. Examples for such methods include determination of the peptides by mass-spectrometry or detection by antibodies.

Exemplary assays useful for the characterization of the profile of soluble Abeta peptides in cultured cell media and biological fluids include but are not limited to those described by Wang et al., 1996, J. Biol. Chem. 271, 31894-31902. In this assay a combination of immunoprecipitation of Abeta-peptides with specific antibodies and detection and quantification of the peptide species with matrix-assisted laser desorption ionization time-of-flight mass spectrometry is used.

Exemplary assays useful for measuring the production of Abeta-40 and Abeta-42 peptides by ELISA include but are not limited to those described in Vassar et al, 1999, Science 286, 735-741. Further information is disclosed for example in N. Ida et al. (1996) J. Biol. Chem. 271, 22908, and M. Jensen et al. (2000) Mol. Med. 6, 291. Suitable antibodies are available for example from The Genetics Company, Inc., Switzerland. Antibody-based kits are also available from Innogenetics, Belgium.

Cells which can be employed in such assays include cells which endogenously express the γ-secretase complex and transfected cells which transiently or stably express some or all interactors of the γ-secretase complex. Numerous available cell lines suitable for such assays are known to the skilled person. Cells and cell lines of neuronal or glial origin are particularly suitable. Furthermore, cells and tissues of the brain as well as homogenates and membrane preparations thereof may be used (Xia et al., 1998, Biochemistry 37, 16465-16471).

Such assays might be carried out for example to study the effect of the compounds according to the invention in different experimental conditions and configurations.

Furthermore, such assays might be carried out as part of functional studies on the γ-secretase complex.

For example, either one or more interactors (either in their wild-type form or carrying certain mutations and/or modifications) of the γ-secretase complex of an animal, preferably a mammal, more preferably humans, might be expressed in certain cell lines and the effect of the compounds according to the invention might be studied.

Mutated forms of the interactor(s) used can either be mutated forms which have been described in certain animals, preferably mammals, more preferably humans or mutated forms which have not previously been described in said animals.

Modifications of the interactors of the γ-secretase complex include both any physiological modification of said interactors and other modifications which have been described as modifications of proteins in a biological system.

Examples of such modifications include, but are not limited to, glycosylation, phosphorylation, prenylation, myristylation and farnesylation.

Furthermore, the compounds according to the invention can be used for the preparation of a medicament for the modulation of γ-secretase activity.

The invention further relates to the use of said compounds for the preparation of a medicament for the modulation of γ-secretase activity.

The activity of the γ-secretase can be modulated in different ways, i.e. resulting in different profiles of the various Aβ-peptides.

Uses of a compound for the modulation of γ-secretase activity resulting in a decrease in the relative amount of Aβ42-peptides produced are preferred.

Respective dosages, routes of administration, formulations etc are disclosed further below.

The invention further relates to the use of the compounds according to the invention for the treatment of a disease associated with an elevated level of Aβ42-production. The disease with elevated levels of Abeta peptide production and deposition in the brain is typically Alzheimer's disease (AD), cerebral amyloid angiopathy, multi-infarct dementia, dementia pugilistica or Down syndrome, preferably AD.

As used herein, the term "treatment" is intended to refer to all processes, wherein there may be a slowing, interrupting, arresting, or stopping of the progression of a disease, but does not necessarily indicate a total elimination of all symptoms.

As used herein, the term "elevated level of Aβ42-production" refers to a condition in which the rate of production of Aβ42-peptide is increased due to an overall increase in the processing of APP or, preferably, it refers to a condition in which the production of the Aβ42 peptide is increased due to a modification of the APP-processing profile in comparison to the wild-type APP and non-pathological situation.

As outlined above, such an elevated Aβ42-level is a hallmark of patients developing or suffering from Alzheimer's disease.

One advantage of the compounds or a part of the compounds of the present invention may lie in their enhanced CNS-penetration.

Furthermore the invention relates to a pharmaceutical composition comprising a compound according to the invention in a mixture with an inert carrier.

In a preferred embodiment, the invention relates to a pharmaceutical composition comprising a compound according to the invention in a mixture with an inert carrier, where said inert carrier is a pharmaceutical carrier.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

Furthermore, the invention relates to methods for the preparation of a compound according to the invention.

In one embodiment for the preparation of a compound according to the present invention, a dibromofluorobenzene can be treated with a benzyl alcohol in the presence of an alkali metal hydride, typically sodium hydride, in a suitable aprotic solvent such as tetrahydrofuran. The product can be treated with a suitable malonic acid derivative, such as malonic acid tert-butyl ester ethyl ester in the presence of an alkali metal hydride, typically sodium hydride and a metal halide, typically a copper halide, preferably copper bromide. Further treatment in an acidic solvent such as acetic acid at elevated temperature provides a benzyloxy-bromophenylacetic acid ester. This can be coupled to a boronic acid under the variety of conditions known to those skilled in the art for such Suzuki coupling, typically using solvents such as 1,2-dimethoxyethane and water, an alkali metal carbonate such as potassium carbonate, and a palladium compound such as tetrakis(triphenylphosphine)palladium(0).

If required the compound can be alkylated by treatment in a suitable aprotic solvent such as tetrahydrofuran with a suitable base such as a metal dialkylamide, typically LDA, and the appropriate halide at a suitable temperature, typically −78° C.

Removal of the benzyl protecting group can be achieved under the variety of conditions known to those skilled in the art for such deprotections, typically using a palladium catalyst such as 10% palladium on charcoal in a suitable solvent, such as ethanol, and under an atmosphere of hydrogen.

The phenol can be converted to a biphenyl ether by a variety of methods known to those skilled in the art eg DA Evans et al Tetrahedron Lett. (1998), 39, 2937, Hosseinzadeh R et al Synlett (2005), 7, 1101. Typically the phenol is treated with a tertiary amine, such as triethylamine, a metal acetate, such as copper acetate, an aryl boronic acid and a suitable solvent such as dichloromethane in the presence of an agent such as 4A molecular sieves.

Conversion of the ester to the acid can be done using a base such as an alkali metal hydroxide, typically potassium hydroxide in the presence of water and other suitable solvents such as methanol.

In another embodiment, compounds where A is S can be prepared by the treatment of a dibromofluorobenzene with an aryl thiol in the presence of a suitable base such as potassium carbonate, in a suitable aprotic solvent such as N,N,dimethylformamide. The product can be treated with a suitable malonic acid derivative, such as malonic acid tert-butyl ester ethyl ester in the presence of an alkali metal hydride, typically sodium hydride and a metal halide, typically a copper halide, preferably copper bromide. Further treatment in an acidic solvent such as acetic acid at elevated temperature provides an arylthio-bromophenylacetic acid ester. This can be coupled to a boronic acid under the variety of conditions known to those skilled in the art for such Suzuki coupling, typically using solvents such as 1,2-dimethoxyethane and water, an alkali metal carbonate such as potassium carbonate, and a palladium compound such as tetrakis(triphenylphosphine)palladium(0).

If required the compound can be alkylated by treatment in a suitable aprotic solvent such as tetrahydrofuran with a suitable base such as a metal dialkylamide, typically LDA, and the appropriate halide at a suitable temperature, typically −78° C.

Conversion of the ester to the acid can be done using a base such as an alkali metal hydroxide, typically potassium hydroxide in the presence of water and other suitable solvents such as methanol.

In another embodiment for the preparation of a compound according to the present invention where A is NH, a dibromofluorobenzene can be treated with a benzyl alcohol in the presence of an alkali metal hydride, typically sodium hydride, in a suitable aprotic solvent such as tetrahydrofuran. The product can be treated with a suitable malonic acid derivative, such as malonic acid tert-butyl ester ethyl ester in the presence of an alkali metal hydride, typically sodium hydride and a metal halide, typically a copper halide, preferably copper bromide. Further treatment in an acidic solvent such as acetic acid at elevated temperature provides a benzyloxy-bromophenylacetic acid ester. This can be coupled to an aniline under the variety of conditions known to those skilled in the art for such Hartwig-Buchwald coupling, typically such as described by Hartwig JF in Modern Arene Chemistry, (2002) pp 107-168.

Removal of the benzyl etherprotecting group can be achieved under the variety of conditions known to those skilled in the art for such deprotections, typically using a palladium catalyst such as 10% palladium on charcoal in a suitable solvent, such as ethanol, and under an atmosphere of hydrogen.

The resultant hydroxycompound can be converted to a triflate using eg trifluoromethanesulphonic anhydride, an organic base such as pyridine and in a suitable solvent such as dichloromethane. This triflate can then be coupled to a boronic acid under the variety of conditions known to those skilled in the art for such Suzuki coupling, typically using solvents such as 1,2-dimethoxyethane and water, an alkali metal carbonate such as potassium carbonate, and a palladium compound such as bis(tri-tert-butylphosphine)palladium(0).

If required the product can be alkylated by treatment in a suitable aprotic solvent such as tetrahydrofuran with a suitable base such as a metal alkylamide, typically LDA, and the appropriate halide at a suitable temperature, typically −78° C.

Conversion of the ester to the acid can be done using a base such as an alkali metal hydroxide, typically sodium hydroxide in the presence of water and other suitable solvents such as ethanol.

When compounds of the invention are produced as racemates, these can be separated into their enantiomers by methods known to those skilled in the art, typically by using a chiral HPLC column.

Furthermore, the invention relates to a method for the preparation of a medicament comprising the steps of:
a) preparing a compound according to the invention
b) formulation of a medicament containing said compound.

The compounds according to the invention and their pharmaceutically acceptable salts, optionally in combination with other pharmaceutically active compounds are suitable to treat or prevent Alzheimer's disease or the symptons thereof. Such additional compounds include cognition-enhancing drugs such as acetylcholinesterase inhibitors (e.g. Donepezil, Tacrine, Galantamine, Rivastigmin), NMDA antagonists (e.g. Memantine) PDE4 inhibitors (e.g. Ariflo) or any other drug known to a person skilled in the art suitable to treat or prevent Alzheimer's disease. Such compounds also include cholesterol-lowering drugs such as statins (e.g. simvastatin). These compounds can be administered to animals, preferably to mammals, and in particular humans, as pharmaceuticals by themselves, in mixtures with one anther or in the form of pharmaceutical preparations.

Various delivery systems are known and can be used to administer a compound of the invention for the treatment of Alzheimer's disease or for the modulation of the γ-secretase activity, e.g. encapsulation in liposomes, microparticles, and microcapsules:

If not delivered directly to the central nervous system, preferably the brain, it is advantageous to select and/or modify methods of administration in such a way as to allow the pharmaceutical compound to cross the blood-brain barrier.

Methods of introduction include, but are not limited to, intradermal, intramuscular, intraperitoneal, intravenous, subcutaneous, intranasal, epidural, and oral routes.

The compounds may be administered by any convenient route, for example by infusion, by bolus injection, by absorption through epithelial or mucocutaneous linings and may be administered together with other biologically active agents.

Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g. by use of an inhaler or nebulizer, and formulation with an aerosolizing agent.

In another embodiment, the compound can be delivered in a vesicle, in particular a liposome (Langer (1990) Science 249, 1527.

In yet another embodiment, the compound can be delivered via a controlled release system. In one embodiment, a pump may be used (Sefton (1987) CRC Crit. Ref. Biomed. Eng. 14, 201; Buchwald et al. (1980) Surgery 88, 507; Saudek et al. (1989) N. Engl. J. Med. 321, 574). In another embodiment, polymeric materials can be used (Ranger and Peppas (1983) Macromol. Sci. Rev. Macromol. Chem. 23, 61; Levy et al. (1985) Science 228, 190; During et al. (1989) Ann. Neurol. 25, 351; Howard et al. (1989) J. Neurosurg. 71, 858). In yet another embodiment, a controlled release system can be placed in proximity of the therapeutic target, i.e., the brain, thus requiring only a fraction of the systemic dose (e.g. Goodson, 1984, In: Medical Applications of Controlled Release, supra, Vol. 2, 115). Other controlled release systems are discussed in the review by Langer (1990, Science 249, 1527).

In order to select an appropriate way of administration, the person skilled in the art will also consider routes of administration which have been selected for other known Anti-Alzheimer-drugs.

For example, Aricept/Donepezil and Cognex/Tacrine (all acetylcholinesterase-inhibitors) are being taken orally, Axura/Memantine (an NMDA-receptor antagonist) has been launched both as tablets/liquid and as an i.v.-solution.

Furthermore, the skilled person in the art will take into account the available data with respect to routes of administration of members of the NSAID-family in clinical trials and other studies investigating their effect on Alzheimer's disease.

In order to select the appropriate dosage, the person skilled in the art will choose a dosage which has been shown to be not toxic in preclinical and/or clinical studies and which can be in accordance with the values given beforehand, or which may deviate from these.

The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 mg/kg body weight to 1 mg/kg body weight. Effective doses may be extrapolated from dose-response curves derived from in vitro or animal model test systems.

An exemplary animal model is the transgenic mouse strain "Tg2576" containing an APP695-form with the double mutation KM670/671NL. For reference see e.g. patent U.S. Pat. No. 5,877,399 and Hsiao et al. (1996) Science 274, 99 and also Kawarabayahsi T (2001) J. Neurosci. 21, 372; Frautschy et al. (1998) Am. J. Pathol. 152, 307; Irizarry et al. (1997) J. Neuropathol. Exp. Neurol. 56, 965; Lehman et al. (2003) Neurobiol. Aging 24, 645. Substantial data from several studies are available to the skilled person in the art, which are instructive to the skilled person to select the appropriate dosage for the chosen therapeutic regimen.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Wherein the present invention is directed to co-therapy or combination therapy, comprising administration of one or more compound(s) "therapeutically effective amount" shall mean that amount of the combination of agents taken together so that the combined effect elicits the desired biological or medicinal response. Further, it will be recognized by one skilled in the art that in the case of co-therapy the amount of each component of the combination if used by itself may or may not be a therapeutically effective amount.

Numerous studies have been published in which the effects of molecules on the γ-secretase activity are described. Exemplary studies are Lim et al. (2001) Neurobiol. Aging 22, 983; Lim et al. (2000) J Neurosci. 20, 5709; Weggen et al. (2001) Nature 414, 212; Eriksen et al. (2003) J Clin Invest. 112, 440; Yan et al. (2003) J Neurosci. 23, 7504.

As used herein, unless otherwise noted, the term "isolated form" shall mean that the compound is present in a form which is separate from any solid mixture with another compound(s), solvent system or biological environment.

As used herein, unless otherwise noted, the term "substantially pure base" shall mean that the mole percent of impurities in the isolated base is less than about 5 mole percent, preferably less than about 2 mole percent, more preferably, less than about 0.5 mole percent, most preferably, less than about 0.1 mole percent.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent.

The term "pharmaceutically acceptable" means a non-toxic material that does not interfere with the effectiveness of the biological activity of the active ingredients. Such preparations may routinely contain pharmaceutically acceptable concentrations of salts, buffering agents, preservatives, compatible carriers and optionally other therapeutic agents.

General Synthesis Description

The following general description is for illustrative purposes only and is in no way meant to limit the invention.

The compound of Formula I wherein A, X, $R^1$, $R^2$, $R^3$, $R^4$, $R^9$, and $R^{10}$ are defined as in Formula I, and Y is $CO_2H$, may be obtained by hydrolysis of ester II under standard acidic or basic hydrolysis conditions, including reaction with NaOH, at room temperature, for several hours, in an appropriate solvent mixture, such as water, tetrahydrofuran (THF), and methanol. For illustrative purposes, ester II is shown with X as $CHR^5$, but those skilled in the art will recognize that ester hydrolysis will work for all X as defined in Formula I.

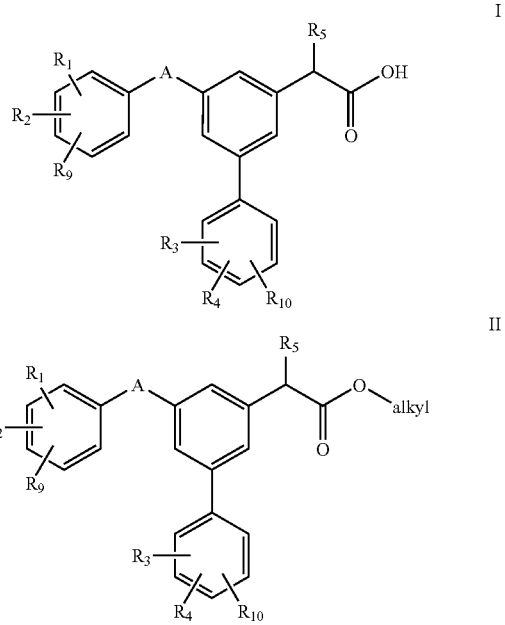

wherein:
for Ia and IIa, A is NH;
for Ib and IIb, A is O;
for Ic and IIc, A is S.

Compound IIa, where A is NH, may be obtained by coupling compound IIIa or IIIb with an aryl amine under typical Buckwald or Hartwig conditions, e.g. in toluene, dioxane or THF in the presence of potassium t-butoxide and a catalyst, e.g. palladium(II) acetate (Pd(OAc)$_2$) or Palladium(0) trans, trans-dibenzylideneacetone at elevated temperature (range from 80-180 degrees C.) or the reaction may be preformed with a microwave reactor. Compound IIb, where A is O, may be obtained from coupling phenol IIIc with an aryl boronic acid in dicholoromethane (DCM) in the presence of a base, (such as dimethylaminopyridine (DMAP), or triethylamine), molecular sieves and Cu(OAc)$_2$ at room temperature. in a similar condition as described in D. Evans, et.al. Tetrahedron Lettters (1980, 39(19), 2937-2940. Alternatively compounds IIb and IIc, where A is O, and S respectively, may be prepared from coupling reaction of IIIa or IIIb with aryl phenols or thiophenols. Compound IIb may also be prepared from IIIc by reacting with methanesulfonyl anhydride in DCM in the presence of triethylamine and then the resulting methane sulfonates can be condensed with phenols or thiophenols in the aprotic solvent in the presence bases, e.g. diisopropylethyl amine. Various reaction conditions for diaryl ether synthesis see the review article by Rok Frlan and Danijel Kikkelj (Synthesis 2006, No 14, pp 2271-2285). Compound IIb may also be prepared from IIIc by reacting with methanesulfonyl anhydride in DCM in the presence of triethylamine and then the resulting methane sulfonates can be condensed with phenols or thiophenols in the aprotic solvent in the presence bases, e.g. diisopropylethyl amine.

Compound IIIa may be obtained from the reaction of phenol IIIc with trifluoromethanesulfonic anhydride in DCM in the presence of an amine such as pyridine, or triethylamine at 0° C. Intermediate IIIb can be obtained from reactions of phenol IIIc with concentrated HCl, or HBr, or HI at elevated temperature (ranges from 25 to 120° C.). Alternatively, compound IIIb can be obtained under mild conditions by treatment of the corresponding triflate IIIc with pinacoborane in dioxane in the presence of triethylamine catalyzed with PdCl$_2$ to give an aryl pinacol boronate ester which is then treated with copper(II) halide in methanol-water procedure described by Nesmejanow et al. (Chem. Ber. 1960, 2729). The aforementioned pinacolboronate ester could also be reacted with NaI in aqueous THF in the presence of chloramines-T to give aryl iodide described by J. W. Huffman et. al. (Synthesis, 2005, 547).

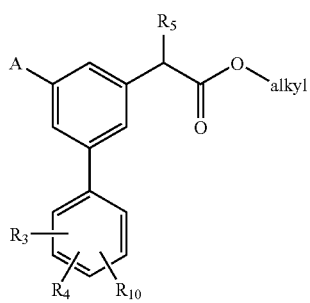

III wherein:
for IIIa, A is OTf;
for IIIb, A is Cl, Br, or I;
for IIIc, A is OH.

Compound IIIc may be prepared by debenzylation of compound IV by hydrogenation in alcohol, e.g. MeOH or EtOH in the presence of Pd—C. Debenzylation can also be achieved with other methods, such as BBr$_3$ in DCM, NaCN in DMSO/120-200° C. or LiCN in DMF/120-200° C.

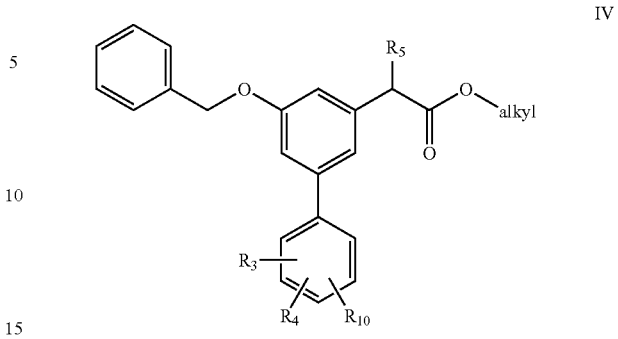

IV

Compound IV may be prepared from alkylation of compound V with either an alkyl or alkenyl halide. Treatment of compound V in THF or another aprotic solvent with a base, e.g. lithium bis(trismethylsilyl)amide, sodium bis(trismethylsilyl)amide, or lithium diisopropylamide at −78° C., followed by the addition of an electrophile, e.g. an alkyl or alkenyl halide, yields alkylated compound IV.

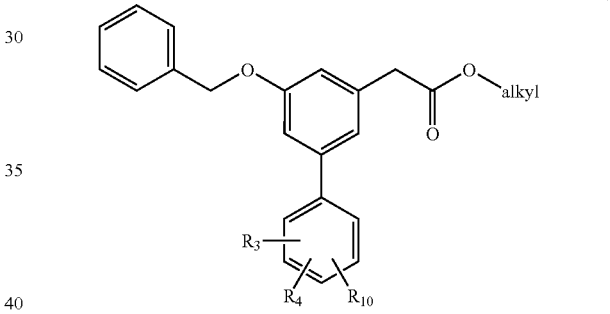

V

Compound V may be prepared from compound VI through a coupling reaction with an arylboronic acid under Suzuki conditions of aqueous sodium carbonate in DME in the presence of Pd(PPh$_3$)$_4$. Similarly, the triflates can be converted to boronate esters under the conditions described above and then can be coupled with aryl bromides or aryl chlorides to give compound V.

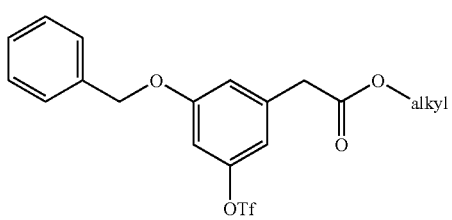

VI

Intermediate compound VI may be prepared from compound VII with trifluoromethanesulfonic anhydride in DCM in the presence of one equivalent of pyridine at 0° C.

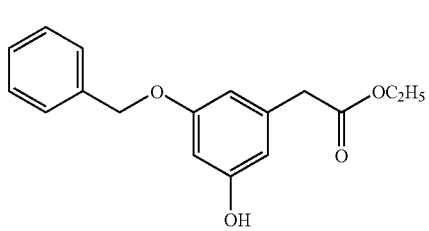

VII

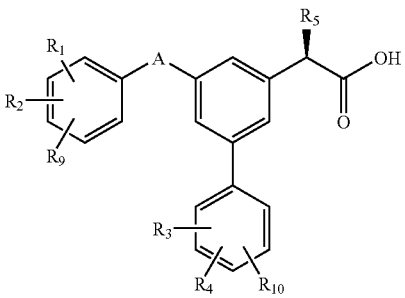

Ia

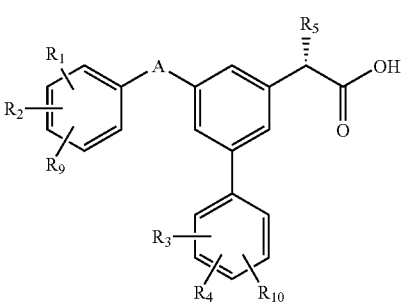

Ib wherein
A is NH, O, or S

Intermediate compound VII can be prepared from mono-debenzylation of compound VIII. Selective mono-debenzylation of compound VIII can be achieved by treatment with 1.1 equivalents of base, e.g. sodium hydroxide or potassium hydroxide, in ethanol or methanol solution in the presence of Pd—C catalyst under hydrogen atmosphere in a Parr shaker.

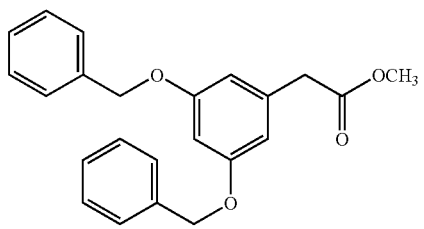

VIII

Intermediate VIII can be easily prepared from reaction of 3,5-dihydroxyphenyl acetic acid methyl ester (commercially available) with benzyl bromide and potassium carbonate in DMF at room temperature.

Compound I has a chiral center α to the carboxylic group, and can exist as one of two enantiomers (or a mixture thereof, wherein an enantiomeric excess may or may not be present). The enantiomers Ia (R enantiomer) and Ib (S enantiomer) are shown. The pure enantiomers Ia and Ib may be obtained by chiral separation using a chiral column. The enantiomers Ia and Ib may also be separated by resolutions through forming chiral amine salts by fractional recrystallizations. The enantiomers Ia and Ib also may be obtained from kinectic resolution of the racemate of corresponding esters using lipase enzymes, e.g. AmanoAk, Amano lipase PS, Amano lipaseA, Amano lipase M, Amano lipase F-15 Amano lipase G (from Biocatalytics Inc) in aqueous organic solvents, e.g. aqueous DMF, DMSO, t-butyl-ethyl ether or triton X-100 aqueous solutions.

Both enantiomers of compound I may be prepared from chiral syntheses. Compounds Ia and Ib may be obtained from the removal of the chiral auxiliary groups from compounds IXa and IXb respectively with lithium hydroxide in aqueous THF in the presence of hydrogen peroxide.

Compounds IXa and IXb, where A is NH, may be obtained by coupling compounds Xa and Xb respectively with aryl amines under typical Buckwald or Hartwig conditions, e.g. in toluene, dioxane, or THF in the presence of potassium t-butoxide and catalytic $Pd(OAc)_2$ or $Pd(dba)_2$. Compounds IXa and IXb, where A is O, may be obtained from reaction of compounds XIa and XIb respectively with aryl boronic acids in DCM and DMAP in presence of $Pd(OAc)_2$ and molecular sieves. Compounds IXa and IXb, where A is O or S, also may be obtained from Xa and Xb respectively with phenols or thiophenols in DCM and DMAP in presence of $Pd(OAc)_2$ and molecular sieves. Compounds Xa and Xb may be obtained from reaction of phenols XIa and XIb with trifluoromethanesulfonic anhydride in DCM in the presence of amines such as pyridine, or triethylamine at 0° C.

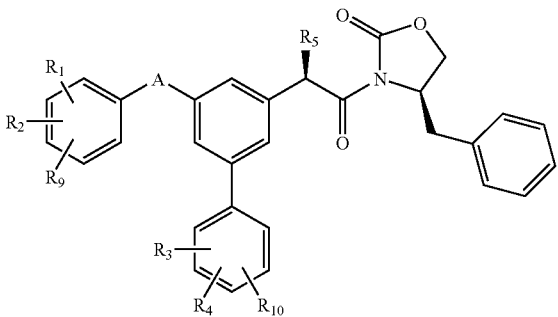

IXa

IXb

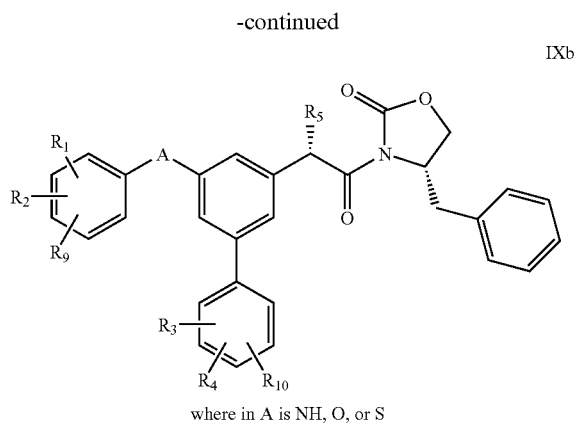

where in A is NH, O, or S

Xa

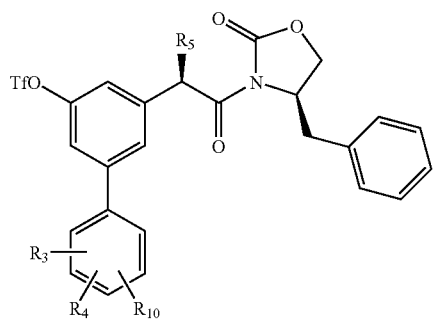

Xb

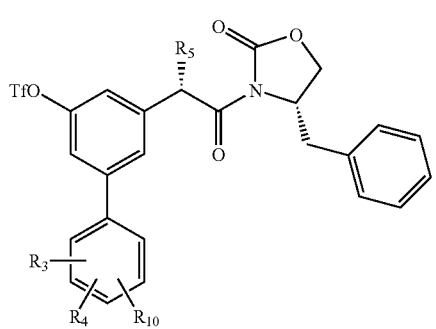

XIa

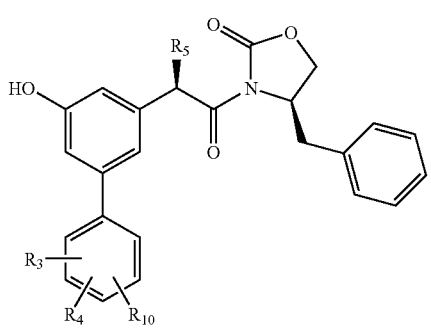

XIb

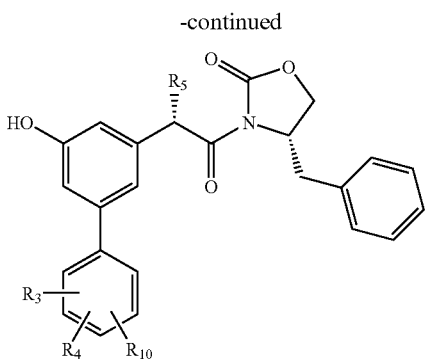

Compounds XIa and XIb may be prepared from debenzylation of compounds XIIa and XIIb respectively by hydrogenation in an alcohol solvent, e.g. MeOH or EtOH, in the presence of Pd—C.

XIIa

XIIb

Compounds XIIa and XIIb may be prepared from the alkylation of compounds XIIIa and XIIIb respectively with an alkyl halide or alkenyl halide. Treatment of compounds XIIIa and XIIIb in THF or other aprotic solvents with bases, e.g. lithium bis(trismethylsilyl) amide, sodium bis(trismethylsilyl)amide, or lithium diisopropylamide at −78° C., followed by the addition of electrophiles, e.g. alkyl halides or alkenyl halides, gives alkylated compounds XIIa and XIIb respectively.

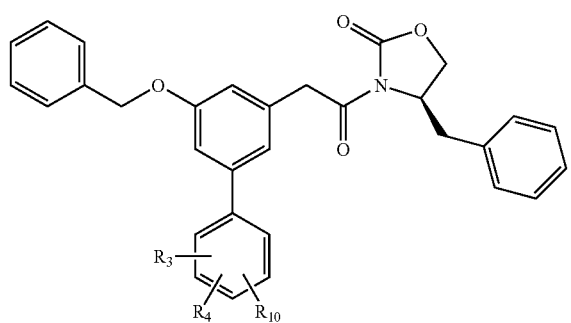

XIIIa

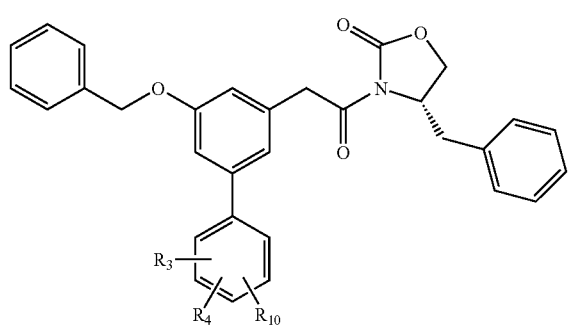

XIIIb

Compounds XIIIa and XIIIb may be prepared from the common intermediate XIV by coupling with either R-isomer of 4-benzyl-oxazolidin-one XVa or S-isomer of 4-benzyl-oxazolidin-one XVb by Evans's procedures. Intermediate XIV may be reacted with pivaloyl chloride, oxalyl chloride or isopropyl chloroformate in THF in the presence of a base, e.g. triethylamine or N-methylmorpholine, to mixed anhydrides or acid chlorides which then were reacted with the lithium salt of XVa or XVb in THF.

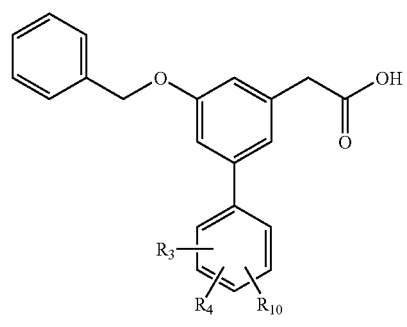

XIV

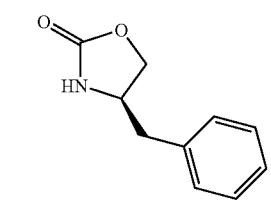

XVa

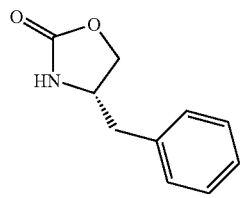

XVb

Intermediate compound XIV may be obtained from ester hydrolysis of compound V with bases in aqueous alcohol solution, e.g. LiOH or NaOH in aqueous methanol solution.

Synthetic Procedures

All reactions were carried out under inert atmosphere unless otherwise stated. NMR spectra were obtained on a Bruker dpx400. LCMS was carried out on an Agilent 1100 using a ZORBAX® SB-C18, 4.6×75 mm, 3.5 micron column for method A. Column flow was 1 ml/min and solvents used were water and acetonitrile (0.1% TFA) with an injection volume of 10 ul. Wavelengths were 254 and 210 nm. Methods are described below:

| Method | Flow Rate | Solvent |
|---|---|---|
| A | 1 ml/min | 0-1.5-95% MeCN |
|   |   | 1.5-6 min 95% |
|   |   | 4.5-5 min 95%-5% MeCN |

Abbreviations

| | |
|---|---|
| Ac | Acetyl |
| d | Doublet |
| DCM | Dichloromethane |
| DME | 1,2-dimethoxyethane |
| DMF | N,N-dimethylformamide |
| DMSO | Dimethyl sulfoxide |
| e.e. | enantiomeric excess |
| Eq | Equivalents |
| Et | Ethyl |
| EtOAc | ethyl acetate |
| g | Gram |
| h | Hour |
| HPLC | high pressure liquid chromatography |
| $K_2CO_3$ | Potassium carbonate |
| l | Litre |
| LCMS | liquid chromatography - mass spectrometry |
| LDA | lithium diisopropylamide |
| M | Molar |
| m | Multiplet |
| Me | Methyl |
| min | Minute |
| mol | Mole |
| NMR | nuclear magnetic resonance |
| q | Quartet |
| RT | Retention time |
| s | Singlet |
| sat | Saturated |
| t | Triplet |
| TFA | Trifluoroacetic acid |
| THF | Tetrahydrofuran |

EXAMPLES

Example (i)

Preparation of 2-(5-(4-fluorophenoxy)-4'-trifluoromethyl-biphenyl-3-yl)-pentanoic acid

Preparation of 1-Benzyloxy-3,5-dibromobenzene

Benzylalcohol (9.7 mLl, 94 mmol) was added dropwise to a suspension of NaH (4.0 g of a 60% suspension in mineral oil, 100 mmol) in THF (150 mL) at room temperature and the mixture was stirred at room temperature for 1 hour before 1,3-dibromo-5-fluorobenzene (15.9 g, 62.5 mmol) was added. The reaction was stirred at room temperature for 12 hours. Water was added carefully and the THF was evaporated under reduced pressure. The residue was extracted with iso-hexane (×3) and the combined organic extracts were washed with NaOH solution (1 M aq.), water, brine, dried ($MgSO_4$), filtered and concentrated under reduced pressure. The residue was purified by flash column chromatography (EtOAc:petroleum ether) to give 1-benzyloxy-3,5-dibromobenzene (14.7 g, 65 mmol) as a colourless liquid in 69% yield. $^1$H NMR ($CDCl_3$) δ 7.45-7.33 (m, 5H), 7.30-7.28 (m, 1H), 7.10-7.08 (m, 2H), 5.02 (s, 2H).

Preparation of (3-Benzyloxy-5-bromo-phenyl)-acetic acid ethyl ester

Malonic acid tert-butyl ester ethyl ester (10.2 mL, 53.8 mmol) was added dropwise to a suspension of NaH (2.2 g of a 60% suspension in mineral oil, 53.8 mmol) in dioxane (200 mL) at room temperature and the mixture was stirred at this temperature for 1 hour before CuBr (7.7 g, 53.8 mmol) and 1-benzyloxy-3,5-dibromobenzene (9.2 g, 26.9 mmol) were added. The reaction mixture was heated to reflux for 5 h. HCl solution (1M aq, 100 mL) was carefully added and the mixture was extracted with iso-hexane (×3). The combined organic extracts were washed with HCl solution (1 M aq), water, brine, dried ($MgSO_4$), filtered and concentrated under reduced pressure. The residue was purified by flash column chromatography (EtOAc:petroleum ether) to give, in order of elution, recovered 1-benzyloxy-3,5-dibromobenzene (3.2 g, 9.4 mmol) in 35% yield and 2-(3-benzyloxy-5-bromo-phenyl)-malonic acid tert-butyl ester ethyl ester (7.2 g, contains 1.4 equivalent malonic acid tert-butyl ester ethyl ester, 10 mmol) as a colourless liquid in 37% yield. 2-(3-Benzyloxy-5-bromophenyl)malonic acid tert-butyl ester ethyl ester (7.2 g, contains 1.4 equivalent malonic acid tert-butyl ester ethyl ester, 10 mmol) was dissolved in glacial AcOH (50 mL) and heated to reflux for 12 hours. The AcOH was removed under reduced pressure. The residue was poured into $Na_2CO_3$ solution (sat. aq.) and the mixture was extracted with EtOAc (×3). The combined organic extracts were washed with water, brine, dried ($MgSO_4$), filtered and concentrated under reduced pressure to give (3-benzyloxy-5-bromo-phenyl-)acetic acid ethyl ester (6.8 g, 9.7 mmol) as a yellow liquid in 97% yield. $^1$H NMR ($CDCl_3$) δ 7.44-7.30 (m, 5H), 7.07-7.03 (m, 2H), 6.87-6.84 (m, 1H), 5.03 (s, 2H), 4.15 (q, 2H), 3.54 (s, 2H), 1.26 (t, 3H).

Preparation of (5-Benzyloxy-4'-trifluoromethyl-biphenyl-3-yl)-acetic acid ethyl ester (3-Benzyloxy-5-bromo-phenyl)-acetic acid ethyl ester (2.50 g, 7.2 mmol) was added to a solution of 4-(trifluoromethyl)phenyl boronic acid (1.5 g, 8.0 mmol) and $K_2CO_3$ (14.4 mmol, 2 M aq.) in DME (25 mL). Nitrogen was bubbled through the reaction mixture for 10 minutes before addition of tetrakis(triphenylphosphine)palladium(0) (10% wt) and the resultant mixture was heated to 80° C. for 4 hours under inert atmosphere. The reaction mixture was diluted with water and extracted with EtOAc (×3). The combined organic extracts were washed with sat. $Na_2CO_3$, brine, dried ($MgSO_4$), filtered and concentrated under reduced pressure. The residue was purified by flash column chromatography (EtOAc:petroleum ether) to give (5-benzyloxy-4'trifluoromethyl-biphenyl-3-yl)-acetic acid ethyl ester (2.2 g) as a colourless gum in 74% yield. $^1$H NMR ($CDCl_3$) δ 7.59-7.54 (m, 2H), 7.48-7.30 (m, 8H), 7.13-7.11 (m, 2H), 6.94-6.91 (m, 1H), 5.12 (s, 2H), 4.16 (q, 2H), 3.64 (s, 2H), 1.27 (t, 3H).

Preparation of 2-(5-Benzyloxy-4'-trifluoromethyl-biphenyl-3-yl)-pentanoic acid ethyl ester A solution of LDA (4.5 mL of 1.8 M in THF, 8 mmol) was added dropwise to a stirred solution of (5-Benzyloxy-4'-trifluoromethyl-biphenyl-3-yl)-acetic acid ethyl ester (3 g, 7.3 mmol) in THF (50 mL) at −78° C. The reaction mixture was stirred for 30 minutes at −78° C. before iodopropane (0.85 mL, 8.7 mmol) was added dropwise. The reaction mixture was allowed to warm to room temperature overnight. A saturated aqueous solution of ammonium chloride (10 mL) was carefully added and the residue was partitioned between EtOAc and water. The aqueous layers were extracted with EtOAc (×3). The combined organic layers were washed with water, brine, dried ($MgSO_4$), filtered and concentrated under reduced pressure. The residue was purified by flash column chromatography (EtOAc:petroleum ether) to give 2-(5-Benzyloxy-4'-trifluoromethyl-biphenyl-3-yl)-pentanoic acid ethyl ester (2.2 g) as an oil in 66% yield.

Preparation of 2-(5-(4-fluorophenoxy)-4'-trifluoromethyl-biphenyl-3-yl)-pentanoic acid 2-(5-Benzyloxy-4'-trifluoromethyl-biphenyl-3-yl)-pentanoic acid ethyl ester (1.1 g, 2.4 mmol) was dissolved in EtOH (10 mL) and stirred with 10% Pd/C (116 mg) under an atmosphere of hydrogen. After 19 h, the mixture was filtered through Celite and concentrated in vacuo to afford 2-(5-hydroxy-4'-trifluoromethyl-biphenyl-3-yl)-pentanoic acid ethyl ester (0.85 g) as a colourless oil.

Triethylamine (100 µL, 0.72 mmol) was added to a stirred mixture of 2-(5-hydroxy-4'-trifluoromethyl-biphenyl-3-yl)-pentanoic acid ethyl ester (90 mg, 0.25 mmol), $Cu(OAc)_2$ (68 mg, 0.38 mmol), 4-fluorophenylboronic acid (70 mg, 0.57 mmol), 4 Å molecular sieves (25 mg, powdered) and DCM (2 mL) at room temperature open to the air. After 24 h, the reaction mixture was loaded onto silica and purified (0-10% ethyl acetate in petrol) to give 2-(5-(4-fluorophenoxy)-4'-trifluoromethyl-biphenyl-3-yl)-pentanoic acid ethyl ester (67 mg) as a colourless oil.

The ester was dissolved in THF (1.2 mL) and treated with a 1M solution of KOH in 6:1 MeOH/water (0.3 mL, 2 eq). After 65 h, the mixture was diluted with water (5 mL) then acidified with 1M HCl(aq). The mixture was extracted with ethyl acetate (2×5 mL), then the combined organic layer was washed with brine; dried ($MgSO_4$) and concentrated in vacuo to afford 2-(5-(4-fluorophenoxy)-4'-trifluoromethyl-biphenyl-3-yl)-pentanoic acid (57 mg, 90%) as a pale yellow gum. LCMS Method A—3.65 min.

Example (ii)

2-(5-(phenoxy)-4'-trifluoromethyl-biphenyl-3-yl)-pentanoic acid

In an analogous fashion to Example 1 using phenylboronic acid in place of 4-fluorophenylboronic acid was prepared 2-(5-(phenoxy)-4'-trifluoromethyl-biphenyl-3-yl)-pentanoic acid LCMS Method A—3.69 min.

Example 1

2-[5-(3,5-Difluoro-phenylamino)-4'-trifluoromethyl-biphenyl-3-yl]-4-methyl-pentanoic acid

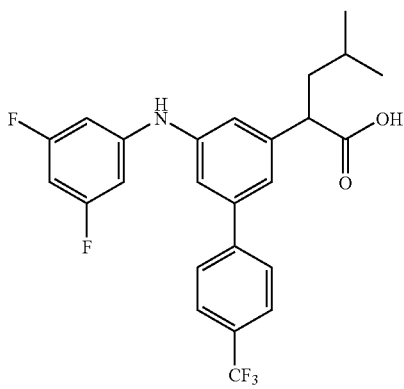

a) (3,5-Bis-benzyloxy-phenyl)-acetic acid methyl ester

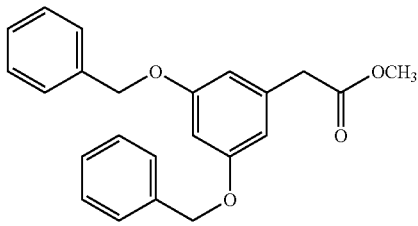

A mixture of (3,5-dihydroxy-phenyl)-acetic acid methyl ester (from Aldrich, 70 g, 0.385 mole), benzylbromide (137 mL, 1.16 mole), potassium carbonate (160 g, 1.16 mole) and DMF (1.5 L) under $N_2$ was mechanically stirred at room temperature overnight. The resulting reaction mixture was poured into a mixture of 1.5 L of ice-water with stirring. The precipitate was obtained by filtration and washed with heptane successively to remove benzyl bromide to give the title compounds (123.7 g) as a brown solid which was air dried for the next reaction. $^1$H-NMR (CDCl$_3$): δ 3.60 (s, 2H), 3.71 (s, 3H), 5.05 (s, 4H), 6.60 (s, 3H), 7.35-7.50 (m, 10H); Calcd for C23H22O4 (M+H) 363.15, Found 363.

b) 3-Benzyloxy-5-hydroxy-phenyl)-acetic acid ethyl ester

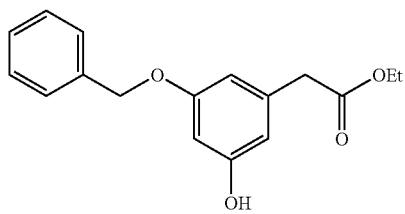

A solution of 50 grams (1.38 moles) of 3,5-Bis-benzyloxy-phenyl)-acetic acid methyl ester and NaOH (6.6 g, 1.65 moles) in 1 L of EtOH in the presence of 10% of Pd—C was hydrogenated in a Parr shaker until one equivalent of hydrogen was consumed. The mixture was acidified with con HCl and then the catalyst and solvent were removed to give an oil residue. The crude product was purified by ISCO silica gel column chromatography (ISCO) using EtOAC-heptane as eluents (gradient from 10% to 75% of EtOAc) to give 25 grams (65% yield) the title compound (1b). $^1$H-NMR (CDCl$_3$): δ 1.15-1.20 (t, 3H), 3.4 (s, 2H), 4.05-4.1 (q, 2H), 4.9 (s, 2H), 5.5 (s, 1H), 6.4 (s, 2H), 6.5 (s, 1H), 7.20-7.35 (m, 5H); Calcd for C17H18O4 (M+H) 287.3, Found 287.

c) (3-Benzyloxy-5-trifluoromethanesulfonyloxy-phenyl)-acetic acid ethyl ester

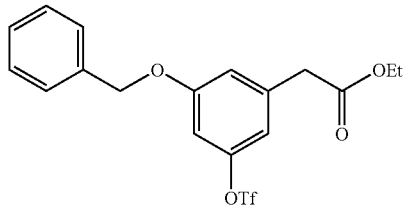

To a solution of 3-(benzyloxy-5-hydroxy-phenyl)-acetic acid ethyl ester (74.4 g, 0.26 mol) in dichloromethane (700 mL) was added pyridine (62.5 mL, 0.78 mol). The mixture was cooled to 0° C. To this cold solution was added trifluoromethanesulfonic anhydride (65.6 mL, 0.39 mol), over 1.5 h, maintaining the internal temperature below 5° C. and stirred for further 0.5 h at 0° C. This reaction mixture was poured to a mixture of 1 N HCl (420 mL), and wet-ice (105 g) and stirred for 0.5 h. The aqueous layer was extracted with dichloromethane (2×100 mL). Combined fractions were washed with water (2×100 mL), saturated aqueous NaHCO$_3$ solution (2×100 mL), and brine (2×100 mL). The organics were dried (MgSO$_4$) and concentrated in vacuo to receive a reddish liquid (108 g) which was carried on to the next step without further purification. Calcd for C18H17F3O6S (M+H) 419.07, Found 419.1.

d) (5-Benzyloxy-4'-trifluoromethyl-biphenyl-3-yl)-acetic acid ethyl ester

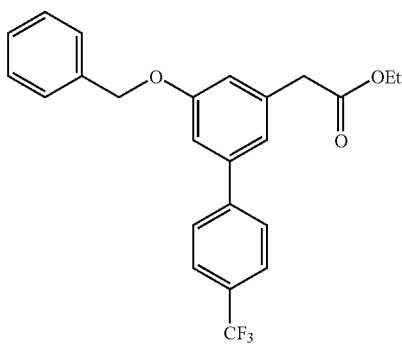

A mixture of (3-benzyloxy-5-trifluoromethanesulfonyloxy-phenyl)-acetic acid ethyl ester (108 g, 0.26 mol), 4-(trifluoromethyl)phenylboronic acid (55.6 g, 0.29 mol), 1,2-dimethoxyethane (1.1 L) and aqueous $Na_2CO_3$ (2 M, 129 mL, 0.26 mol) was mechanically stirred while purging $N_2$ at room temperature for 10 min. To this system was added $Pd(Ph_3)_4$ (480 mg, 0.42 mmol) and heated to reflux (95° C.) for 2.5 h. The red-brown mixture was diluted with EtOAc (0.5 L) and washed with saturated aqueous $NaHCO_3$ solution (3×200 mL) and brine (2×200 mL). The organic fraction was dried ($Na_2SO_4$) and concentrated in vacuo. The crude mixture was purified by ISCO column chromatography to obtain (5-benzyloxy-4'-trifluoromethyl-biphenyl-3-yl)-acetic acid ethyl ester (107 g, 100%).

$^1$H-NMR (CDCl$_3$): δ 1.26 (t, 3H), 3.66 (s, 2H), 4.17 (q, 2H), 5.12 (s, 2H), 6.99 (s, 1H), 7.12 (s, 2H), 7.34-7.49 (m, 5H), 7.67 (s, 4H); Calcd for C24H21F3O3 (M+H) 415.14, Found 415.2.

e) 2-(5-Benzyloxy-4'-trifluoromethyl-biphenyl-3-yl)-4-methyl-pent-4-enoic acid ethyl ester

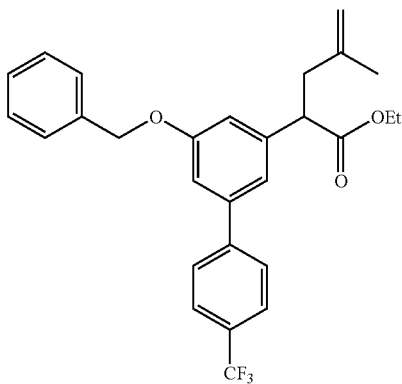

To a solution of compound 1d (4.9 g, 11.8 mmole) in THF (50 mL) at −78° C. was added Li[N(SiMe$_3$)$_2$] (1N in THF, 14.2 mL, 14.2 mmol) dropwise. The reaction mixture was stirred for 1 h at −78° C. and then 3-bromo-2-methyl-propene (1.25 mL, 12.4 mmole) was added dropwise. The solution was slowly warmed up to −35° C. and stirred at −35° C. for 0.5 h. The reaction was quenched with NH$_4$Cl saturated solution and extracted with EtOAc. The organic extracts was dried (Na$_2$SO$_4$), concentrated and purified by column chromatography give compound 1e (5.1 g, 92%) as a clear oil; $^1$H NMR (400 MHz, CHLOROFORM-D) δ ppm 1.19-1.29 (m, 3H), 1.74 (s, 3H), 2.47 (m, 1H), 2.85 (m, 1H), 3.83 (m, 1H), 4.11 (m, 2H), 4.72 (s, 1H), 4.77 (s, 1H), 5.12 (s, 2H), 7.03 (s, 1H), 7.10 (s, 1H), 7.15 (s, 1H), 7.35-7.48 (m, 5H), 7.67 (s, 4H); Calcd for C28H27F3O3 (M+H) 469.19, Found 469.

f) 2-(5-Hydroxy-4'-trifluoromethyl-biphenyl-3-yl)-4-methyl-pentanoic acid ethyl ester

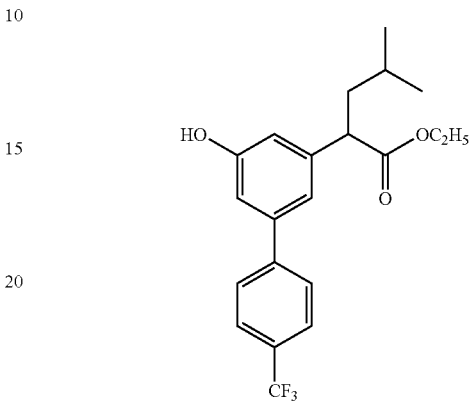

A mixture of compound 1e (5.1 g, 10.9 mmole), 10% Pd/C (500 mg) in EtOH (50 mL) was hydrogenated under H$_2$ (40 psi) in par-shaker for 20 h. The resulting reaction mixture was filtered through celite and the filtrate was concentrated to give compound 1f (4.2 g, 100%) as a clear oil; $^1$H NMR (300 MHz, CHLOROFORM-D) δ ppm 0.92 (d, J=6.6 Hz, 6H), 1.25 (m, 3H), 1.49-1.61 (m, 1H), 1.65-1.70 (m, 1H), 1.95-2.05 (m, 1H), 3.67 (t, J=7.7 Hz, 1H), 4.10-4.29 (m, 2H), 6.91 (s, 1H), 6.97 (t, J=2.0 Hz, 1H), 7.08 (s, 1H), 7.65 (s, 4H); Calcd for C21H23F3O3 (M+H) 381.16, Found 381.

g) 4-Methyl-2-(5-trifluoromethanesulfonyloxy-4'-trifluoromethyl-biphenyl-3-yl)-pentanoic acid ethyl ester

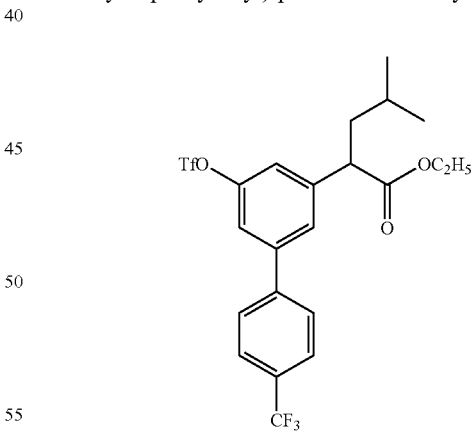

To a solution of compound 1f (2.8 g, 7.36 mmol) and N-phenyl-bis-(trifluoromethanesulfonimide) (3.16 g, 8.83 mmol) in THF (30 mL) under N$_2$ was added Et$_3$N (2.05 mL, 14.7 mmol). The reaction mixture was heated refluxing over night. After cooling to room temperature, the solution was concentrated and purified by column chromatography to give compound 1g (3.7 g, 98%) as a colorless thick oil; $^1$H NMR (400 MHz, CHLOROFORM-D) δ ppm 0.94 (dd, J=6.60, 1.47 Hz, 6H), 1.22-1.28 (m, 3H), 1.46-1.52 (m, 1H), 1.69 (ddd, J=13.82, 7.09, 6.97 Hz, 1H), 1.98-2.06 (m, 1H), 3.75 (t, J=7.83 Hz, 1H), 4.10-4.21 (m, 2H), 7.31 (s, 1H), 7.38 (s, 1H), 7.57 (s, 1H), 7.65-7.75 (m, 4H); Calcd for C22H22F6O5S (M+H) 513.11, Found 513.

h) 2-[5-(3,5-Difluoro-phenylamino)-4'-trifluoromethyl-biphenyl-3-yl]-4-methyl-pentanoic acid A mixture of compound 1g (50 mg, 0.098 mmol), 3,5-difluoro-aniline (20 mg, 0.156 mmol), Pd(OAc)$_2$ (6.6 mg, 0.029 mmol), racemic-2-(di-t-butylphosphino)-1,1'-binaphthyl (35 mg, 0.088 mmol) and sodium tert-butoxide (NaOt-Bu) (11.3 mg, 0.12 mmol) in toluene (1.5 mL) was heated at 85° C. for 17 h. After cooling to room temperature, the solution was partitioned between EtOAc and H$_2$O. The organic layer was dried (Na$_2$SO$_4$), concentrated and purified by column chromatography to give an ethyl ester intermediate. A mixture of the above intermediate and NaOH (2N in H$_2$O, 0.147 mL, 0.294 mmol) in THF-MeOH (0.6 mL-0.6 mL) was stirred for 18 h and concentrated. CH$_2$Cl$_2$ and water were added, and the mixture was acidified with 1N HCl. The organic phase was separated and the aqueous phase was extracted with CH$_2$Cl$_2$. The combined organic layers were dried, concentrated, and purified by column chromatography to give 38 mg (84%, 2 steps) of the title compound as a white solid; $^1$H NMR (400 MHz, CHLOROFORM-D) δ ppm 0.91-1.00 (m, 6H), 1.51-1.62 (m, 1H), 1.70-1.80 (m, 1H), 1.99 (dd, J=7.83, 5.87 Hz, 1H), 3.71 (t, J=7.70 Hz, 1H), 6.01 (brs, 1H), 6.30-6.40 (m, 1H), 6.50-6.60 (m, 2H), 7.13 (d, J=1.71 Hz, 1H), 7.18-7.29 (m, 2H), 7.62-7.72 (m, 4H); Calcd for C25H22F5NO2 (M+H) 464.16, Found 464.

Example 2

2-[5-(2,4-Difluoro-phenylamino)-4'-trifluoromethyl-biphenyl-3-yl]-4-methyl-pentanoic acid

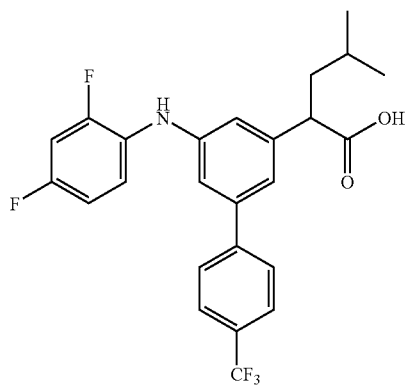

The title compound was prepared from 2,4-difluoro-aniline and compound 1g under the condition described in Example 1; $^1$H NMR (400 MHz, CHLOROFORM-D) δ ppm 0.88-0.99 (m, 6H), 1.56 (dt, J=13.39, 6.63 Hz, 1H), 1.72 (ddd, J=13.69, 7.21, 6.97 Hz, 1H), 1.94-2.06 (m, 1H), 3.69 (t, J=7.70 Hz, 1H), 5.70 (brs, 1H), 6.78-6.85 (m, 1H), 6.90 (ddd, J=10.94, 8.38, 2.93 Hz, 1H), 7.00 (s, 1H), 7.04-7.14 (m, 2H), 7.24-7.33 (m, 1H), 7.64 (q, J=8.31 Hz, 4H); Calcd for C25H22F5O2 (M+H) 464.16, Found 464.

Example 3

2-[5-(3,5-Bis-trifluoromethyl-phenylamino)-4'-trifluoromethyl-biphenyl-3-yl]-4-methyl-pentanoic acid

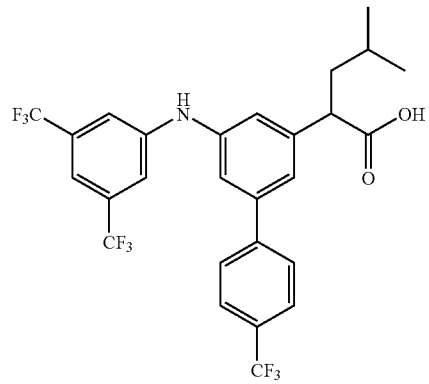

The title compound was prepared from 3,4-bis-trifluoromethyl-aniline and compound 1g under the condition described in Example 1; $^1$H NMR (400 MHz, CHLOROFORM-D) δ ppm 0.88-1.00 (m, 6H), 1.56 (ddd, J=13.33, 6.85, 6.72 Hz, 1H), 1.71-1.81 (m, 1H), 1.95-2.06 (m, 1H), 3.70-3.79 (m, 1H), 6.14 (s, 1H), 7.21 (s, 2H), 7.25 (d, J=4.89 Hz, 1H), 7.36 (s, 1H), 7.43 (s, 2H), 7.62-7.72 (m, 4H); Calcd for C27H22F9NO2 (M+H) 564.15, Found 564.

Example 4

2-[5-(4-Isopropyl-phenylamino)-4'-trifluoromethyl-biphenyl-3-yl]-4-methyl-pentanoic acid

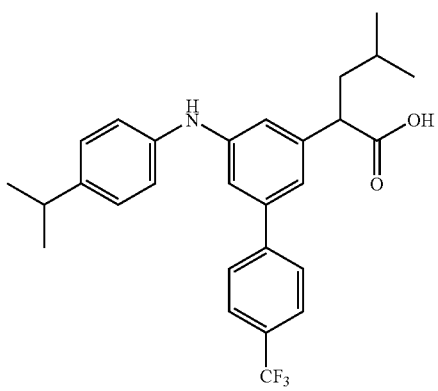

The title compound was prepared from 4-isopropyl-aniline and compound 1g under the condition described in Example 1; $^1$H NMR (400 MHz, CHLOROFORM-D) δ ppm 0.87-0.98 (m, 6H), 1.20-1.31 (m, 6H), 1.52-1.63 (m, 1H), 1.72 (ddd, J=13.69, 7.21, 6.97 Hz, 1H), 1.94-2.05 (m, 1H), 2.88 (dt, J=13.69, 6.85 Hz, 1H), 3.67 (t, J=7.70 Hz, 1H), 6.99-7.10 (m, 4H), 7.11-7.20 (m, 3H), 7.59-7.69 (m, 4H); Calcd for C28H30F3NO2 (M+H) 470.22, Found 470.

Example 5

2-[5-(4-Chloro-phenylamino)-4'-trifluoromethyl-biphenyl-3-yl]-4-methyl-pentanoic acid

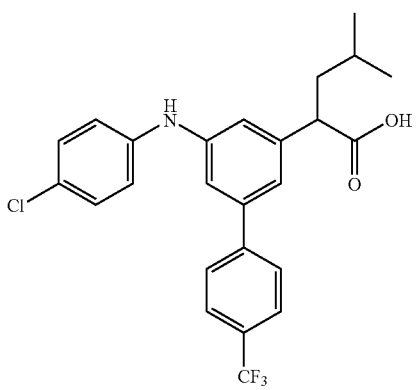

The title compound was prepared from 4-chloro-aniline and 1 g under the condition described in Example 1; $^1$H NMR (400 MHz, CHLOROFORM-D) δ ppm 0.89-0.98 (m, 6H), 1.56 (ddd, J=13.33, 6.85, 6.72 Hz, 1H), 1.72 (ddd, J=13.69, 7.21, 6.97 Hz, 1H), 1.94-2.06 (m, 1H), 3.68 (t, J=7.70 Hz, 1H), 6.98-7.06 (m, 3H), 7.09 (s, 1H), 7.14 (s, 1H), 7.20-7.31 (m, 2H), 7.64 (q, J=8.56 Hz, 4H); Calcd for C25H23ClF3NO2 (M+H) 462.14, Found 462.

Example 6

2-[5-(4-Fluoro-phenylamino)-4'-trifluoromethyl-biphenyl-3-yl]-4-methyl-pentanoic acid

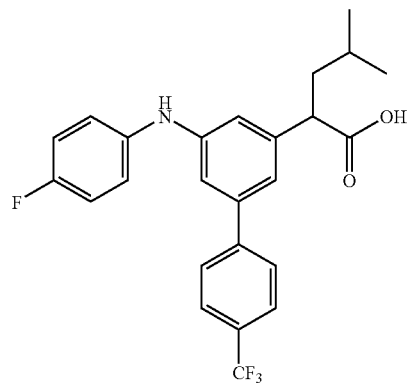

The title compound was prepared from 4-fluoro-aniline and 1 g under the condition described in Example 1; $^1$H NMR (400 MHz, CHLOROFORM-D) δ ppm 0.93 (dd, J=6.60, 1.22 Hz, 6H), 1.51-1.62 (m, 1H), 1.71 (ddd, J=13.82, 7.09, 6.97 Hz, 1H), 1.97 (ddd, J=13.57, 7.70, 7.58 Hz, 1H), 3.67 (t, J=7.70 Hz, 1H), 6.95-6.97 (m, 1H), 6.99-7.09 (m, 6H), 7.63 (q, J=8.56 Hz, 4H); Calcd for C25H23F4NO2 (M+H) 446.17, Found 446.

Example 7

2-[5-(3,5-Dichloro-phenylamino)-4'-trifluoromethyl-biphenyl-3-yl]-4-methyl-pentanoic acid

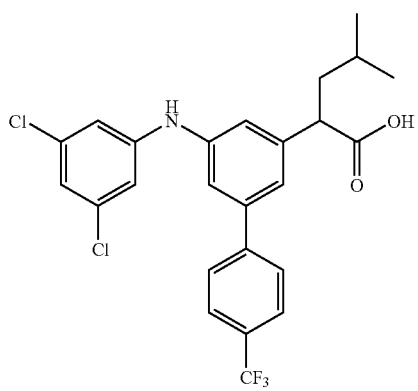

The title compound was prepared from 3,5-dichloro-aniline and compound 1g under the condition described in Example 1; $^1$H NMR (400 MHz, CHLOROFORM-D) δ ppm 0.90-1.00 (m, 6H), 1.55 (ddd, J=13.33, 6.85, 6.72 Hz, 1H), 1.71-1.81 (m, 1H), 1.93-2.05 (m, 1H), 3.71 (t, J=7.70 Hz, 1H), 5.90 (brs, 1H), 6.87-6.96 (m, 3H), 7.13 (d, J=1.47 Hz, 1H), 7.19 (d, J=1.71 Hz, 2H), 7.62-7.73 (m, 4H); Calcd for C25H22Cl2F3NO2 (M+H) 496.10, Found 496.

Example 8

2-[5-(2,5-Bis-trifluoromethyl-phenylamino)-4'-trifluoromethyl-biphenyl-3-yl]-4-methyl-pentanoic acid

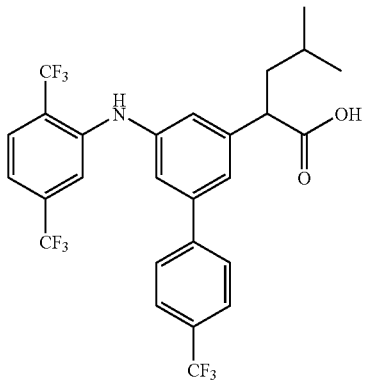

The title compound was prepared from 2,5-bis-trifluoromethyl-aniline and compound 1g under the condition described in Example 1; Calcd for C27H22F9NO2 (M+H) 564.15, Found 564.

Example 9

2-[5-(4-Fluoro-2-trifluoromethyl-phenylamino)-4'-trifluoromethyl-biphenyl-3-yl]-4-methyl-pentanoic acid

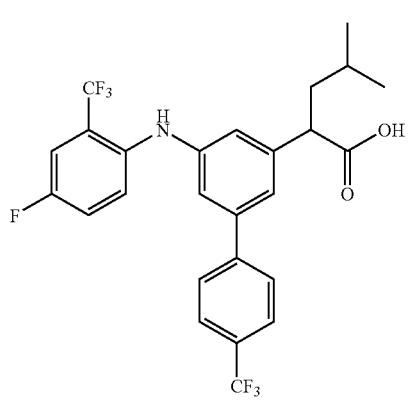

The title compound was prepared from 4-fluoro-2-trifluoromethyl-aniline and compound 1g under the condition described in Example 1; $^1$H NMR (400 MHz, CHLOROFORM-D) δ ppm 0.90-1.00 (m, 6H), 1.57 (dt, J=13.27, 6.69 Hz, 1H), 1.71 (ddd, J=13.69, 7.21, 6.97 Hz, 1H), 1.95-2.06 (m, 1H), 3.69 (t, J=7.83 Hz, 1H), 5.94 (s, 1H), 7.02 (d, J=1.71 Hz, 1H), 7.10-7.19 (m, 3H), 7.33 (dd, J=8.68, 3.06 Hz, 1H), 7.36 (dd, J=9.05, 4.89 Hz, 1H), 7.65 (q, J=8.40 Hz, 4H); Calcd for C26H22F7NO2 (M+H) 514.15, Found 514.

Example 10

4-Methyl-2-[4'-trifluoromethyl-5-(3-trifluoromethyl-phenylamino)-biphenyl-3-yl]-pentanoic acid

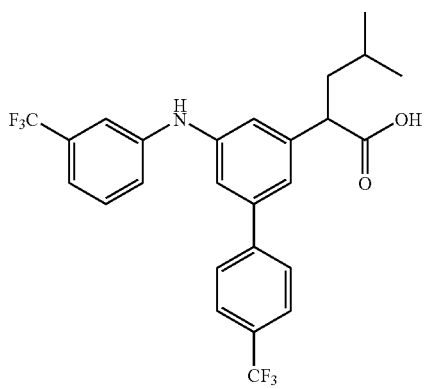

The title compound was prepared from 3-trifluoromethyl-aniline and compound 1g under the condition described in Example 1; $^1$H NMR (400 MHz, CHLOROFORM-D) δ ppm 0.90-1.00 (m, 6H), 1.57 (dt, J=13.39, 6.63 Hz, 1H), 1.70-1.79 (m, 1H), 1.94-2.05 (m, 1H), 3.71 (t, J=7.83 Hz, 1H), 7.12-7.23 (m, 5H), 7.30-7.40 (m, 2H), 7.66 (q, J=8.40 Hz, 4H); Calcd for C26H23F6NO2 (M+H) 496.16, Found 496.

Example 11

4-Methyl-2-[4'-trifluoromethyl-5-(4-trifluoromethyl-phenylamino)-biphenyl-3-yl]-pentanoic acid

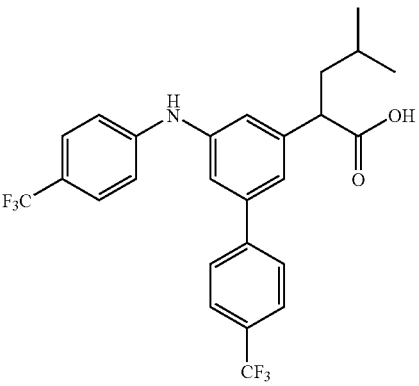

The title compound was prepared from 4-trifluoromethyl-aniline and compound 1g under the condition described in Example 1; $^1$H NMR (400 MHz, CHLOROFORM-D) δ ppm 0.95 (d, J=6.36 Hz, 6H), 1.57 (dt, J=13.27, 6.69 Hz, 1H), 1.74 (ddd, J=13.69, 7.21, 6.97 Hz, 1H), 1.96-2.05 (m, 1H), 3.66-3.76 (m, 1H), 7.07-7.12 (m, 2H), 7.14-7.20 (m, 2H), 7.25-7.29 (m, 1H) 7.50 (d, J=8.56 Hz, 2H) 7.62-7.72 (m, 4H); Calcd for C26H23F6NO2 (M+H) 496.16, Found 496.

Example 12

2-[5-(4-Chloro-3-trifluoromethyl-phenylamino)-4'-trifluoromethyl-biphenyl-3-yl]-4-methyl-pentanoic acid

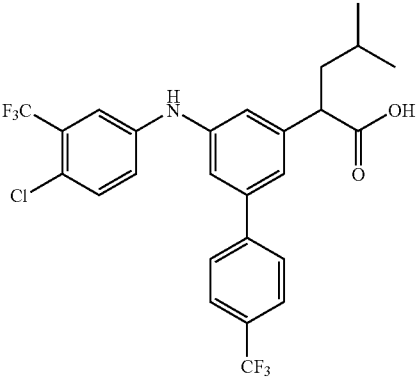

The title compound was prepared from 4-chloro-3-trifluoromethyl-aniline and compound 1g under the condition described in Example 1; $^1$H NMR (400 MHz, MeOD) δ ppm 0.88-0.98 (m, 6H), 1.55 (ddd, J=13.33, 6.85, 6.72 Hz, 1H), 1.67-1.75 (m, 1H), 1.92-2.01 (m, 1H), 3.71 (t, J=7.70 Hz, 1H), 7.19 (d, J=1.71 Hz, 1H), 7.21 (s, 1H), 7.26-7.34 (m, 2H), 7.35-7.45 (m, 2H), 7.71-7.80 (m, 4H); Calcd for C26H22ClF6NO2 (M+H) 530.12, Found 530.

Example 13

2-[5-(4-Cyano-phenylamino)-4'-trifluoromethyl-biphenyl-3-yl]-4-methyl-pentanoic acid

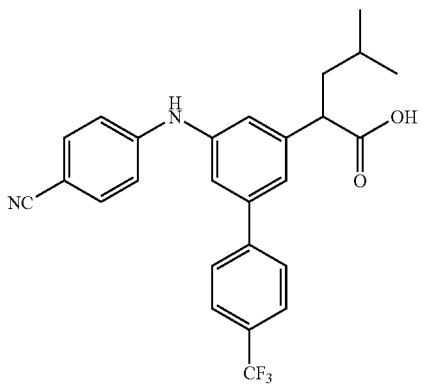

The title compound was prepared from 4-cyano-aniline and compound 1g under the condition described in Example 1; Calcd for C26H23F3N2O2 (M+H) 453.17, Found 453.

Example 14

2-[5-(4-Cyano-phenylamino)-4'-trifluoromethyl-biphenyl-3-yl]-2,4-dimethyl-pentanoic acid

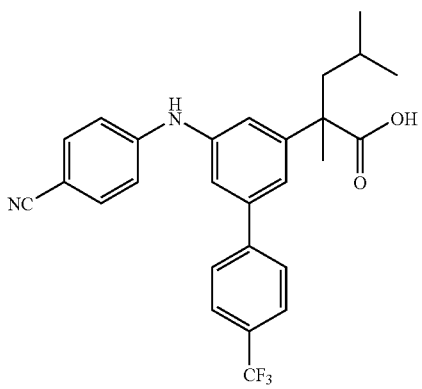

A mixture of compound 1g (50 mg, 0.098 mmol), 4-cyano-aniline (20 mg, 0.169 mmol), Pd(OAc)$_2$ (6.6 mg, 0.029 mmol), racemic-2-(di-t-butylphosphino)-1,1'-binaphthyl (35 mg, 0.088 mmol) and NaOt-Bu (11.3 mg, 0.12 mmol) in toluene (1.5 mL) was microwaved (300 w) at 140° C. for 10 min. After cooling to room temperature, the solution was partitioned between EtOAc and H$_2$O. The organic layer was dried (Na$_2$SO$_4$), concentrated and purified by column chromatography to give an ethyl ester intermediate.

To a mixture of the above intermediate in THF (1 mL) was added KOt-Bu (1M in THF, 0.098 mL, 0.098 mmol). After stirring for 30 min, MeI (42 mg, 0.295 mmol) was added. The reaction mixture was stirred at room temperature for 15 h, concentrated and purified by preparative TLC to give a methylated ester intermediate.

The title compound was prepared from the above intermediate under the same saponification condition described in Example 1; H NMR (400 MHz, MeOD) δ ppm 0.89 (d, J=6.85 Hz, 3H), 1.00 (d, J=6.60 Hz, 3H), 1.73 (m, 1H), 2.23 (d, J=5.87 Hz, 1H), 2.28-2.33 (m, 1H), 3.45 (s, 3H), 6.89-6.92 (m, 2H), 7.44 (t, J=1.71 Hz, 1H), 7.50-7.55 (m, 3H), 7.71 (t, J=1.59 Hz, 1H), 7.77-7.85 (m, 4H); Calcd for C27H25F3N2O2 (M+H) 467.19, Found 467.

Example 15

2-[5-(3-Isopropyl-phenoxy)-4'-trifluoromethyl-biphenyl-3-yl]-4-methyl-pentanoic acid

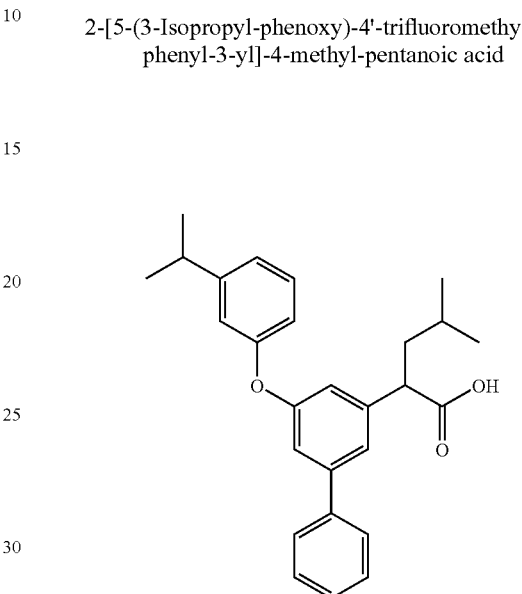

a) (3,5-Bis-benzyloxy-phenyl)-acetic acid methyl ester

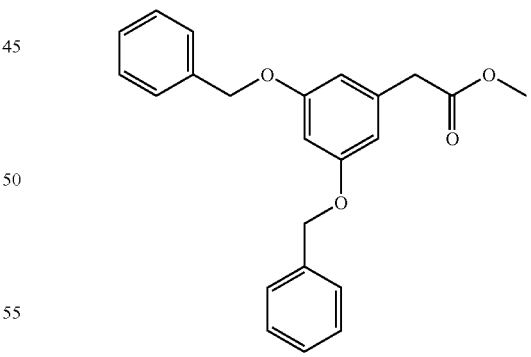

(3,5-dihydroxy-phenyl)-acetic acid methyl ester (5 g, 27.4 mmol) in anhydrous DMF (20 mL) was treated with K$_2$CO$_3$ (11.4 g, 82.5 mmol) and benzyl bromide (6.5 mL, 55 mmol). The resultant mixture was stirred overnight at room temperature. Water was added to the reaction mixture and the aqueous layer extracted with EtOAc (3×50 mL). The organic layers were combined, washed with brine, dried over MgSO$_4$, filtered and concentrated to give the title compound as a brown solid (9.82 g, 99%).

b) 2-(3,5-Bis-benzyloxy-phenyl)-4-methyl-pent-4-enoic acid methyl ester

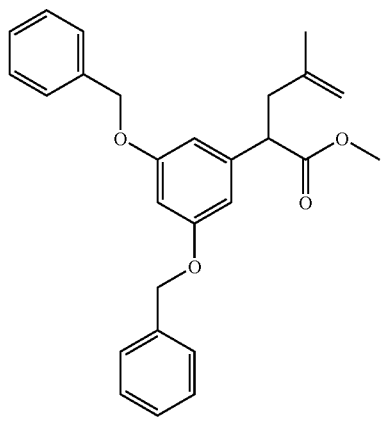

A 2M solution of LDA in THF-heptane-ethylbenzene (21.5 mL, 43.0 mmol) was added dropwise over 12 min to a stirred solution of (3,5-bis-benzyloxyphenyl)acetic acid methyl ester (13.0 g, 35.9 mmol) in THF (80 mL) at −78° C. under a nitrogen atmosphere. The temperature was maintained below −70° C. for a further 50 min then 3-bromo-2-methylpropene (4.0 mL, 39.7 mmol) was added in one portion and the reaction mixture was warmed to 0° C. After 2 h the mixture was concentrated in vacuo, diluted with sat. aq. NH₄Cl (100 mL) and extracted with EtOAc (100 mL). The organic layer was washed with brine (100 mL), dried (MgSO₄), concentrated in vacuo and purified by flash chromatography (silica, 0-10% EtOAc in petroleum ether) to afford the title product as a yellow oil (14.1 g, 94%).

¹H-NMR (400 MHz, CD₃Cl): δ 7.42-7.25 (m, 10H), 6.58 (s, 2H), 6.52 (s, 1H), 5.02 (s, 4H), 4.74 (s, 1H), 4.66 (s, 1H), 3.74 (t, 1H), 3.64 (s, 3H), 2.79 (dd, 1H), 2.38 (dd, 1H), 1.70 (s, 3H.

c) 2-(3-Benzyloxy-5-hydroxy-phenyl)-4-methyl-pent-4-enoic acid methyl ester

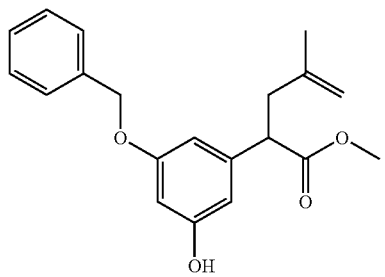

10% Pd/C (Aldrich cat no 205699, 0.55 g) was added to a stirred solution of 2-(3,5-bis-benzyloxyphenyl)-4-methyl-pent-4-enoic acid methyl ester (14.1 g, 33.8 mmol) and NaOH (1.50 g, 37.5 mmol) in MeOH (180 mL) at room temperature. Stirring was continued for 1 h under H₂ (1 atm.) then the mixture was filtered through Celite, concentrated in vacuo, suspended in water (100 mL) and adjusted to pH 2 with 1M HCl. The mixture was extracted with EtOAc (2×180 mL); the combined organic layer was washed with brine (50 mL), dried (MgSO₄), concentrated in vacuo and purified by flash chromatography (silica, 0-30% EtOAc in petroleum ether) to give the title product as a yellow oil (7.40 g, 67%).

¹H-NMR (400 MHz, CDCl₃): δ 7.41-7.25 (m, 5H), 6.54 (s, 1H), 6.43 (s, 1H), 6.38 (s, 1H), 5.01 (s, 3H), 4.74 (s, 1H), 4.67 (s, 1H), 3.70 (t, 1H), 3.65 (s, 3H), 2.78 (dd, 1H), 2.38 (dd, 1H), 1.71 (s, 3H); RT=3.14 min. Mass spectrum (ESI, m/z) 325 (M−1)

d) 2-(3-Benzyloxy-5-trifluoromethanesulfonyloxy-phenyl)-4-methyl-pent-4-enoic acid methyl ester

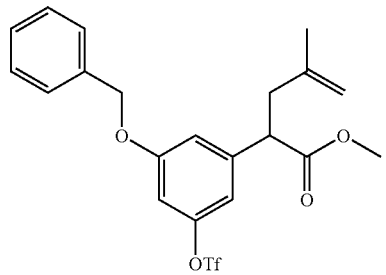

Trifluoromethanesulfonic anhydride (3.3 mL, 10.1 mmol) was added dropwise to a stirred solution of 2-(3-benzyloxy-5-hydroxyphenyl)-4-methyl-pent-4-enoic acid methyl ester (4.5 g, 13.8 mmol) and pyridine (3.0 mL, 38.7 mmol) in DCM (80 mL) at 0° C. then warmed to room temperature. After 1 h, the mixture was washed with 1M HCl (50 mL), dried (MgSO₄) and concentrated in vacuo to afford the title product as an orange oil (6.10 g, 96%). ¹H-NMR (400 MHz, CDCl₃): δ 7.42-7.30 (m, 5H), 6.97 (s, 1H), 6.85 (s, 1H), 6.78 (s, 1H), 5.05 (s, 3H), 4.75 (s, 1H), 4.64 (s, 1H), 3.77 (t, 1H), 3.66 (s, 3H), 2.77 (dd, 1H), 2.40 (dd, 1H), 1.69 (s, 3H).

e) 2-(5-Benzyloxy-4'-trifluoromethyl-biphenyl-3-yl)-4-methyl-pent-4-enoic acid methyl ester

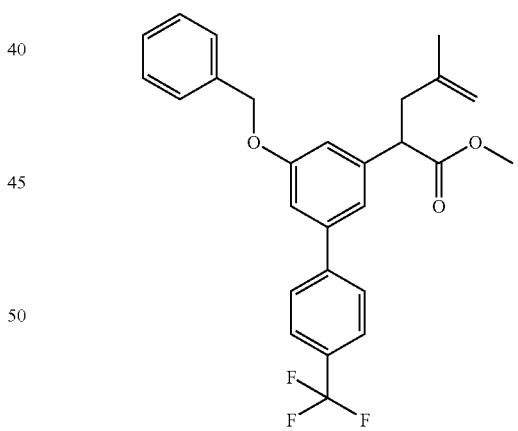

A mixture of 2-(3-benzyloxy-5-trifluoromethanesulfonyloxy-phenyl)-4-methyl-pent-4-enoic acid methyl ester (4.3 g, 9.4 mmol), 4-trifluoromethylphenylboronic acid (2.6 g, 13.7 mmol), K₂CO₃ solution (2M, 9.4 mL) and DME (50 mL) was purged with N₂ three times before adding Pd(PPh₃)₄ (400 mg, 0.3 mmol). The mixture was heated at 95° C. for 5 h (followed by HPLC). The reaction was diluted with EtOAc (200 mL) and then was washed successively with NaHCO₃ solution and brine. The organic layer was dried (Mg₂SO₄), filtered and concentrated in vacuo to give the title compound as an oil. The residue was used crude in the next step.

f) 2-(5-Hydroxy-4'-trifluoromethyl-biphenyl-3-yl)-4-methyl-pentanoic acid methyl ester

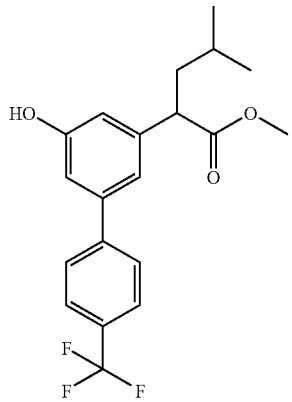

10% Pd/C (Aldrich cat no 205699, 0.30 g) was added to a stirred solution of 2-(5-benzyloxy-4'-trifluoromethyl-biphenyl-3-yl)-4-methyl-pent-4-enoic acid methyl ester (2.71 g, 5.96 mmol) in MeOH (75 mL) at room temperature. Stirring was continued for 2 days under $H_2$ (1 atm). Then the mixture was filtered through Celite, concentrated in vacuo to give the compound (1.83 g, 84%) as a yellow oil.
$^1$H-NMR (400 MHz, $CD_3Cl$): δ 7.70-7.60 (m, 4H), 7.08 (t, 1H), 7.00-6.95 (m, 1H), 6.90-6.87 (m, 1H), 5.56 (br. s, 1H), 3.73-3.65 min (m, 4H), 2.04-1.92 (m, 1H), 1.76-1.64 (m, 1H), 1.56-1.42 (m, 1H), 0.92 (d, 6H. Mass spectrum (ESI, m/z): 365 (M–H);

g) 2-[5-(3-Isopropyl-phenoxy)-4'-trifluoromethyl-biphenyl-3-yl]-4-methyl-pentanoic acid methyl ester

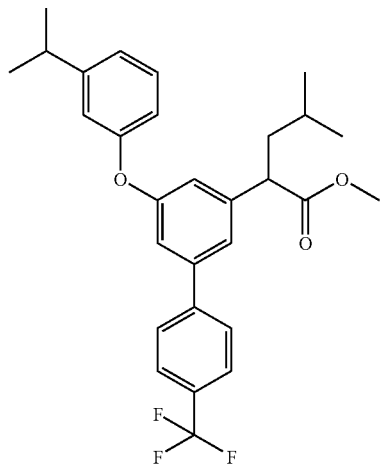

A mixture of 2-(5-hydroxy-4'-trifluoromethyl-biphenyl-3-yl)-4-methyl-pentanoic acid methyl ester (50 mg, 0.14 mmol), 3-isopropylphenyl boronic acid (45 mg, 0.27 mmol), copper acetate (26 mg, 0.14 mmol), triethylamine (57 μL, 0.4 mmol) and powdered 4 Å molecular sieves in DCM (1 mL) were stirred at room temperature for 2 days. The reaction mixture was concentrated in vacuo. Purification by flash chromatography (EtOAc:petroleum ether) give the title compound (32 mg, 48%).

h) 2-[5-(3-Isopropyl-phenoxy)-4'-trifluoromethyl-biphenyl-3-yl]-4-methyl-pentanoic acid A mixture of 2-[5-(3-isopropyl-phenoxy)-4'-trifluoromethyl-biphenyl-3-yl]-4-methyl-pentanoic acid methyl ester (33 mg, 0.07 mmol), THF (0.6 mL), 10% aq. LiOH (0.2 mL) and MeOH (0.6 mL) was stirred at 30° C. for 3 h. The solution was concentrated and the residue was diluted with $H_2O$ (1 mL) and then acidified with conc HCl. The aqueous solution was extracted with DCM (3×1 mL) and the organic layers were filtered through PTFE filter. The solution was concentrated in vacuo to give a solid residue. The solid was purified using reverse phase preparative HPLC (MeCN, $H_2O$) to afford the title compound (21.6 mg, 67%).
$^1$H-NMR ($CD_3Cl$; 400 MHz): δ 7.64 (dd, 4H), 7.29-7.23 (m, 2H), 7.11 (br. s, 1H), 7.05 (br. s), 7.00 (dd, 1H), 6.96-6.93 (m, 1H), 6.84 (d, 1H), 3.80-3.65 (m, 1H), 2.95-2.85 (m, 1H), 2.02-1.90 (m, 1H), 1.80-1.65 (m, 1H), 1.60-1.45 (m, 1H), 1.23 (d, 6H), 0.92 (d, 6H).

Example A 2-(4'-Chloro-5-hydroxy-3'-trifluoromethyl-biphenyl-3-yl)-4-methyl-pentanoic acid methyl ester

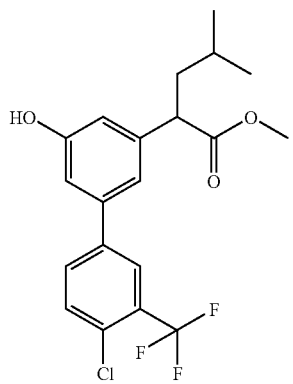

The title compound was prepared in 70% yield from 2-(3-benzyloxy-5-trifluoromethanesulfonyloxy-phenyl)-4-methyl-pent-4-enoic acid methyl ester (prepared in Example 15, step (d)) under the conditions described in Example 15 step (e-f) using 4-chloro-5-trifluoromethylphenylboronic acid in step (e). $^1$H-NMR (400 MHz, $CDCl_3$): δ 7.84 (s, 1H), 7.65 (d, 1H), 7.55 (d, 1H), 7.04 (s, 1H), 6.92 (m, 1H), 6.86 (m, 1H), 4.98 (br s, 1H), 3.68 (m, 4H), 1.97 (m, 1H), 1.68 (m, 1H), 1.49 (m, 1H), 0.92 (d, 6H); Mass Spectrum (m/z, ESI) 399 (M–H)

Example B 2-(3'-Fluoro-5-hydroxy-5'-trifluoromethyl-biphenyl-3-yl)-4-methyl-pentanoic acid methyl ester

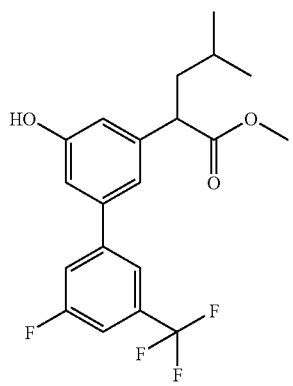

The title compound was prepared in 73% yield from 2-(3-benzyloxy-5-trifluoromethanesulfonyloxy-phenyl)-4-methyl-pent-4-enoic acid methyl ester (prepared in Example 15, step (d)) under the conditions described in Example 15, step (e-f) using 3-fluoro-5-trifluoromethylphenylboronic acid in step (e).

¹H-NMR (400 MHz, CDCl₃): δ 7.59 (s, 1H), 7.44 (dm, 1H, J=9.3 Hz), 7.30 (dm, 1H, J=8.3 Hz), 7.06 (m, 1H), 6.94 (m, 1H), 6.89 (m, 1H), 4.97 (s, 1H), 3.68 (m, 1H), 3.68 (s, 3H), 1.99 (m, 1H), 1.70 (m, 1H), 1.49 (m, 1H), 0.92 (d, 6H, J=6.6 Hz).

Example C 2-(5-Hydroxy-3',5'-bis-trifluoromethyl-biphenyl-3-yl)-4-methyl-pentanoic acid methyl ester

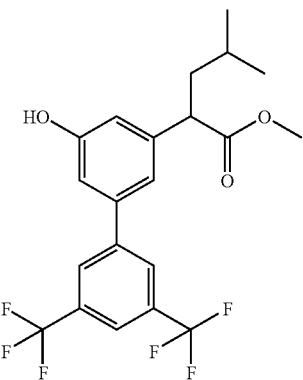

The title compound was prepared in 38% yield from 2-(3-benzyloxy-5-trifluoromethanesulfonyloxy-phenyl)-4-methyl-pent-4-enoic acid methyl ester (prepared in Example 15, step (d)) under the conditions described in Example 15, step (e-f) using 3,5-bis-trifluoromethylphenylboronic acid in step (e).

¹H-NMR (400 MHz, CD₃Cl): δ 7.96 (s, 2H), 7.85 (s, 1H), 7.07 (t, 1H), 6.97 (t, 1H), 6.93 (t, 1H), 3.71 (t, 1H), 3.70 (s, 3H), 2.04-1.97 (m, 1H), 1.74-1.67 (m, 1H), 1.55-1.48 (m, 1H), 0.93 (d, 6H); Mass spectrum (ESI, m/z): 433 (M−H);

Example 16

4-Methyl-2-[4'-trifluoromethyl-5-(4-trifluoromethyl-phenoxy)-biphenyl-3-yl]-pentanoic acid

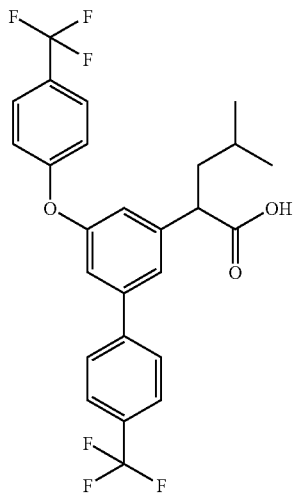

a) 4-Methyl-2-[4'-trifluoromethyl-5-(4-trifluoromethyl-phenoxy)-biphenyl-3-yl]-pentanoic acid methyl ester

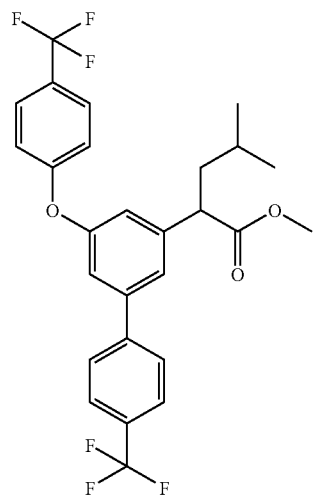

The title compound was prepared in 43% yield from 2-(5-hydroxy-4'-trifluoromethyl-biphenyl-3-yl)-4-methyl-pentanoic acid methyl ester and 4-trifluoromethylphenylboronic acid under the conditions described in Example 15, step (g).

b) 4-Methyl-2-[4'-trifluoromethyl-5-(4-trifluoromethyl-phenoxy)-biphenyl-3-yl]-pentanoic acid The title compound was prepared in 15% yield from 4-methyl-2-[4'-trifluoromethyl-5-(4-trifluoromethyl-phenoxy)-biphenyl-3-yl]-pentanoic acid methyl ester under the conditions described in Example 15, step (h).

¹H-NMR (400 MHz, CD₃Cl): δ 7.75-7.55 (m, 6H), 7.37 (s, 1H), 7.16 (s, 1H), 7.14-7.06 (m, 3H), 3.85-3.65 (m, 1H), 2.10-1.90 (m, 1H), 1.80-1.65 (m, 1H), 1.62-1.45 (m, 1H), 0.93 (d, 6H).

Example 17

4-Methyl-2-[4'-trifluoromethyl-5-(3,4,5-trifluoro-phenoxy)-biphenyl-3-yl]-pentanoic acid

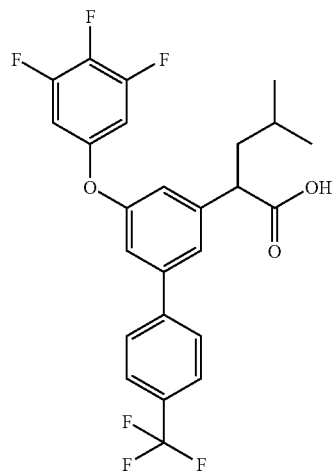

a) 4-Methyl-2-[4'-trifluoromethyl-5-(3,4,5-trifluoro-phenoxy)-biphenyl-3-yl]-pentanoic acid methyl ester

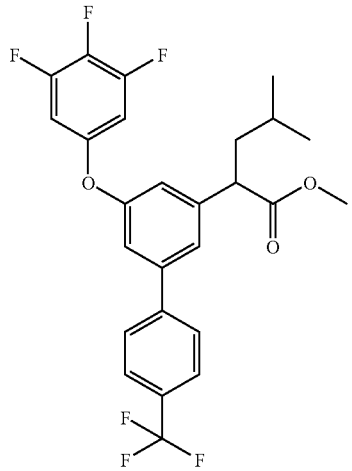

The title compound was prepared in 30% yield from 2-(5-hydroxy-4'-trifluoromethyl-biphenyl-3-yl)-4-methyl-pentanoic acid methyl ester and 3,4,5-trifluorophenylboronic acid under the conditions described in Example 15, step (g).

b) 4-Methyl-2-[4'-trifluoromethyl-5-(3-trifluoromethyl-phenoxy)-biphenyl-3-yl]-pentanoic acid The title compound was prepared in 60% yield from 4-methyl-2-[4'-trifluoromethyl-5-(3,4,5-trifluoro-phenoxy)-biphenyl-3-yl]-pentanoic acid methyl ester under the conditions described in Example 15, step (h).

$^1$H-NMR (400 MHz, CD$_3$Cl): δ 7.66 (dd, 4H), 7.37 (s, 1H), 7.13 (s, 1H), 7.06 (m, 3H), 6.61 (m, 2H), 3.77 (t, 1H), 2.0 (m, 1H), 1.72 (m, 1H), 1.54 (m, 1H), 0.93 (d, 6H).

Example 18

2-[5-(4-Fluoro-3-methoxy-phenoxy)-4'-trifluoromethyl-biphenyl-3-yl]-4-methyl-pentanoic acid

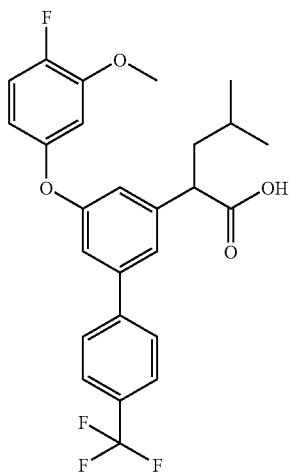

a) 2-[5-(4-Fluoro-3-methoxy-phenoxy)-4'-trifluoromethyl-biphenyl-3-yl]-4-methyl-pentanoic acid methyl ester

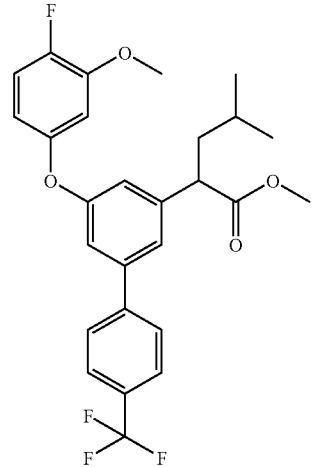

The title compound was prepared in 30% yield from 2-(5-hydroxy-4'-trifluoromethyl-biphenyl-3-yl)-4-methyl-pentanoic acid methyl ester and 4-fluoro-3-methoxyphenylboronic acid under the conditions described in Example 15, step (g).

b) 4-Methyl-2-[4'-trifluoromethyl-5-(3-trifluoromethyl-phenoxy)-biphenyl-3-yl]-pentanoic acid The title compound was prepared in 60% yield from 2-[5-(4-fluoro-3-methoxy-phenoxy)-4'-trifluoromethyl-biphenyl-3-yl]-4-methyl-pentanoic acid methyl ester under the conditions described in Example 15, step (h).

$^1$H-NMR (400 MHz, CD$_3$Cl): δ 7.64 (dd, 4H), 7.27 (s, 1H), 7.07 (s, 1H), 7.04 (m, 3H), 7.02 (m, 1H), 6.72 (dd, 1H), 6.55, (m, 1H), 3.84 (s, 3H), 3.72 (t, 1H), 2.0 (m, 1H), 1.72 (m, 1H), 1.54 (m, 1H), 0.93 (d, 6H).

Example 19

2-[5-(4-Methoxy-3-trifluoromethyl-phenoxy)-4'-trifluoromethyl-biphenyl-3-yl]-4-methyl-pentanoic acid

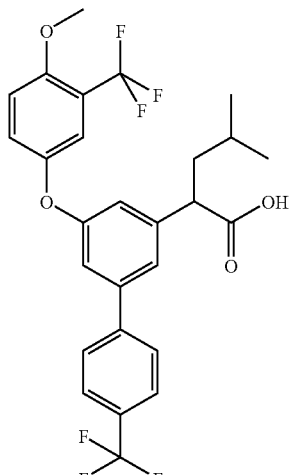

a) 2-[5-(4-Methoxy-3-trifluoromethyl-phenoxy)-4'-trifluoromethyl-biphenyl-3-yl]-4-methyl-pentanoic acid methyl ester

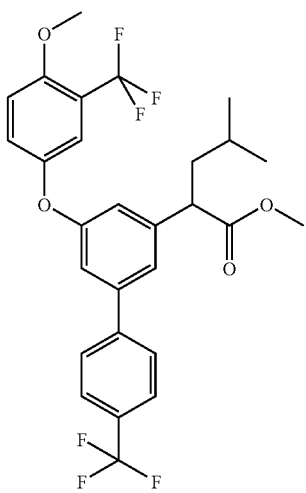

The title compound was prepared in 25% yield from 2-(5-hydroxy-4'-trifluoromethyl-biphenyl-3-yl)-4-methyl-pentanoic acid methyl ester and 4-methoxy-3-trifluoromethylphenylboronic acid under the conditions described in Example 15, step (g).

b) 2-[5-(4-Methoxy-3-trifluoromethyl-phenoxy)-4'-trifluoromethyl-biphenyl-3-yl]-4-methyl-pentanoic acid The title compound was prepared in 60% yield from 2-[5-(4-methoxy-3-trifluoromethyl-phenoxy)-4'-trifluoromethyl-biphenyl-3-yl]-4-methyl-pentanoic acid methyl ester under the conditions described in Example 15, step (h).

¹H-NMR (400 MHz, CD₃Cl): δ 7.66 (dd, 4H), 7.31 (s, 1H), 7.27 (s, 1H), 7.20 (m, 3H), 7.04 (m, 1H), 7.02 (dd, 1H), 7.00 (m, 1H), 3.92 (s, 3H), 3.73 (t, 1H), 2.0 (m, 1H), 1.72 (m, 1H), 1.54 (m, 1H), 0.93 (d, 6H).

a) 4-Methyl-2-[4'-trifluoromethyl-5-(3-trifluoromethyl-phenoxy)-biphenyl-3-yl]-pentanoic acid methyl ester

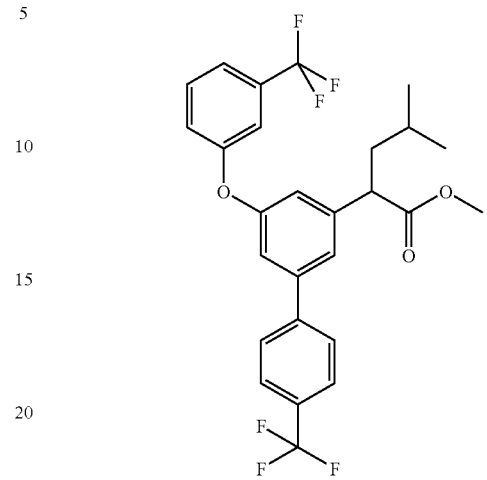

The title compound was prepared in 25% yield from 2-(5-hydroxy-4'-trifluoromethyl-biphenyl-3-yl)-4-methyl-pentanoic acid methyl ester and 3-trifluoromethylphenylboronic acid under the conditions described in Example 15, step (g).

b) 4-Methyl-2-[4'-trifluoromethyl-5-(3-trifluoromethyl-phenoxy)-biphenyl-3-yl]-pentanoic acid The title compound was prepared in 60% yield from 4-methyl-2-[4'-trifluoromethyl-5-(3-trifluoromethyl-phenoxy)-biphenyl-3-yl]-pentanoic acid under the conditions described in Example 15, step (h).

¹H-NMR (400 MHz, CD₃Cl): δ 7.61 (d, 2H), 7.56 (d, 2H), 7.27 (m, 1H), 7.23 (m, 1H), 7.04 (d, 1H), 6.77 (m, 2H), 6.69 (m, 1H), 3.62 (t, 1H), 1.87 (m, 1H), 1.65 (m, 1H), 1.44 (m, 1H), 0.83 (dd, 6H).

Example 20

2 4-Methyl-2-[4'-trifluoromethyl-5-(3-trifluoromethyl-phenoxy)-biphenyl-3-yl]-pentanoic acid

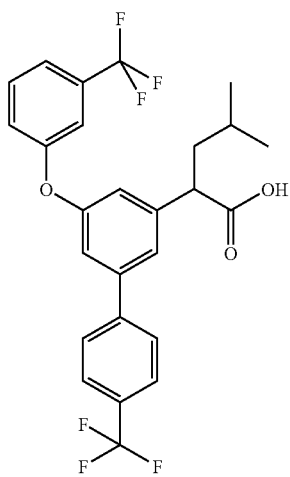

Example 21

4-Methyl-2-[4'-chloro-3'-trifluoromethyl-5-(3-fluoro-5-trifluoromethylphenoxy)-biphenyl-3-yl]-pentanoic acid

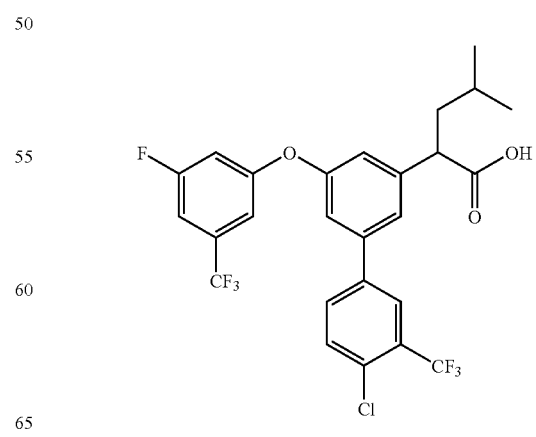

a)  4-Methyl-2-[4'-chloro-3'-trifluoromethyl-5-(3-fluoro-5-trifluoromethylphenoxy)-biphenyl-3-yl]-pentanoic acid methyl ester

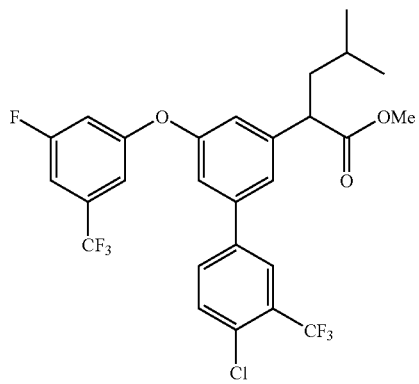

The title compound was prepared in 50% yield from 2-(5-hydroxy-4'-chloro-3'-trifluoromethyl-biphenyl-3-yl)-4-methyl-pentanoic acid methyl ester (prepared in Example A) and 3-fluoro-5-trifluoromethylphenylboronic acid under the conditions described in Example 15, step (g).

b)  4-Methyl-2-[4'-chloro-3'-trifluoromethyl-5-(3-fluoro-5-trifluoromethylphenoxy)-biphenyl-3-yl]-pentanoic acid The title compound was prepared in 90% yield from 4-methyl-2-[4'-chloro-3'-trifluoromethyl-5-(3-fluoro-5-trifluoromethylphenoxy)-biphenyl-3-yl]-pentanoic acid methyl ester under the conditions described in Example 15, step (h).
$^1$H-NMR (400 MHz, CDCl$_3$): δ 7.79 (d, 1H), 7.55 (d, 1H), 7.50 (d, 1H), 7.28 (d, 1H), 7.05 (m, 4H), 6.82 (d, 1H), 3.59 (t, 1H), 1.84 (m, 1H), 1.64 (m, 1H), 1.41 (m, 1H), 0.83 (d, 6H).

Example 22

4-Methyl-2-[4'-chloro-3'-trifluoromethyl-5-(3-trifluoromethylphenoxy)-biphenyl-3-yl]-pentanoic acid

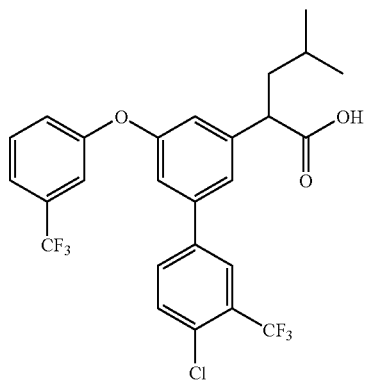

a) 4-Methyl-2-[4'-chloro-3'-trifluoromethyl-5-(3-trifluoromethylphenoxy)-biphenyl-3-yl]-pentanoic acid methyl ester

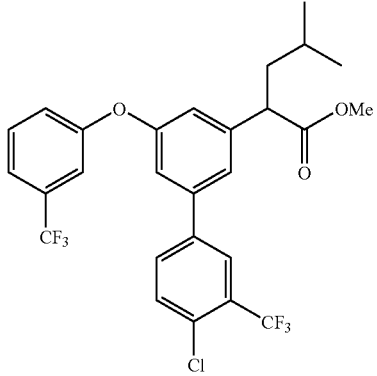

The title compound was prepared in 71% yield from 2-(5-hydroxy-4'-chloro-3'-trifluoromethyl-biphenyl-3-yl)-4-methyl-pentanoic acid methyl ester (prepared in Example A) and 3-trifluoromethylphenylboronic acid under the conditions described in Example 15, step (g).

b) 4-Methyl-2-[4'-chloro-3'-trifluoromethyl-5-(3-trifluoromethylphenoxy)-biphenyl-3-yl]-pentanoic acid The title compound was prepared in 100% yield from 4-methyl-2-[4'-chloro-3'-trifluoromethyl-5-(3-trifluoromethylphenoxy)-biphenyl-3-yl]-pentanoic acid methyl ester under the conditions described in Example 15, step (h).
$^1$H-NMR (400 MHz, CDCl$_3$): δ 7.77 (d, 1H), 7.54 (dd, 1H), 7.47 (d, 1H), 7.40 (t, 1H), 7.32 (d, 1H), 7.23 (m, 1H), 7.19 (m, 1H), 7.13 (m, 1H), 7.01 (m, 2H), 3.56 (t, 1H), 1.80 (m, 1H), 1.63 (m, 1H), 1.39 (m, 1H), 0.81 (d, 6H).

Example 23

4-Methyl-2-[4'-chloro-3'-trifluoromethyl-5-(3,5-difluorophenoxy)-biphenyl-3-yl]-pentanoic acid

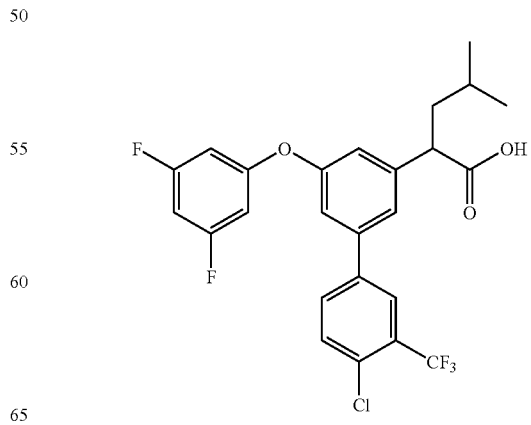

a) 4-Methyl-2-[4'-chloro-3'-trifluoromethyl-5-(3,5-difluorophenoxy)-biphenyl-3-yl]-pentanoic acid methyl ester

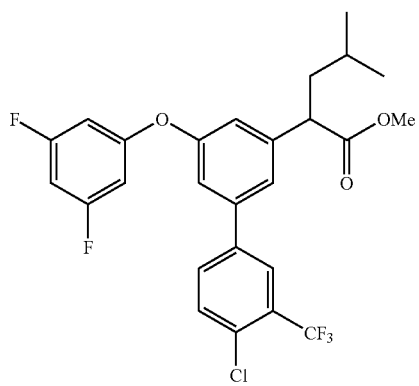

The title compound was prepared in 49% yield from 2-(5-hydroxy-4'-chloro-3'-trifluoromethyl-biphenyl-3-yl)-4-methyl-pentanoic acid methyl ester (prepared in Example A) and 3,5-difluorophenylboronic acid under the conditions described in Example 15, step (g).

b) 4-Methyl-2-[4'-chloro-3'-trifluoromethyl-5-(3,5-difluorophenoxy)-biphenyl-3-yl]-pentanoic acid The title compound was prepared in 100% yield from 4-methyl-2-[4'-chloro-3'-trifluoromethyl-5-(3,5-difluorophenoxy)-biphenyl-3-yl]-pentanoic acid methyl ester under the conditions described in Example 15, step (h).

$^1$H-NMR (400 MHz, CDCl$_3$): δ 7.78 (d, 1H), 7.54 (dd, 1H), 7.49 (d, 1H), 7.25 (t, 1H), 7.03 (s, 2H), 7.46 (m, 3H), 3.55 (t, 1H), 1.81 (m, 1H), 1.62 (m, 1H), 1.39 (m, 1H), 0.81 (d, 6H).

Example 24

4-Methyl-2-(5-phenoxy-4'-trifluoromethyl-biphenyl-3-yl)-pentanoic acid

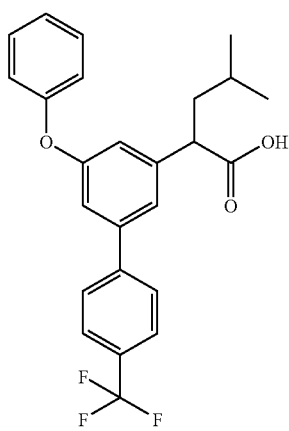

a) 4-Methyl-2-(5-phenoxy-4'-trifluoroethyl-biphenyl-3-yl)-pentanoic acid methyl ester

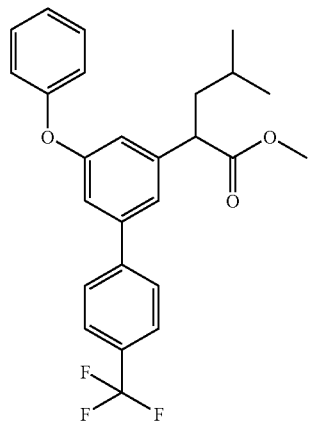

The title compound was prepared in 21% yield from 2-(5-hydroxy-4'-trifluoromethyl-biphenyl-3-yl)-4-methyl-pentanoic acid methyl ester (prepared in Example 15, step (f)) and benzeneboronic acid under the conditions described in Example 15 step (g).

b) 4-Methyl-2-(5-phenoxy-4'-trifluoromethyl-biphenyl-3-yl)-pentanoic acid

The title compound was prepared in 83% yield from 4-methyl-2-(5-phenoxy-4'-trifluoroethyl-biphenyl-3-yl)-pentanoic acid methyl ester under the conditions described in Example 15 step (h).

$^1$H-NMR (400 MHz, CDCl$_3$): δ 7.64 (d, 2H, 8.6 Hz), 7.60 (d, 2H, J=8.4 Hz), 7.34 (dd, 2H, J=7.6, 0.76 Hz), 7.27 (s, 1H), 7.12 (t, 1H, J=7.3 Hz), 7.05 (m, 4H), 3.68 (t, 1H, J=7.7 Hz), 1.95 (m, 1H), 1.70 (m, 1H), 1.50 (m, 1H), 0.90 (dd, 6H, J=6.6, 2.5 Hz).

Example 25

2-[5-(4-Fluoro-phenoxy)-4'-trifluoromethyl-biphenyl-3-yl]-4-methyl-pentanoic acid

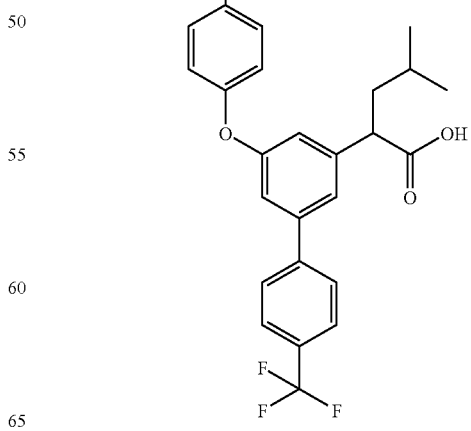

a) 2-[5-(4-Fluoro-phenoxy)-4'-trifluoromethyl-biphenyl-3-yl]-4-methyl-pentanoic acid methyl ester

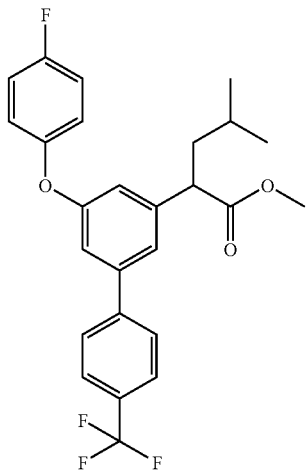

The title compound was prepared in 43% yield from 2-(5-hydroxy-4'-trifluoromethyl-biphenyl-3-yl)-4-methyl-pentanoic acid methyl ester (prepared in Example 15, step (f)) and 4-fluorobenzeneboronic acid under the conditions described in Example 15, step (g).

b) 2-[5-(4-Fluoro-phenoxy)-4'-trifluoromethyl-biphenyl-3-yl]-4-methyl-pentanoic acid The title compound was prepared in 100% yield from 2-[5-(4-fluoro-phenoxy)-4'-trifluoromethyl-biphenyl-3-yl]-4-methyl-pentanoic acid methyl ester under the conditions described in Example 15, step (h).

$^1$H-NMR (400 MHz, CDCl$_3$): δ 7.61 (d, 2H, J=8.3 Hz), 7.55 (d, 2H, J=8.3 Hz), 7.24 (s, 1H), 6.98 (m, 6H), 3.62 (m, 1H), 1.88 (m, 1H), 1.65 (m, 1H), 1.54 (m, 1H), 0.85 (dd, 6H, J=6.3, 3.3 Hz).

a) 2-[5-(3-Fluoro-phenoxy)-4'-trifluoromethyl-biphenyl-3-yl]-4-methyl-pentanoic acid methyl ester

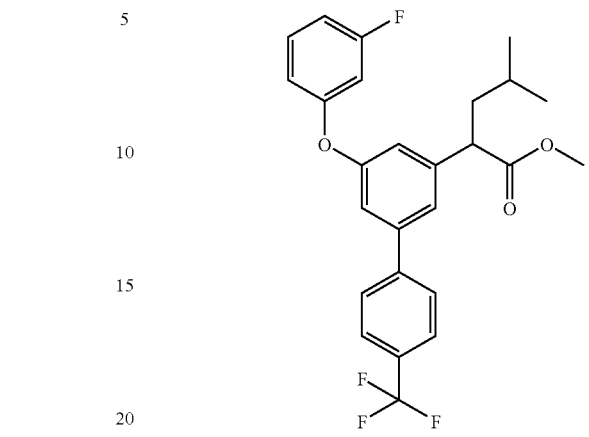

The title compound was prepared in 26% yield from 2-(5-hydroxy-4'-trifluoromethyl-biphenyl-3-yl)-4-methyl-pentanoic acid methyl ester (prepared in Example 15, step (f)) and 3-fluorobenzeneboronic acid under the conditions described in Example 15, step (g).

b) 2-[5-(3-Fluoro-phenoxy)-4'-trifluoromethyl-biphenyl-3-yl]-4-methyl-pentanoic acid The title compound was prepared in 100% yield from 2-[5-(3-fluoro-phenoxy)-4'-trifluoromethyl-biphenyl-3-yl]-4-methyl-pentanoic acid methyl ester under the conditions described in Example 15, step (h).

$^1$H-NMR (400 MHz, CDCl$_3$): δ 7.61 (d, 2H, J=8.3 Hz), 7.57 (d, 2H, J=8.3 Hz), 7.27 (m, 1H), 7.24 (m, 1H), 7.06 (s, 1H), 7.04 (s, 1H), 6.78 (m, 1H), 6.68 (dt, 1H, J=10.1, 2.3 Hz), 3.62 (br. S, 1H), 1.87 (m, 1H), 1.65 (m, 1H), 1.44 (m, 1H), 0.84 (dd, 6H, J=6.4, 3.4 Hz).

Example 26

2-[5-(3-Fluoro-phenoxy)-4'-trifluoromethyl-biphenyl-3-yl]-4-methyl-pentanoic acid

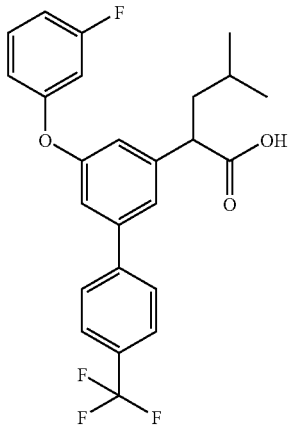

Example 27

2-[5-(3,5-Difluoro-phenoxy)-4'-trifluoromethyl-biphenyl-3-yl]-4-methyl-pentanoic acid

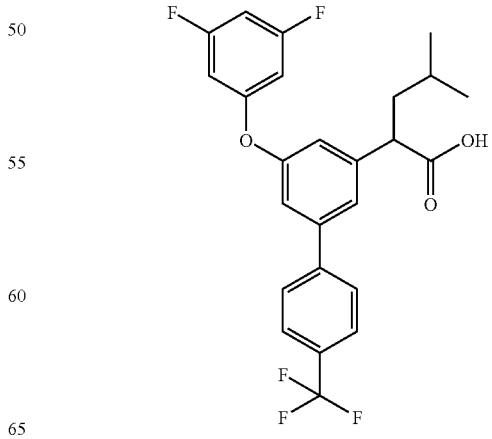

a) 2-[5-(3,5-Difluoro-phenoxy)-4'-trifluoromethyl-biphenyl-3-yl]-4-methyl-pentanoic acid methyl ester

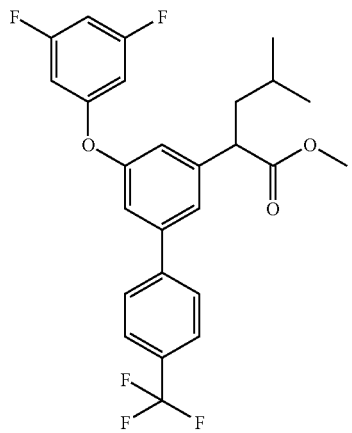

The title compound was prepared in 15% yield from 2-(5-hydroxy-4'-trifluoromethyl-biphenyl-3-yl)-4-methyl-pentanoic acid methyl ester (prepared in Example 15, step (f)) and 3,5-difluorobenzeneboronic acid under the conditions described in Example 15, step (g).

b) 2-[5-(3,5-Difluoro-phenoxy)-4'-trifluoromethyl-biphenyl-3-yl]-4-methyl-pentanoic acid The title compound was prepared in 100% yield from 2-[5-(3,5-difluoro-phenoxy)-4'-trifluoromethyl-biphenyl-3-yl]-4-methyl-pentanoic acid methyl ester under the conditions described in Example 15, step (h).

$^1$H-NMR (400 MHz, CDCl$_3$): δ 7.66 (d, 2H, J=8.3 Hz), 7.61 (d, 2H, J=8.3 Hz), 7.35 (m, 1H), 7.13 (dd, 1H, J=2.3, 0.51 Hz), 7.07 (m, 1H), 6.50 (m, 3H), 3.69 (t, 1H, J=7.8 Hz), 1.94 (m, 1H), 1.69 (m, 1H), 1.49 (m, 1H), 0.89 (dd, 6H, J=6.6, 2.5 Hz).

Example 28

2-[5-(4-Methoxy-phenoxy)-4'-trifluoromethyl-biphenyl-3-yl]-4-methyl-pentanoic acid

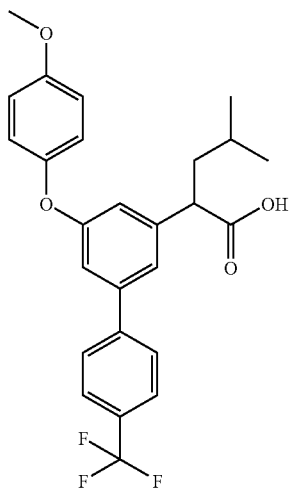

a) 2-[5-(4-Methoxy-phenoxy)-4'-trifluoromethyl-biphenyl-3-yl]-4-methyl-pentanoic acid methyl ester

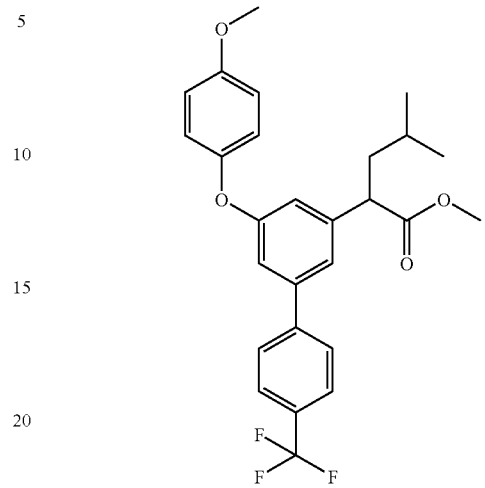

The title compound was prepared in 17% yield from 2-(5-hydroxy-4'-trifluoromethyl-biphenyl-3-yl)-4-methyl-pentanoic acid methyl ester prepared in Example 15, step (f)) and 4-methoxybenzene boronic acid under the conditions described in Example 15, step (g).

b) 2-[5-(4-Methoxy-phenoxy)-4'-trifluoromethyl-biphenyl-3-yl]-4-methyl-pentanoic acid The title compound was prepared in 100% yield from 2-[5-(4-methoxy-phenoxy)-4'-trifluoromethyl-biphenyl-3-yl]-4-methyl-pentanoic acid methyl ester under the conditions described in Example 15, step (h).

$^1$H-NMR (400 MHz, CDCl$_3$): δ 7.64 (d, 2H, J=8.3 Hz), 7.59 (d, 2H, J=8.1 Hz), 7.22 (s, 1H), 7.01 (m, 4H), 6.89 (d, 2H, J=9.1 Hz), 3.80 (s, 3H), 3.68 (br. S, 1H), 1.96 (m, 1H), 1.70 (m, 1H), 1.52 (m, 1H), 0.91 (dd, 6H, J=6.6, 2.0 Hz).

Example 29

2-[5-(4-Chloro-phenoxy)-4'-trifluoromethyl-biphenyl-3-yl]-4-methyl-pentanoic acid

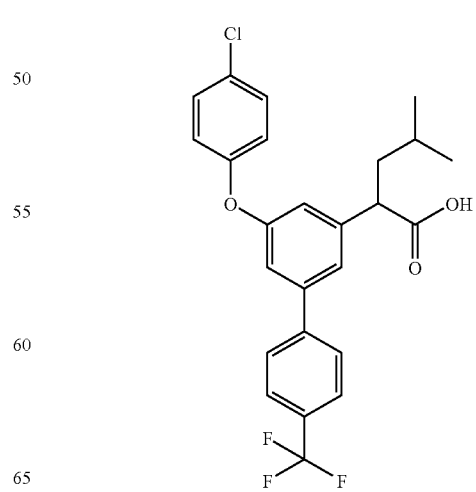

a) 2-[5-(4-Chloro-phenoxy)-4'-trifluoromethyl-biphenyl-3-yl]-4-methyl-pentanoic acid methyl ester

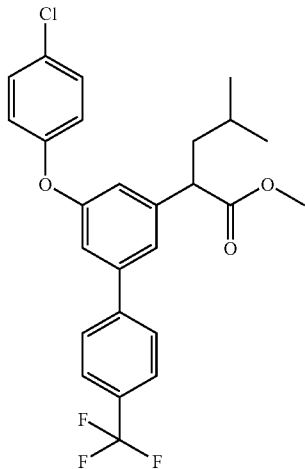

The title compound was prepared in 35% yield from 2-(5-hydroxy-4'-trifluoromethyl-biphenyl-3-yl)-4-methyl-pentanoic acid methyl ester (prepared in Example 15, step (f)) and 4-chlorobenzene boronic acid under the conditions described in Example 15, step (g).

b) 2-[5-(4-Chloro-phenoxy)-4'-trifluoromethyl-biphenyl-3-yl]-4-methyl-pentanoic acid The title compound was prepared in 83% yield from 2-[5-(4-chloro-phenoxy)-4'-trifluoromethyl-biphenyl-3-yl]-4-methyl-pentanoic acid methyl ester under the conditions described in Example 15 step (h).

$^1$H-NMR (400 MHz, CDCl$_3$): δ 7.62 (d, 2H, J=8.3 Hz), 7.57 (d, 2H, J=8.1 Hz), 7.27 (m, 3H), 7.02 (d, 2H, J=1.5 Hz), 6.93 (d, 2H, J=8.8 Hz), 3.62 (t, 1H, J=7.7 Hz), 1.88 (m, 1H), 1.66 (m, 1H), 1.45 (m, 1H), 0.86 (dd, 6H, J=6.6, 4.0 Hz).

Example 30

2-[5-(3-Fluoro-5-trifluoromethyl-phenoxy)-4'-trifluoromethyl-biphenyl-3-yl]-4-methyl-pentanoic acid a) 2-[5-(3-Fluoro-5-trifluoromethyl-phenoxy)-4'-trifluoromethyl-biphenyl-3-yl]-4-methyl-pentanoic acid methyl ester

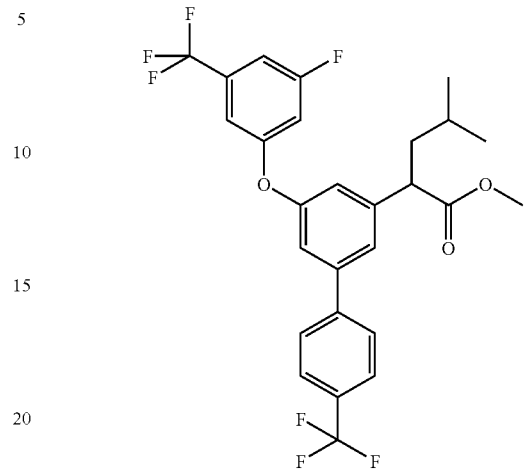

The title compound was prepared in 10% yield from 2-(5-hydroxy-4'-trifluoromethyl-biphenyl-3-yl)-4-methyl-pentanoic acid methyl ester (prepared in Example 15, step (f)) and 3-fluoro,5-trifluoromethylbenzene boronic acid under the conditions described in Example 15, step (g).

b) 2-[5-(4-Chloro-phenoxy)-4'-trifluoromethyl-biphenyl-3-yl]-4-methyl-pentanoic acid The title compound was prepared in 44% yield from 2-[5-(3-fluoro-5-trifluoromethyl-phenoxy)-4'-trifluoromethyl-biphenyl-3-yl]-4-methyl-pentanoic acid methyl ester under the conditions described in Example 15, step (h).

$^1$H-NMR (400 MHz, CDCl$_3$): δ 7.68 (d, 2H, J=8.3 Hz), 7.63 (d, 2H, J=8.1 Hz), 7.37 (m, 1H), 7.16 (m, 1H), 7.08 (m, 1H), 7.06 (m, 2H), 6.87 (dt, 2H, J=9.6, 2.3 Hz), 3.71 (t, 1H, J=7.8 Hz), 1.95 (m, 1H), 1.71 (m, 1H), 1.50 (m, 1H), 0.90 (dd, 6H, J=6.6, 2.3 Hz).

Example 31

2-[3'-Fluoro-5'-trifluoromethyl-5-(3-trifluoromethyl-phenoxy)-biphenyl-3-yl]-4-methyl-pentanoic acid

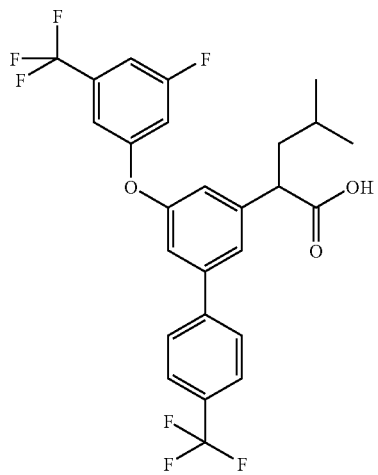

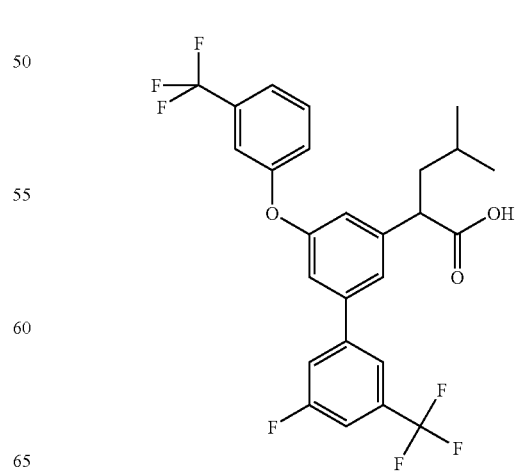

a) 2-[3'-Fluoro-5'-trifluoromethyl-5-(3-trifluoromethyl-phenoxy)-biphenyl-3-yl]-4-methyl-pentanoic acid methyl ester

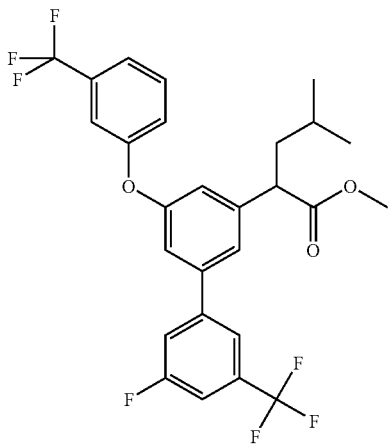

The title compound was prepared in 34% yield from 2-(3'-fluoro-5-hydroxy-5'-trifluoromethyl-biphenyl-3-yl)-4-methyl-pentanoic acid methyl ester (prepared in Example B) and 3-trifluoromethylbenzene boronic acid under the conditions described in Example 15, step (g).

b) 4-Methyl-2-[4'-trifluoromethyl-5-(3-trifluoromethyl-phenoxy)-biphenyl-3-yl]-pentanoic acid The title compound was prepared in 99% yield from 2-[3'-fluoro-5'-trifluoromethyl-5-(3-trifluoromethyl-phenoxy)-biphenyl-3-yl]-4-methyl-pentanoic acid methyl ester under the conditions described in Example 15, step (h).

$^1$H-NMR (400 MHz, CDCl$_3$): δ 7.57 (m, 1H), 7.47 (t, 1H, J=8.0 Hz), 7.37-7.43 (m, 2H), 7.32 (m, 2H), 7.27 (m, 1H), 7.20 (dd, 1H, J=8.1, 2.0 Hz), 7.14 (t, 1H, J=2.3, 1.77 Hz), 7.10 (t, 1H, J=2.0, 1.77 Hz), 3.74 (t, 1H, J=7.8 Hz), 2.00 (m, 1H), 1.73 (m, 1H), 1.54, (m, 1H), 0.93 (dd, 6H, J=6.6, 1.8 Hz).

Example 32

2-[3'-Fluoro-5-(3-fluoro-5-trifluoromethyl-phenoxy)-5'-trifluoromethyl-biphenyl-3-yl]-4-methyl-pentanoic acid

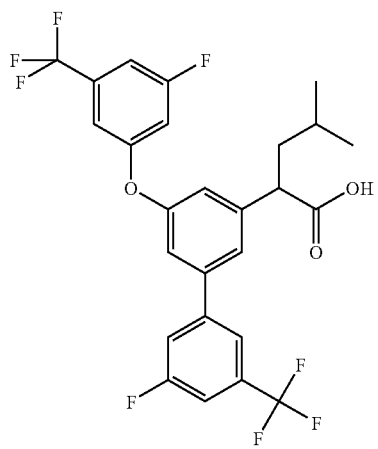

a) 2-[3'-Fluoro-5-(3-fluoro-5-trifluoromethyl-phenoxy)-5'-trifluoromethyl-biphenyl-3-yl]-4-methyl-pentanoic acid methyl ester

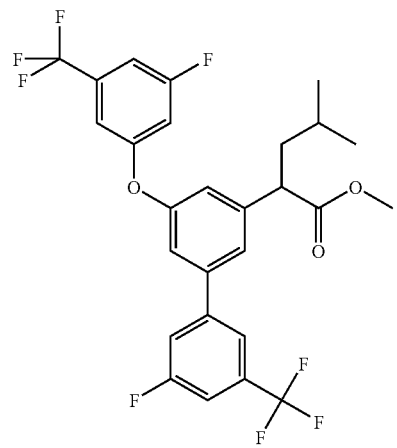

The title compound was prepared in 73% yield from 2-(3'-fluoro-5-hydroxy-5'-trifluoromethyl-biphenyl-3-yl)-4-methyl-pentanoic acid methyl ester (prepared in Example B) and 3-fluoro-5-trifluoromethylbenzene boronic acid under the conditions described in Example 15, step (g).

b) 2-[3'-Fluoro-5-(3-fluoro-5-trifluoromethyl-phenoxy)-5'-trifluoromethyl-biphenyl-3-yl]-4-methyl-pentanoic acid The title compound was prepared in 26% yield from 2-[3'-fluoro-5-(3-fluoro-5-trifluoromethyl-phenoxy)-5'-trifluoromethyl-biphenyl-3-yl]-4-methyl-pentanoic acid methyl ester under the conditions described in Example 15, step (h).

$^1$H-NMR (400 MHz, CDCl$_3$): δ 7.58 (br. s, 1H), 7.43 (br. d, 1H, J=9.6 Hz), 7.35 (m, 2H), 7.16 (br. s, 1H), 7.12, (br. s, 1H), 7.06, (m, 2H), 6.88 (d, 1H, J=9.4 Hz), 3.83 (br. s, 1H), 2.00 (br. s, 1H), 1.78 (br. s, 1H), 1.52 (br. s, 1H), 0.92 (br. s, 6H).

Example 33

2-[5-(3,5-Difluoro-phenoxy)-3'-fluoro-5'-trifluoromethyl-biphenyl-3-yl]-4-methyl-pentanoic acid

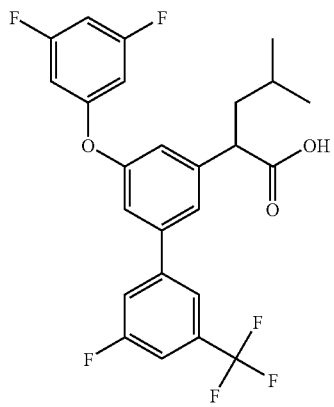

a) 2-[5-(3,5-Difluoro-phenoxy)-3'-fluoro-5'-trifluoromethyl-biphenyl-3-yl]-4-methyl-pentanoic acid methyl ester

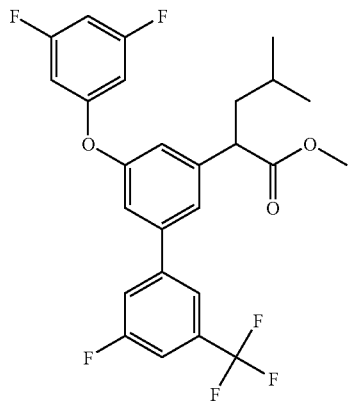

The title compound was prepared in 83% yield from 2-(3'-fluoro-5-hydroxy-5'-trifluoromethyl-biphenyl-3-yl)-4-methyl-pentanoic acid methyl ester (prepared in Example B) and 3,5-difluorobenzene boronic acid under the conditions described in Example 15, step (g).

b) 4-Methyl-2-[4'-trifluoromethyl-5-(3-trifluoromethyl-phenoxy)-biphenyl-3-yl]-pentanoic acid The title compound was prepared in 40% yield from 2-[5-(3,5-difluoro-phenoxy)-3'-fluoro-5'-trifluoromethyl-biphenyl-3-yl]-4-methyl-pentanoic acid methyl ester under the conditions described in Example 15, step (h).

$^1$H-NMR (400 MHz, CDCl$_3$): δ 7.57 (br. s, 1H), 7.42 (d, 1H, J=9.1 Hz), 7.33 (m, 2H), 7.15 (br. s, 1H), 7.12 (br. s, 1H), 6.59-6.51 (m, 3H), 3.77 (br. s, 1H), 2.00 (br. s, 1H), 1.75 (br. s, 1H), 1.54 (br. s, 1H), 0.94 (d, 6H, J=5.3 Hz).

Example 34

2-[5-(3-Fluoro-5-trifluoromethyl-phenoxy)-3',5'-bis-trifluoromethyl-biphenyl-3-yl]-4-methyl-pentanoic acid

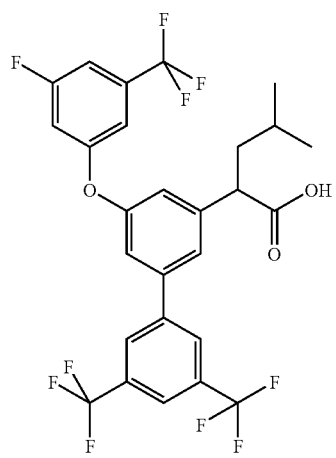

a) 2-[5-(3-Fluoro-5-trifluoromethyl-phenoxy)-3',5'-bis-trifluoromethyl-biphenyl-3-yl]-4-methyl-pentanoic acid methyl ester

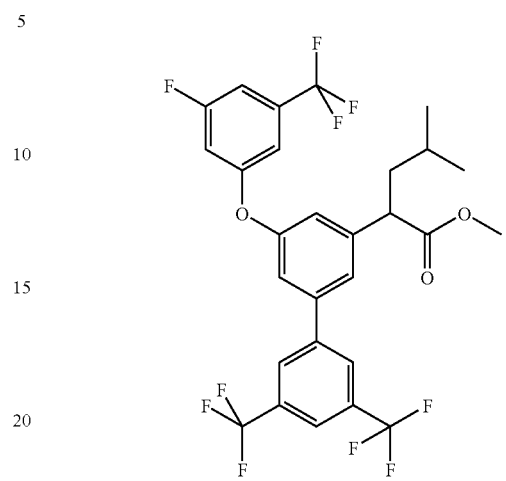

The title compound was prepared in 35% yield from 2-(5-hydroxy-3',5'-bis-trifluoromethyl-biphenyl-3-yl)-4-methyl-pentanoic acid methyl ester (prepared in Example C) and 3-fluoro-5-trifluoromethylphenyl-boronic acid under the conditions described in Example 15, step (g).

b) 2-[5-(3-Fluoro-5-trifluoromethyl-phenoxy)-3',5'-bis-trifluoromethyl-biphenyl-3-yl]-4-methyl-pentanoic acid The title compound was prepared in 61% yield from 2-[5-(3-fluoro-5-trifluoromethyl-phenoxy)-3',5'-bis-trifluoromethyl-biphenyl-3-yl]-4-methyl-pentanoic acid methyl ester under the conditions described in Example 15, step (h).

$^1$H-NMR (400 MHz, CD$_3$Cl): δ 7.96 (s, 2H), 7.89 (s, 1H), 7.38 (s, 1H), 7.18 (d, 2H), 7.08 (d, 2H), 6.89 (d, 1H), 2.66 (s, 2H), 2.03-2.00 (m, 1H), 1.79-1.73 (m, 1H), 1.57-1.53 (m, 1H), 0.94 (d, 6H).

Example 35

2-[3',5'-Bis-trifluoromethyl-5-(3-trifluoromethyl-phenoxy)-biphenyl-3-yl]-4-methyl-pentanoic acid

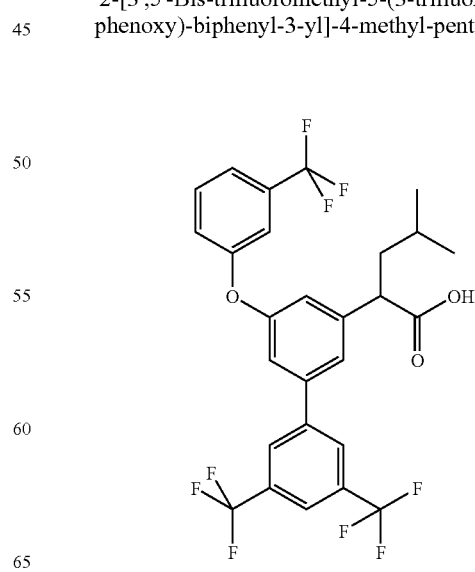

a) 2-[3',5'-Bis-trifluoromethyl-5-(3-trifluoromethyl-phenoxy)-biphenyl-3-yl]-4-methyl-pentanoic acid methyl ester

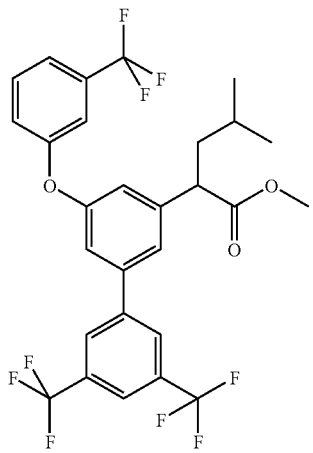

The title compound was prepared in 60% yield from 2-(5-hydroxy-3',5'-bis-trifluoromethyl-biphenyl-3-yl)-4-methyl-pentanoic acid methyl ester (prepared in Example C) and 3-trifluoromethylphenylboronic acid under the conditions described in Example 15, step (g).

b) 2-[3',5'-Bis-trifluoromethyl-5-(3-trifluoromethyl-phenoxy)-biphenyl-3-yl]-4-methyl-pentanoic acid The title compound was prepared in 62% yield from 2-[3',5'-bis-trifluoromethyl-5-(3-trifluoromethyl-phenoxy)-biphenyl-3-yl]-4-methyl-pentanoic acid methyl ester under the conditions described in Example 15, step (h).

$^1$H-NMR (400 MHz, CD$_3$Cl): δ 7.95 (s, 2H), 7.87 (s, 1H), 7.48 (t, 1H), 7.39 (d, 2H), 7.33 (t, 1H), 7.27 (s, 1H), 7.21 (d, 1H), 7.17 (t, 1H), 7.12 (t, 1H), 3.76 (t, 1H), 2.02-1.99 (m, 1H), 1.76-1.69 (m, 1H), 1.58-1.51 (m, 1H), 0.94 (d, 6H).

Example 36

2-[5-(3,5-Difluoro-phenoxy)-3',5'-bis-trifluoromethyl-biphenyl-3-yl]-4-methyl-pentanoic acid

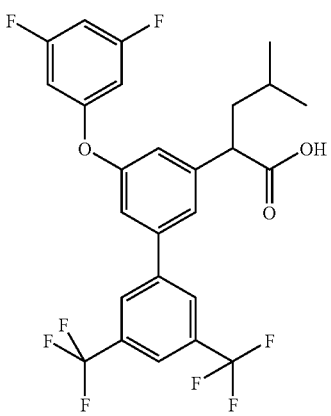

a) 2-[5-(3,5-Difluoro-phenoxy)-3',5'-bis-trifluoromethyl-biphenyl-3-yl]-4-methyl-pentanoic acid methyl ester

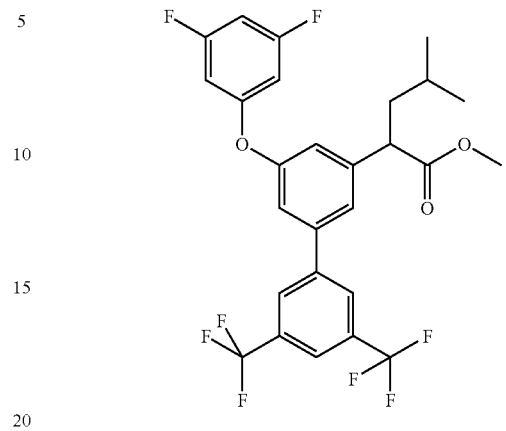

The title compound was prepared in 15% yield from 2-[3',5'-bis-trifluoromethyl-5-(3-trifluoromethyl-phenoxy)-biphenyl-3-yl]-4-methyl-pentanoic acid methyl ester (prepared in Example C) and 3,5-difluoro-phenylboronic acid under the conditions described in Example 15, step (g).

b) 2-[5-(3,5-Difluoro-phenoxy)-3',5'-bis-trifluoromethyl-biphenyl-3-yl]-4-methyl-pentanoic acid The title compound was prepared in 45% yield from 2-[5-(3,5-difluoro-phenoxy)-3',5'-bis-trifluoromethyl-biphenyl-3-yl]-4-methyl-pentanoic acid methyl ester under the conditions described in Example 15, step (h).

$^1$H-NMR (400 MHz, CD$_3$Cl): δ 7.95 (s, 2H), 7.88 (s, 1H), 7.36 (s, 1H), 7.17 (d, 2H), 6.59-6.51 (m, 3H), 2.64 (s, 2H) 2.07-1.98 (m, 1H), 1.78-1.71 (m, 1H), 1.59-1.53 (m, 1H), 0.95 (d, 6H).

Example 37

2-[5-(3,5-Bis-trifluoromethyl-phenylamino)-4'-chloro-3'-trifluoromethyl-biphenyl-3-yl]-4-methyl-pentanoic acid

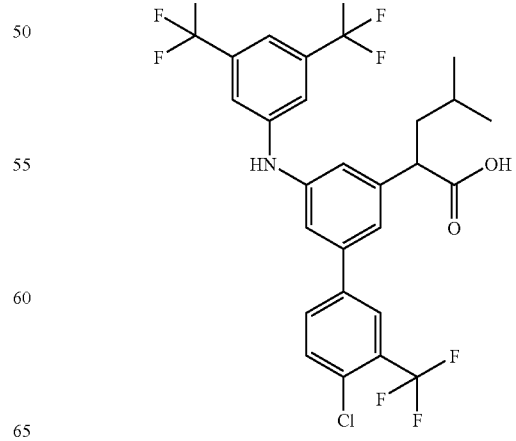

a) 2-(4'-Chloro-5-trifluoromethanesulfonyloxy-3'-trifluoromethyl-biphenyl-3-yl)-4-methyl-pentanoic acid methyl ester

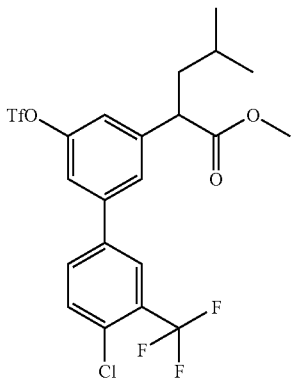

Trifluoromethanesulphonic anhydride (93 μL, 0.57 mmol) was added dropwise to a stirred solution of 2-(4'-chloro-5-hydroxy-3'-trifluoromethyl-biphenyl-3-yl)-4-methyl-pentanoic acid methyl ester (prepared in Example A) (150 mg, 0.38 mmol) and pyridine (88 μL, 1.1 mmol) in DCM (3 mL) at 0° C. The reaction was warmed to room temperature and stirred for 1 h, then 1M hydrochloric acid was added. The organic layer was filtered through a polytetrafluoroethylene (PTFE) frit and concentrated in vacuo to give the title compound (205 mg, 100%) as an orange oil.

b) 2-[5-(3,5-Bis-trifluoromethyl-phenylamino)-4'-chloro-3'-trifluoromethyl-biphenyl-3-yl]-4-methyl-pentanoic acid methyl ester

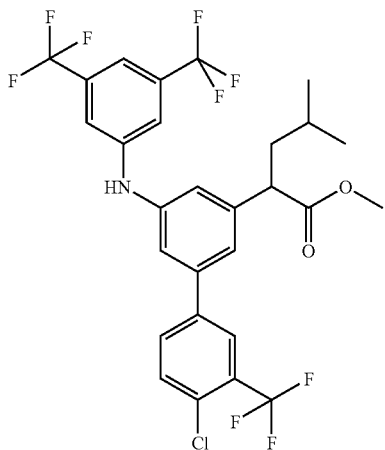

A mixture of 2-(4'-chloro-5-trifluoromethanesulfonyloxy-3'-trifluoromethyl-biphenyl-3-yl)-4-methyl-pentanoic acid methyl ester (48 mg, 0.10 mmol), 3,5-bis-(trifluoromethyl)-aniline (18 μL, 0.12 mmol), sodium tert-butoxide (9.8 mg, 0.10 mmol), Pd(OAc)$_2$ (2.5 mg, 0.01 mmol), 2-(di-tert-butylphoshino-1,1'-binaphthyl (3.5 mg, 0.01 mmol) and toluene (1 mL) was stirred under microwave irradiation at 130° C. for 3×10 min. The mixture was diluted with toluene (9 mL), washed with 1M HCl (2×10 mL) and brine (10 mL), dried (MgSO$_4$), concentrated in vacuo and purified by flash column chromatography (diethylether-petroleum ether) to afford the title product as a colourless powder (28 mg, 44%). Mass spectrum (ESI, m/z): 610, 612 (M–H).

c) 2-[5-(3,5-Bis-trifluoromethyl-phenylamino)-4'-chloro-3'-trifluoromethy 1-biphenyl-3-yl]-4-methyl-pentanoic acid A mixture of 2-[5-(3,5-bis-trifluoromethyl-phenylamino)-4'-chloro-3'-trifluoromethyl-biphenyl-3-yl]-4-methyl-pentanoic acid methyl ester (10 mg, 0.02 mmol), THF (0.6 mL), 10% aq. LiOH (0.2 mL) and MeOH (0.6 mL) was stirred at 30° C. for 3 h. The solution was concentrated and the residue was diluted with H$_2$O (1 mL) and then acidified with concentrated (conc) HCl. The aqueous solution was extracted with DCM (3×1 mL) and the organic layers were filtered through PTFE filter. The solution was concentrated in vacuo to give a solid residue. The solid was purified using reverse phase preparative HPLC (MeCN, H$_2$O) to afford the title compound (3 mg, 30%). Mass spectrum (m/z, ESI) 598, 600 (M+H).

Example 38

2-[4'-Chloro-5-(3-fluoro-5-trifluoromethyl-phenylamino)-3'-trifluoromethyl-biphenyl-3-yl]-4-methyl-pentanoic acid

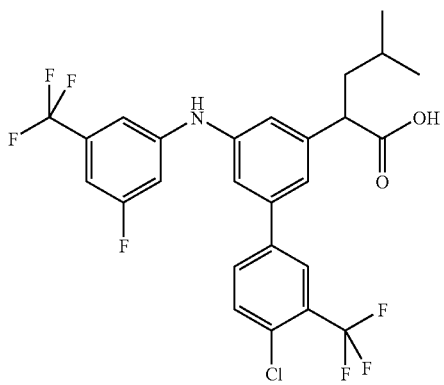

a) 2-[4'-Chloro-5-(3-fluoro-5-trifluoromethyl-phenylamino)-3'-trifluoromethyl-biphenyl-3-yl]-4-methyl-pentanoic acid methyl ester

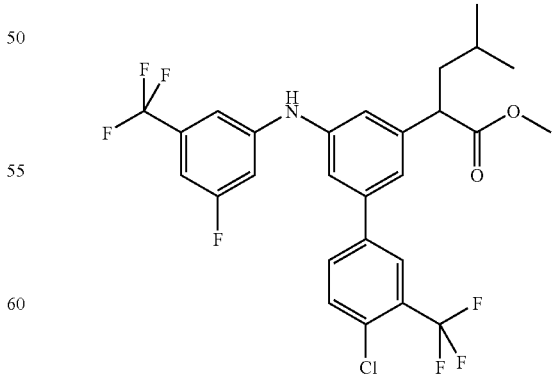

The title compound was prepared in 28% yield from 2-(4'-chloro-5-trifluoromethanesulfonyloxy-3'-trifluoromethyl-biphenyl-3-yl)-4-methyl-pentanoic acid methyl ester and 3-fluoro-5-(trifluoromethyl)aniline under the conditions described in Example 37, step (b). Mass spectrum (ES–, m/z): 560, 562 (M–H);

b) 4-Methyl-2-[4'-trifluoromethyl-5-(4-trifluoromethyl-phenoxy)-biphenyl-3-yl]-pentanoic acid The title compound was prepared in 73% yield from 2-[4'-chloro-5-(3-fluoro-5-trifluoromethyl-phenylamino)-3'-trifluoromethyl-biphenyl-3-yl]-4-methyl-pentanoic acid methyl ester under the conditions described in Example 37, step (c).

$^1$H-NMR (400 MHz, CDCl$_3$): δ 7.80 (br. s, 1H), 7.60 (m, 1H), 7.52 (m, 1H), 7.33 (m, 2H), 7.2-7.1 (m, 3H), 5.93 (br. s, 1H), 3.65 (br. s, 1H), 1.97 (m, 1H), 1.72 (m, 1H), 1.53 (m, 1H), 0.90 (br. s, 6H). Mass spectrum (ES+, m/z): 548, 550 (M+H)

Example 39

2-[4'-Chloro-5-(2,5-bis-trifluoromethyl-phenylamino)-3'-trifluoromethyl-biphenyl-3-yl]-4-methyl-pentanoic acid

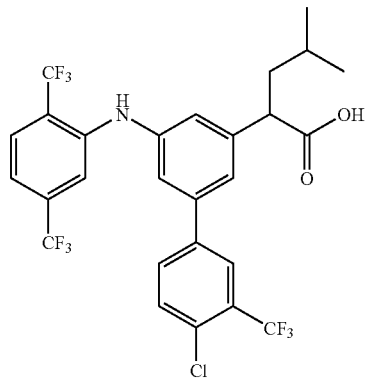

a) 2-[4'-Chloro-5-(2,5-bis-trifluoromethyl-phenylamino)-3'-trifluoromethyl-biphenyl-3-yl]-4-methyl-pentanoic acid methyl ester

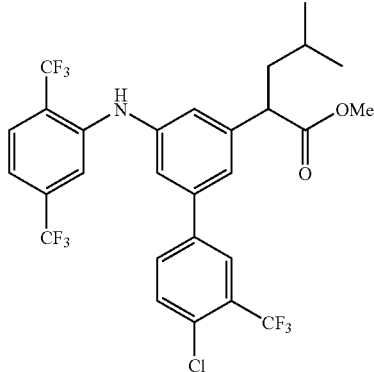

The title compound was prepared in 35% yield from 2-(4'-chloro-5-trifluoromethanesulfonyloxy-3'-trifluoromethyl-biphenyl-3-yl)-4-methyl-pentanoic acid methyl ester and 2,5-bis-(trifluoromethyl)aniline under the conditions described in Example 37, step (b).

b) 2-[4'-Chloro-5-(2,5-bis-trifluoromethyl-phenylamino)-3'-trifluoromethyl-biphenyl-3-yl]-4-methyl-pentanoic acid The title compound was prepared in 86% yield from 2-[4'-chloro-5-(2,5-bis-trifluoromethyl-phenylamino)-3'-trifluoromethyl-biphenyl-3-yl]-4-methyl-pentanoic acid methyl ester under the conditions described in Example 37, step (c).

$^1$H-NMR (400 MHz, CDCl$_3$): δ 7.83 (br s, 1H), 7.69 (d, 1H), 7.63 (d, 1H), 7.57 (m, 2H), 7.19 (m, 3H), 6.31 (br s, 1H), 3.75 (br. s, 1H), 1.98 (m, 1H), 1.76 (m, 1H), 1.54 (m, 1H), 0.93 (br, s, 6H). Mass spectrum (ESI+, m/z): 598, 600 (M+H)

Example 40

2-[5'-Fluoro-5-(2,5-bis-trifluoromethyl-phenylamino)-3'-trifluoromethyl-biphenyl-3-yl]-4-methyl-pentanoic acid

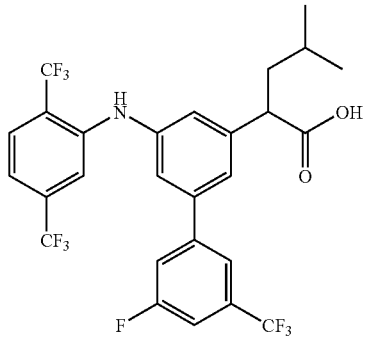

a) 2-(3'-Fluoro-5-trifluoromethanesulfonyloxy-5'-trifluoromethyl-biphenyl-3-yl)-4-methyl-pentanoic acid methyl ester

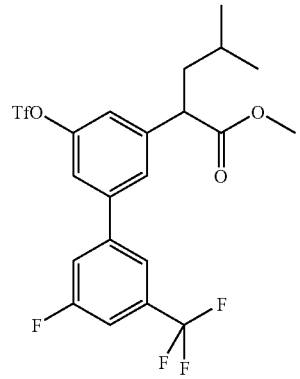

The title compound was prepared in 91% yield from 2-(3'-fluoro-5-hydroxy-5'-trifluoromethyl-biphenyl-3-yl)-4-methyl-pentanoic acid methyl ester (prepared in Example B) under the conditions described in Example 37, step (a).

$^1$H-NMR (400 MHz, CDCl$_3$): δ 7.58; (s, 1H), 7.53 (m, 1H), 7.44 (dm, 1H, J=9.1 Hz), 7.39 (m, 1H), 7.36, (m, 1H), 7.33 (m, 1H), 3.78 (m, 1H), 3.70 (s, 3H), 2.03 (m, 1H), 1.71 (m, 1H), 1.49 (m, 1H), 0.94 (d, 6H, J=6.8 Hz), b) 2-[5'-Fluoro-5-(2,5-bis-trifluoromethyl-phenylamino)-3'-trifluoromethyl-biphenyl-3-yl]-4-methyl-pentanoic acid methyl ester

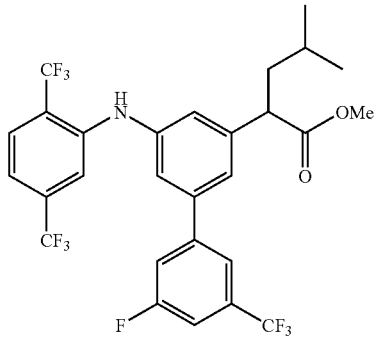

The title compound was prepared in 100% yield from 2-(5'-fluoro-5-trifluoromethanesulfonyloxy-3'-trifluoromethyl-biphenyl-3-yl)-4-methyl-pentanoic acid methyl ester and 2,5-bis-(trifluoromethyl)aniline under the conditions described in Example 37, step (b).

c) 2-[5'-Fluoro-5-(2,5-bis-trifluoromethyl-phenylamino)-3'-trifluoromethyl-biphenyl-3-yl]-4-methyl-pentanoic acid The title compound was prepared in 42% yield from 2-[5'-fluoro-5-(2,5-bis-trifluoromethyl-phenylamino)-3'-trifluoromethyl-biphenyl-3-yl]-4-methyl-pentanoic acid methyl ester under the conditions described in Example 37, step (c).

$^1$H-NMR (400 MHz, CDCl$_3$): δ 7.70 (d, 1H), 7.58 (m, 2H), 7.42 (d, 1H), 7.32 (d, 1H), 7.20 (m, 3H), 6.31 (br s, 1H), 3.75 (m, 1H), 1.98 (m, 1H), 1.75 (m, 1H), 1.55 (m, 1H), 0.93 (m, 6H); Mass spectrum (ESI, m/z): 582 (M+H)

Example 41

2-[5'-Fluoro-5-(4-fluoro-2-trifluoromethyl-phenylamino)-3'-trifluoromethyl-biphenyl-3-yl]-4-methyl-pentanoic acid

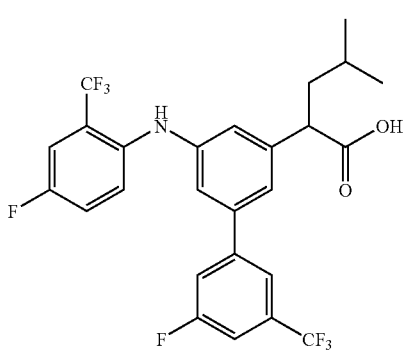

a) 2-[5'-Fluoro-5-(4-fluoro-2-trifluoromethyl-phenylamino)-3'-trifluoromethyl-biphenyl-3-yl]-4-methyl-pentanoic acid methyl ester

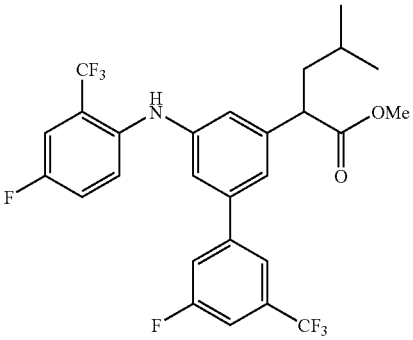

The title compound was prepared in 100% yield from 2-(5'-fluoro-5-trifluoromethanesulfonyloxy-3'-trifluoromethyl-biphenyl-3-yl)-4-methyl-pentanoic acid methyl ester (prepared in Example 40, step (a)) and 4-fluoro-2-(trifluoromethyl)aniline under the conditions described in Example 37, step (b).

b) 2-[5'-Fluoro-5-(4-fluoro-2-trifluoromethyl-phenylamino)-3'-trifluoromethyl-biphenyl-3-yl]-4-methyl-pentanoic acid The title compound was prepared in 82% yield from 2-[5'-fluoro-5-(4-fluoro-2-trifluoromethyl-phenylamino)-3'-trifluoromethyl-biphenyl-3-yl]-4-methyl-pentanoic acid methyl ester under the conditions described in Example 37, step (c).

$^1$H-NMR (400 MHz, CDCl$_3$): δ 7.54 (br s, 1H), 7.41-7.29 (m, 4H), 7.18-7.02 (m, 4H), 5.94 (br s, 1H), 3.75 (1H), 1.99 (1H), 1.73 (1H), 1.56 (1H), 0.93 (6H); Mass spectrum (ESI, m/z): 532 (M+H)

Example 42

2-[5'-Fluoro-5-(3,5-bis-trifluoromethyl-phenylamino)-3'-trifluoromethyl-biphenyl-3-yl]-4-methyl-pentanoic acid

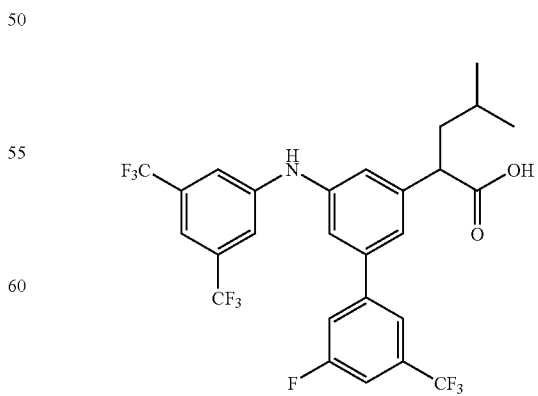

97 a) 2-[5'-Fluoro-5-(3,5-bis-trifluoromethyl-phenylamino)-3'-trifluoromethyl-biphenyl-3-yl]-4-methyl-pentanoic acid methyl ester

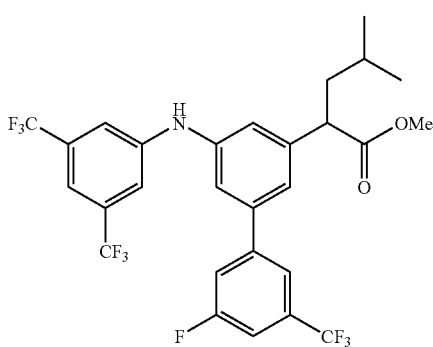

The title compound was prepared in 97% yield from 2-(5'-fluoro-5-trifluoromethanesulfonyloxy-3'-trifluoromethyl-biphenyl-3-yl)-4-methyl-pentanoic acid methyl ester (prepared in Example 40, step (a)) and 3,5-bis-(trifluoromethyl)aniline under the conditions described in Example 37, step (b).

b) 2-[5'-Fluoro-5-(3,5-bis-trifluoromethyl-phenylamino)-3'-trifluoromethyl-biphenyl-3-yl]-4-methyl-pentanoic acid The title compound was prepared in 46% yield from 2-[5'-fluoro-5-(3,5-bis-trifluoromethyl-phenylamino)-3'-trifluoromethyl-biphenyl-3-yl]-4-methyl-pentanoic acid methyl ester under the conditions described in Example 37, step (c).

$^1$H-NMR (400 MHz, CDCl$_3$): δ 7.56 (1H), 7.44-7.35 (m, 4H), 7.32 (d, 1H), 6.12 (1H), 3.78 (1H), 1.96 (1H), 1.78 (1H), 1.53 (1H), 0.92 (1H); Mass spectrum (ESI, m/z): 582 (M+H)

Example 43

2-[5-(3,5-Bis-trifluoromethyl-phenylamino)-3',5'-bis-trifluoromethyl-biphenyl-3-yl]-4-methyl-pentanoic acid

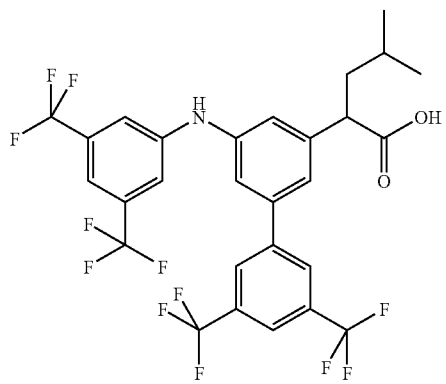

98 a) 4-Methyl-2-(5-trifluoromethanesulfonyloxy-3',5'-bis-trifluoromethyl-bi phenyl-3-yl)-pentanoic acid methyl ester

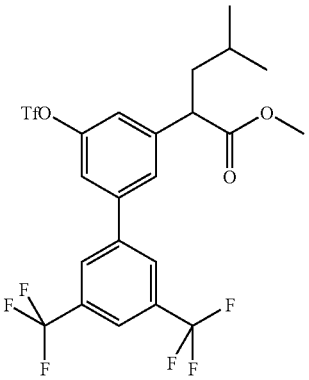

The title compound was prepared in 95% yield from 2-(5-hydroxy-3',5'-bis-trifluoromethyl-biphenyl-3-yl)-4-methyl-pentanoic acid methyl ester (prepared in Example C) under the conditions described in Example 37, step (a)).

$^1$H-NMR (400 MHz, CDCl$_3$): 6$^1$H-NMR (400 MHz, CD$_3$Cl): δ 7.96 (s, 2H), 7.94 (s, 1H), 7.55 (m, 1H), 7.38 (m, 2H), 3.80 (t, 1H), 3.71 (s, 3H), 2.01 (m, 1H), 1.71 (m, 1H), 1.49 (m, 1H), 0.94 (d, 6H).

b) 2-[5-(3,5-Bis-trifluoromethyl-phenylamino)-3',5'-bis-trifluoromethyl-biphenyl-3-yl]-4-methyl-pentanoic acid methyl ester The title compound was prepared in 47% yield from 4-methyl-2-(5-trifluoromethanesulfonyloxy-3',5'-bis-trifluoromethyl-biphenyl-3-yl)-pentanoic acid methyl ester and 3,5-bis-trifluoromethyl-aniline under the conditions described in Example 37, step (b).

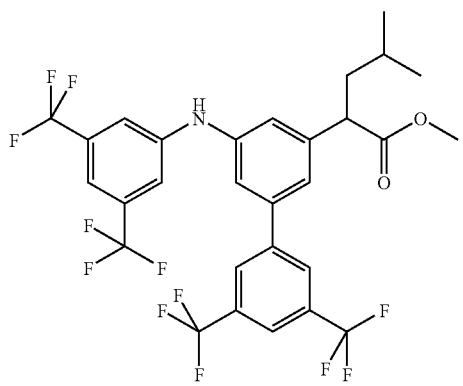

c) 2-[5-(3,5-Bis-trifluoromethyl-phenylamino)-3',5'-bis-trifluoromethyl-biphenyl-3-yl]-4-methyl-pentanoic acid The title compound was prepared in 66% yield from 2-[5-(3,5-bis-trifluoromethyl-phenylamino)-3',5'-bis-trifluoromethyl-biphenyl-3-yl]-4-methyl-pentanoic acid methyl ester under the conditions described in Example 37, step (c).

$^1$H-NMR (400 MHz, CD$_3$Cl): δ 7.95 (s, 2H), 7.88 (s, 1H), 7.44 (s, 2H), 7.39 (s, 1H), 7.25 (d, 1H), 7.23-7.22 (m, 2H), 6.17 (s, 1H), 3.76 (t, 1H), 2.05-1.98 (m, 1H), 1.79-1.72 (m, 1H), 1.62-1.52 (m, 1H), 0.95 (d, 6H).

Example 44

2-[5-(2,5-Bis-trifluoromethyl-phenylamino)-3',5'-bis-trifluoromethyl-biphenyl-3-yl]4-methyl-pentanoic acid

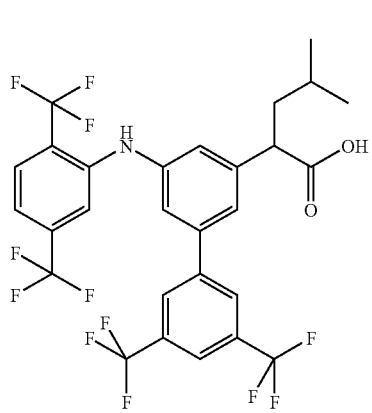

a) 2-[5-(2,5-Bis-trifluoromethyl-phenylamino)-3',5'-bis-trifluoromethyl-biphenyl-3-yl]-4-methyl-pentanoic acid methyl ester

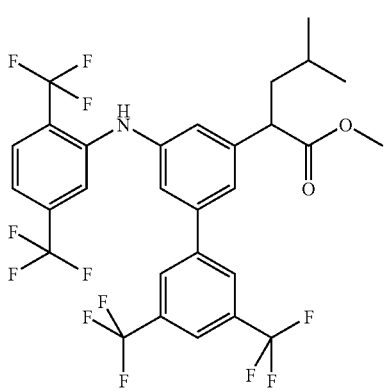

The title compound was prepared in 39% yield from 4-methyl-2-(5-trifluoromethanesulfonyloxy-3',5'-bis-trifluoromethyl-biphenyl-3-yl)-pentanoic acid methyl ester (prepared in Example 43, step (a)) and 2,5-bis-trifluoromethyl-aniline under the conditions described in Example 37, step (b).

b) 2-[5-(2,5-Bis-trifluoromethyl-phenylamino)-3',5'-bis-trifluoromethyl-biphenyl-3-yl]-4-methyl-pentanoic acid The title compound was prepared in 40% yield from 2-[5-(2,5-bis-trifluoromethyl-phenylamino)-3',5'-bis-trifluoromethyl-biphenyl-3-yl]-4-methyl-pentanoic acid methyl ester under the conditions described in Example 37, step (c).

$^1$H-NMR (400 MHz, CD$_3$Cl): δ 7.96 (s, 2H), 7.88 (s, 1H), 7.71 (d, 1H), 7.61 (s, 1H), 7.25 (s, 3H), 7.21 (d, 1H), 6.35 (s, 1H), 3.76 (t, 1H), 2.04-2.00 (m, 1H), 1.78-1.71 (m, 1H), 1.61-1.54 (m, 1H), 0.95 (d, 6H).

Example 45

2-[5-(4-Fluoro-2-trifluoromethyl-phenylamino)-3',5'-bis-trifluoromethyl-biphenyl-3-yl]-4-methyl-pentanoic acid

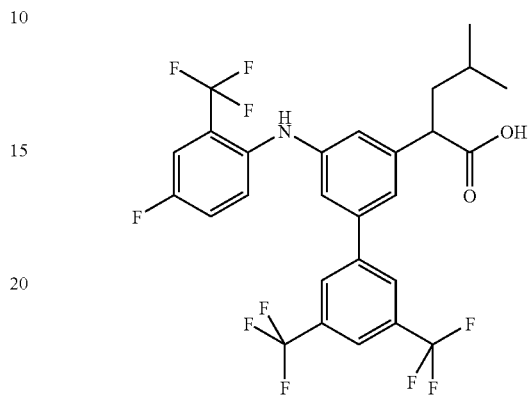

a) 2-[5-(4-Fluoro-2-trifluoromethyl-phenylamino)-3',5'-bis-trifluoromethyl-biphenyl-3-yl]-4-methyl-pentanoic acid methyl ester

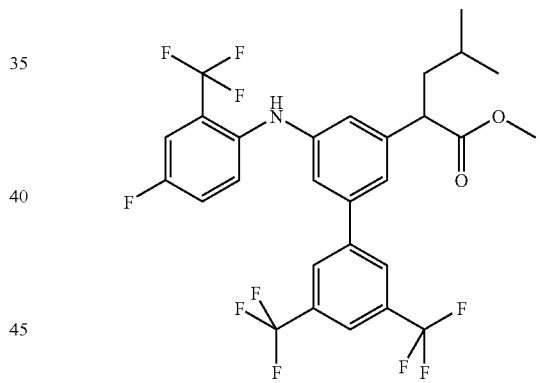

The title compound was prepared in 46% yield from 4-methyl-2-(5-trifluoromethanesulfonyloxy-3',5'-bis-trifluoromethyl-biphenyl-3-yl)-pentanoic acid methyl ester (prepared in Example 43, step (a)) and 4-fluoro-2-trifluoromethyl-aniline under the conditions described in Example 37, step (b).

b) 2-[5-(4-Fluoro-2-trifluoromethyl-phenylamino)-3',5'-bis-trifluoromethyl-biphenyl-3-yl]-4-methyl-pentanoic acid The title compound was prepared in 83% yield from 2-[5-(4-fluoro-2-trifluoromethyl-phenylamino)-3',5'-bis-trifluoromethyl-biphenyl-3-yl]-4-methyl-pentanoic acid methyl ester under the conditions described in Example 37, step (c).

$^1$H-NMR (400 MHz, CD$_3$Cl): δ 7.92 (s, 2H), 7.86 (s, 1H), 7.37-7.33 (m, 2H), 7.16-7.06 (m, 4H), 5.96 (s, 1H), 3.71 (t, 1H), 2.05-1.96 (m, 1H), 1.74-1.67 (m, 1H), 1.61-1.53 (m, 1H), 0.94 (d, 6H).

Example 46

(R)2-[5-(2,5-Bis-trifluoromethyl-phenylamino)-4'-trifluoromethyl-biphenyl-3-yl]-4-methyl-pentanoic acid

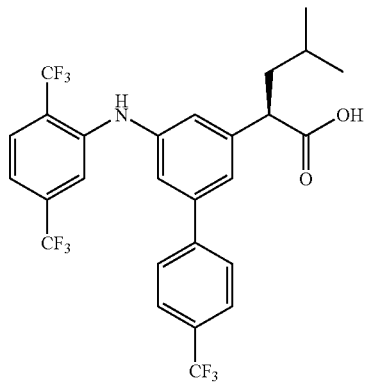

a) 5-Benzyloxy-4'-trifluoromethyl-biphenyl-3-yl)-acetic acid

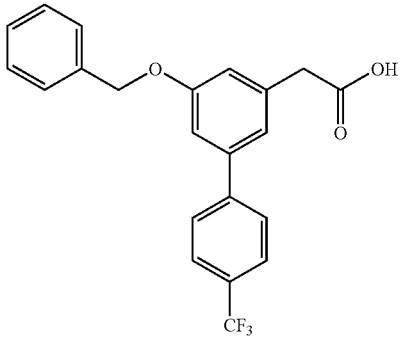

To a solution of (5-benzyloxy-4'-trifluoromethyl-biphenyl-3-yl)-acetic acid ethyl ester (120 g, 0.29 mol) in THF (1.2 L) was added water (240 mL), LiOH.H$_2$O (16 g, 0.32 mol) and the resulting mixture was stirred at room temperature for 16 h. The solution was filtered and concentrated in vacuo to remove THF. The resulting thick liquid was acidified to pH 2 by adding 2N aqueous HCl solution and the white suspension was mechanically stirred for 1 h at room temperature. The wet white product was recovered after filtration and dissolved in EtOAc (500 mL). The organic layer was separated from water, dried (MgSO$_4$) and concentrated in vacuo to obtain (5-benzyloxy-4'-trifluoromethyl-biphenyl-3-yl)-acetic acid (105 g, 94%).

$^1$H-NMR (d$_6$-DMSO): δ 3.64 (s, 2H), 5.18 (s, 2H), 7.02 (s, 1H), 7.24 (d, 2H), 7.34-7.50 (m, 5H), 7.81 (d, 2H), 7.89 (d, 2H), 12.25 (bs, 0.6H); Calcd for C22H17F3O3 (M+H) 387.11, Found 387.1.

b) 4-Benzyl-3-[2-(5-benzyloxy-4'-trifluoromethyl-biphenyl-3-yl)-acetyl]-oxazolidin-2-one

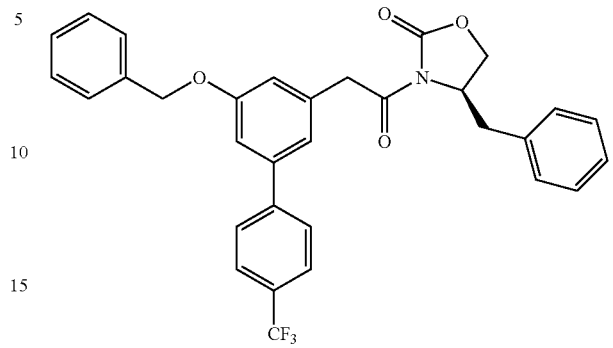

To a mechanically stirred solution of (5-benzyloxy-4'-trifluoromethyl-biphenyl-3-yl)-acetic acid (20 g, 52 mmol) in THF (104 mL) at −78° C. was added N-methyl morpholine (NMM) (6.3 mL, 57 mmol) and trimethylacetyl chloride (7.0 mL, 57 mmol) maintaining the internal temperature below −70° C. This mixture was stirred at −78° C. for 15 minute and 0° C. at 1 h. The white solid was filtered off to receive the anhydride in the filtrate which was cooled back to −78° C. In a separate flask, to a solution of (R)-(+)-4-benzyl-2-oxazolidinone (9.6 g, 54.4 mmol) in THF (109 mL) at −78° C. was added nBuLi (1.6M in hexanes, 34 mL, 54.4 mol), drop-wise, maintaining the internal temperature below −70° C. and stirred at −78° C. for 45 min. This metalated chiral auxiliary was cannulated to the anhydride at −78° C. and warmed to 0° C. over 1.5 h. The resulting mixture was stirred further at 0° C. for 30 minute and quenched by adding excess saturated aqueous NH$_4$Cl solution. The solution was diluted with EtOAc (200 mL) and the organic phase was washed with saturated aqueous NaHCO$_3$ solution (3×100 mL) and brine (2×100 mL). The solution was dried over MgSO$_4$ and the solvent was removed in vacuo. The crude material was purified by ISCO silica gel column chromatography to yield 20.3 g (72%) of 4-benzyl-3-[2-(5-benzyloxy-4'-trifluoromethyl-biphenyl-3-yl)-acetyl]-oxazolidin-2-one as a white solid.

$^1$H-NMR (CDCl$_3$): δ 2.76 (dd, 1H), 3.26 (dd, 1H), 4.19 (m, 2H), 4.35 (q, 2H), 4.69 (m, 1H), 5.13 (s, 2H), 7.04-7.46 (m, 13H), 7.67 (s, 4H); Calcd for C32H26F3NO4 (M+H) 546.18, Found 546.3.

c) 4-Benzyl-3-[2-(5-benzyloxy-4'-trifluoromethyl-biphenyl-3-yl)-4-methyl-pent-4-enoyl]-oxazolidin-2-one

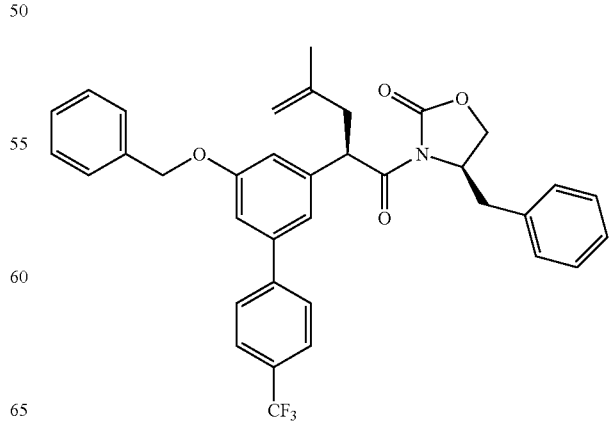

To a colorless solution of 4-benzyl-3-[2-(5-benzyloxy-4'-trifluoromethyl-biphenyl-3-yl)-acetyl]-oxazolidin-2-one (6.0 g, 11.00 mmol) in dry THF (22 mL) at −78° C. was added sodium hexamethyl disilazide (NaHMDS) (1 M in THF solution, 12.11 mL, 12.11 mmol), drop-wise, maintaining the internal temperature below −75° C. The resulting red solution was stirred at −78° C. for 30 minutes. To this was added 3-bromo-2-methyl propene (4.44 mL, 44 mmol) maintaining the temperature below −75° C. When the addition was at near completion, the system turned to green. At this point the dry-ice bath was quickly removed and replaced with wet-ice bath and completed the addition. The reaction mixture was stirred further at 0° C. for 30 min and quenched with saturated aqueous NH$_4$Cl solution. The system was diluted with EtOAC (100 mL) and the organic phase was washed with saturated aqueous NaHCO$_3$ solution (3×50 mL) and dried (MgSO$_4$). Solvent was removed in vacuo and the crude mixture was purified by ISCO silica gel column to yield 4-benzyl-3-[2-(5-benzyloxy-4'-trifluoromethyl-biphenyl-3-yl)-4-methyl-pent-4-enoyl]-oxazolidin-2-one (6.3 g, 95%).

$^1$H-NMR (CDCl$_3$): δ 1.80 (s, 3H), 2.46 (dd, 1H), 2.75 (dd, 1H), 3.05 (dd, 1H), 3.32 (dd, 1H), 4.08 (m, 2H), 4.59 (m, 1H), 4.80 (d, 2H), 5.13 (s, 2H), 5.48 (dd, 1H), 7.11 (d, 2H), 7.21-7.49 (m, 11H), 7.67 (s, 4H); Calcd for C36H32F3NO4 (M+H) 600.23, Found 600.3.

d) 4-Benzyl-3-[2-(5-hydroxy-4'-trifluoromethyl-biphenyl-3-yl)-4-methyl-pentanoyl]-oxazolidin-2-one

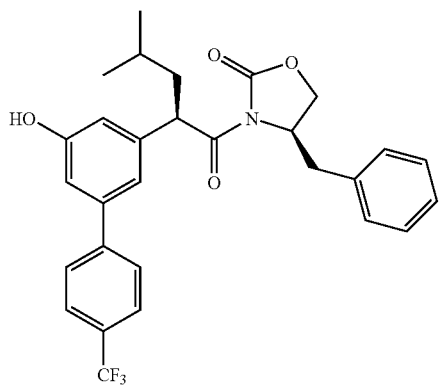

To a solution of 4-benzyl-3-[2-(5-benzyloxy-4'-trifluoromethyl-biphenyl-3-yl)-4-methyl-pent-4-enoyl]-oxazolidin-2-one (6.7 g, 11.2 mmol) in MeOH (150 mL) was added 10% Pd/C (670 mg, 10 w %). The black suspension was hydrogenated at 45-45 psi overnight. The mixture was filtered through celite and the solvent was removed in vacuo to obtain relatively pure 4-benzyl-3-[2-(5-hydroxy-4'-trifluoromethyl-biphenyl-3-yl)-4-methyl-pentanoyl]-oxazolidin-2-one (5.4 g, 93%).

$^1$H-NMR (CDCl$_3$): δ 0.94 (d, 3H), 0.98 (d, 3H), 1.54 (m, 1H), 1.74 (m, 1H), 2.12 (m, 1H), 2.79 (dd, 1H), 3.36 (dd, 1H), 4.11 (m, 2H), 4.62 (m, 1H), 5.25 (t, 1H), 6.97 (m, 2H), 7.21-7.37 (m, 6H), 7.67 (s, 4H); Calcd for C29H28F3NO4 (M+H) 512.20, Found 512.3.

e) Trifluoro-methanesulfonic acid 5-[1-(4-benzyl-2-oxo-oxazolidine-3-carbonyl)-3-methyl-butyl]-4'-trifluoromethyl-biphenyl-3-yl ester

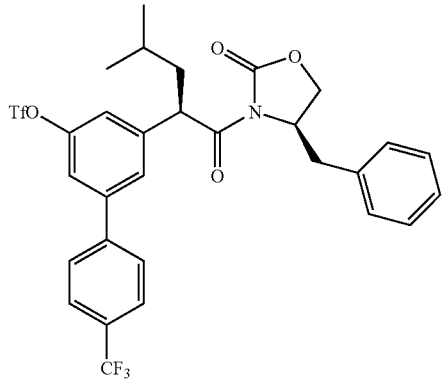

To a solution of 4-benzyl-3-[2-(5-hydroxy-4'-trifluoromethyl-biphenyl-3-yl)-4-methyl-pentanoyl]-oxazolidin-2-one (32 g, 62.6 mmol) in dichloromethane (170 mL) was added pyridine (15.0 mL). The system was cooled to 0° C. To this cold solution was added trifluoromethanesulfonic anhydride (16 mL, 94 mmol) maintaining the internal temperature below 5° C. and stirred for further 0.5 h at 0° C. This reaction mixture was poured to a mixture of 1 N HCl (100 mL), and wet-ice (25 g) and stirred for 0.5 h. The aqueous layer was extracted with dichloromethane (2×100 mL). Combined fractions were washed with water (2×100 mL), saturated aqueous NaHCO$_3$ solution (2×100 mL), and brine (2×100 mL). The organics were dried (MgSO$_4$) and concentrated in vacuo to receive a reddish liquid which was purified by ISCO column chromatography to receive trifluoro-methanesulfonic acid 5-[1-(4-benzyl-2-oxo-oxazolidine-3-carbonyl)-3-methyl-butyl]-4'-trifluoromethyl-biphenyl-3-yl ester (34 g, 84%).

$^1$H-NMR (CDCl$_3$): δ 0.96 (d, 3H), 0.98 (d, 3H), 1.52 (m, 1H), 1.77 (m, 1H), 2.13 (m, 1H), 2.79 (dd, 1H), 3.37 (dd, 1H), 4.14 (m, 2H), 4.67 (m, 1H), 5.33 (t, 1H), 7.20-7.38 (m, 7H), 7.70 (m, 5H); Calcd for C30H27F6NO6S (M+H) 644.15, Found 644.2.

f) 4-Benzyl-3-{2-[5-(2,5-bis-trifluoromethyl-phenylamino)-4'-trifluoromethyl-biphenyl-3-yl]-4-methyl-pentanoyl}-oxazolidin-2-one

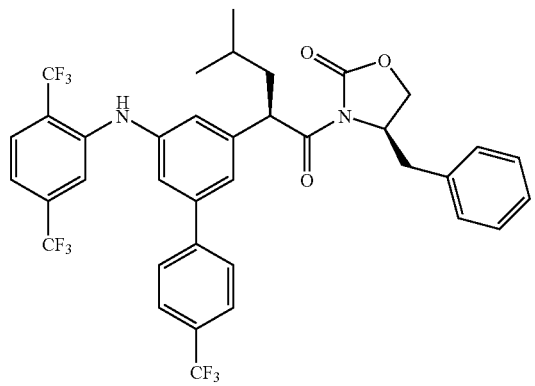

To a solution of trifluoro-methanesulfonic acid 5-[1-(4-benzyl-2-oxo-oxazolidine-3-carbonyl)-3-methyl-butyl]-4'-trifluoromethyl-biphenyl-3-yl ester (4.84 g, 7.53 mmol) in toluene (38 mL) in a sealed tube was added 2,5-bis-trifluoromethyl-phenylamine (1.42 mL, 9.04 mmol), [1,1']binaphthalenyl-2-yl-di-tert-butyl-phosphane (300 mg, 0.75 mmol), Pd(OAc)$_2$ (169 mg, 0.75 mmol) and KOtBu (7.53 mL of 1.0 M solution in THF, 7.53 mmol). The reaction mixture was heated to 120° C. for 1 h. To this was added another portion each of [1,1']binaphthalenyl-2-yl-di-tert-butyl-phosphane (300 mg, 0.75 mmol), Pd(OAc)$_2$ (169 mg, 0.75 mmol) and KOtBu (3.77 mL of 1.0 M solution in THF, 3.77 mmol) and heated for further 1 h. The system was cooled to room temperature and quenched by slow addition of water. The mixture was extracted with EtOAc (3×50 mL). The organic phase was washed with saturated NaHCO$_3$ solution and brine. The organic fraction was dried (Na$_2$SO$_4$) and concentrated in vacuo. The crude mixture was purified by ISCO column chromatography to obtain. 4-benzyl-3-{2-[5-(2,5-bis-trifluoromethyl-phenylamino)-4'-trifluoromethyl-biphenyl-3-yl]-4-methyl-pentanoyl}-oxazolidin-2-one (2.32 g, 43%).

$^1$H-NMR (CDCl$_3$): δ 0.97 (d, 3H), 0.99 (d, 3H), 1.56 (m, 1H), 1.76 (m, 1H), 2.10 (m, 1H), 2.78 (dd, 1H), 3.37 (dd, 1H), 4.14 (m, 2H), 4.65 (m, 1H), 5.28 (t, 1H), 6.32 (s, 1H), 7.17-7.40 (m, 9H), 7.59 (s, 1H), 7.69 (m, 5H); Calcd for C37H31F9N2O3 (M+H) 723.22, Found 723.3.

g) (R)-2-[5-(2,5-Bis-trifluoromethyl-phenylamino)-4'-trifluoromethyl-biphenyl-3-yl]-4-methyl-pentanoic acid To a solution of 4-benzyl-3-{2-[5-(2,5-bis-trifluoromethyl-phenylamino)-4'-trifluoromethyl-biphenyl-3-yl]-4-methyl-pentanoyl}-oxazolidin-2-one (2.55 g, 3.53 mmol) in THF (15 mL) was added water (5 mL). The system was cooled to 0° C. To this cold solution was added LiOH.H$_2$O (148 mg, 3.53 mmol) and 30% H$_2$O$_2$ (1.20 mL, 10.59 mmol,) and stirred at 0° C. for 15 min. The excess H$_2$O$_2$ was quenched by adding 1.5 M aqueous Na$_2$SO$_3$ solution (7.06 mL, 10.59 mmol) and stirred at room temperature for 10 min. The organic solvent was removed in vacuo. The resulting liquid was acidified to pH=2 by adding 1 N aqueous HCl solution. The aqueous layer was extracted with EtOAc (3×50 mL) and dried (MgSO$_4$). The mixture was concentrated in vacuo to receive a crude mixture which was purified by ISCO silica gel column chromatography to yield (R) 2-[5-(2,5-Bis-trifluoromethyl-phenylamino)-4'-trifluoromethyl-biphenyl-3-yl]-4-methyl-pentanoic acid (1.15 g, 58%).

$^1$H-NMR (CDCl$_3$): δ 0.94 (d, 6H), 1.56 (m, 1H), 1.76 (m, 1H), 2.00 (m, 1H), 3.74 (t, 1H), 6.32 (s, 1H), 7.17-7.29 (m, 4H), 7.60 (s, 1H), 7.67 (m, 5H); Calcd for C27H22F9NO2 (M+H) 564.15, Found 564.3.

Determination of the Effect of the Compounds According to the Invention on cyclooxygenase-1 and cyclooxygenase-2 (Cox-1, Cox-2)

Inhibition of Cox-1 and Cox-2 was determined using the Colorimetric Cox inhibitor screening assay provided by Cayman Chemical Company, Ann Arbor, Mich., USA. (Cat. No. 760111) according to manufacturer's instructions.

Compounds of the invention will show <50% inhibition at 100 μM.

Screening of the Compounds of the Invention for γ-Secretase-Modulating Activity

Screening was carried out using SKNBE2 cells carrying the APP 695-wild type, grown in DMEM/NUT-mix F12 (HAM) provided by Gibco (cat no. 31330-38) containing 5% Serum/Fe supplemented with 1% non-essential amino acids.

Cells were grown to near confluency.

The screening was performed using the assay as described in Citron et al (1997) Nature Medicine 3: 67.

IC50-Values of Selected Compounds of the Invention on the γ-Secretase Activity.

Activity range: 10-100 uM
2-(5-(4-fluorophenoxy)-4'-trifluoromethyl-biphenyl-3-yl)-pentanoic acid; (example I)
2-(5-(phenoxy)-4'-trifluoromethyl-biphenyl-3-yl)-pentanoic acid; (example ii)

| Compound # | WTAPP SKNBE2 Aβ 42 EC$_{50}$, μM | WTAPP SKNBE2 Aβ 42 % Inhibition at 3 μM |
|---|---|---|
| 1 | | 73 |
| 2 | | 62 |
| 3 | 0.30 | |
| 4 | 0.29 | |
| 5 | | 79 |
| 6 | | 66 |
| 7 | 0.42 | |
| 8 | 0.20 | |
| 9 | 0.28 | |
| 10 | 0.41 | |
| 11 | 0.50 | |
| 12 | | 81 |
| 13 | | 52 |
| 14 | | 17 |
| 15 | | 65 |
| 16 | 2.25 | |
| 17 | 1.85 | |
| 18 | | 19 |
| 19 | | 22 |
| 20 | 0.66 | |
| 21 | 0.14 | |
| 22 | | 81 |
| 23 | | 80 |
| 24 | | 45 |
| 25 | | 54 |
| 26 | | 58 |
| 27 | 0.77 | |
| 28 | | -3 |
| 29 | | 62 |
| 30 | 0.33 | |
| 31 | | 84 |
| 32 | | 87 |
| 33 | | 59 |
| 34 | 0.26 | |
| 35 | | 90 |
| 36 | | 90 |
| 37 | 0.46 | |
| 38 | 0.11 | |
| 39 | | 95 |
| 40 | 0.33 | |
| 41 | | 67 |
| 42 | | 75 |
| 43 | | 89 |
| 44 | 0.24 | |
| 45 | | 85 |
| 46 | 0.10 | |

Demonstration of In Vivo Efficacy

Aβ42 lowering agents of the invention can be used to treat AD in mammals such as humans or alternatively in a validated animal model such as the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD Aβ42 lowering agents can be administered in any standard form using any standard method. For example, but not limited to, Aβ42 lowering agents can be in the form of liquid, tablets or capsules that are taken orally or by injection. Aβ42 lowering agents can be administered at any dose that is sufficient to significantly reduce levels of Aβ42 in the blood, blood plasma, serum, cerebrospinal fluid (CSF), or brain.

To determine whether acute administration of an Aβ42 lowering agent would reduce Aβ42 levels in vivo, non-transgenic rodents, e.g. mice or rats can be used. Alternatively, two to three month old Tg2576 mice expressing APP695 containing the "Swedish" variant can be used or a transgenic mouse model developed by Dr. Fred Van Leuven (K. U. Leuven, Belgium) and co-workers, with neuron-specific expression of a clinical mutant of the human amyloid precursor protein [V717I] (Moechars et al., 1999 J. Biol. Chem. 274, 6483). The single transgenic mouse displays spontaneous, progressive accumulation of β-amyloid (Aβ) in the brain, eventually resulting in amyloid plaques within subiculum, hippocampus and cortex. Animals of this age have high levels of Aβ in the brain but no detectable Aβ deposition. Mice treated with the Aβ42 lowering agent will be examined and compared to those untreated or treated with vehicle and brain levels of soluble Aβ42 and total Aβ would be quantitated by standard techniques, for example, using ELISA. Treatment periods may vary from hours to days and will be adjusted based on the results of the Aβ42 lowering once a time course of onset of effect can be established.

A typical protocol for measuring Aβ42 lowering in vivo is shown but it is only one of many variations that could be used to optimize the levels of detectable Aβ. For example, aliquots of compounds can be dissolved in DMSO (volume equal to 1/10th of the final formulation volume), vortexed and further diluted (1:10) with a 10% (w/v) hydroxypropyl β cyclodextrin (HBC, Aldrich, Ref No 33,260-7) solution in PBS, where after they are sonicated for 20 seconds.

Aβ42 lowering agents may be administered as a single oral dose given three to four hours before sacrifice and analysis or alternatively could be given over a course of days and the animals sacrificed three to four hours after the final dose is given.

Blood is collected at sacrifice. The blood collection is performed via a heart puncture during anesthesia with a mixture of Ketalar (Ketamin), Rompun (Xylazin 2%) and Atropin (2:1:1) and collected in EDTA treated collection tubes. Blood is centrifuged at 4000 g for 5 minutes at 4° C. and the plasma recovered for analysis.

The mice are anaesthetized with a mixture of Ketalar (Ketamin), Rompun (Xylazin 2%) and Atropin (2:1:1) and flushed trans-cardially with physiological serum at 4° C.

The brain is removed from the cranium and hindbrain and forebrain are separated with a cut in the coronal/frontal plane. The cerebellum is removed. The forebrain is divided evenly into left and right hemisphere by using a midline sagital cut.

One hemisphere is immediately immersed in liquid nitrogen and stored at −70° C. until homogenization for biochemical assays.

Brains are homogenized using a Potter, a glass tube (detergent free, 2 cm$^3$) and a mechanical homogenizer (650 rpm). A volume of 6.5×½ brain weight of freshly prepared 20 mM Tris/HCl buffer (pH 8.5) with Proteinase Inhibitors (1 tablet per 50 ml Tris/HCl buffer, Complete™, Roche, Mannheim, Germany) is used as homogenization buffer.

Samples are transferred from −70° C. into a sample holder with liquid nitrogen and each individual sample is pre-warmed by incubation on the bench for a few seconds prior to homogenization. The homogenates are collected in Beckman centrifuge tubes TLX and collected on ice prior to centrifugation. Between two samples, the Potter and the glass tube are rinsed carefully with distilled water without detergents and dried with absorption paper.

Samples are centrifuged in a pre-cooled ultracentrifuge (Beckman, Mannheim, Germany) for 1 hour and 20 minutes at 48000 rpm (135.000×g) at 4° C. The supernatant (soluble fraction containing secreted APP and amyloid peptides) is separated from the pellet (membrane fraction containing membrane-bound APP-fragments and plaque-associated amyloid peptides in case of aged mice).

Small reversed phase columns (C18-Sep-Pack Vac 3 cc cartridges, Waters, Mass.) are mounted on a vacuum system and washed with 80% acetonitrile in 0,1% Trifluoroacetic acid (A-TFA) followed with 0.1% TFA twice. Then the samples are applied and the columns are washed successively with 5% and 25% A-TFA. Amyloid peptides are eluted with 75% A-TFA and the eluates are collected in 2 ml tubes on ice. Eluates are freeze-dried in a speedvac concentrator (Savant, Farmingdale, N.Y.) overnight and resolved in 240 μl of the sample diluent furnished with the ELISA kits.

To quantify the amount of human Aβ-42 in the soluble fraction of the brain homogenates, commercially available Enzyme-Linked-Immunosorbent-Assay (ELISA) kits are used (h Amyloid β42 ELISA high sensitive, The Genetics Company, Zurich, Switzerland). The ELISA is performed according to the manufacturer's protocol. Briefly, the standard (a dilution of synthetic Aβ1-42) and samples are prepared in a 96-well polypropylene plate without protein binding capacity (Greiner bio-one, Frickenhausen, Germany). The standard dilutions with final concentrations of 1000, 500, 250, 125, 62.5, 31.3 and 15.6 pg/ml and the samples are prepared in the sample diluent, furnished with the ELISA kit, to a final volume of 60 μl. Samples, standards and blancs (50 μl) are added to the anti-Aβ-coated polystyrol plate (capture antibody selectively recognizes the C-terminal end of the antigen) in addition with a selective anti-Aβ-antibody conjugate (biotinylated detection antibody) and incubated overnight at 4° C. in order to allow formation of the antibody-Amyloid-antibody-complex. The following day, a Streptavidine-Peroxidase-Conjugate is added, followed 30 minutes later by an addition of TMB/peroxide mixture, resulting in the conversion of the substrate into a colored product. This reaction is stopped by the addition of sulfuric acid (IM) and the color intensity is measured by means of photometry with an ELISA-reader with a 450 nm filter. Quantification of the Abeta content of the samples is obtained by comparing absorbance to a standard curve made with synthetic Aβ1-42.

In such a model at least 20% Aβ42 lowering compared to untreated animals would be advantageous.

In Vivo Data

Oral dose 30 mg/kg at 4 hr time point

| Compound # | JNJ# | Mouse Efficacy % Lowering Aβ 42 | Rat Efficacy % Lowering Aβ 42 |
|---|---|---|---|
| 21 | 40364662 | 25 | na |
| 30 | 40333709 | 43 | na |
| 46 | 40361113 | 18 | 30 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All publications disclosed in the above specification are hereby incorporated by reference in full.

The invention claimed is:

1. A compound having the general Formula (I)

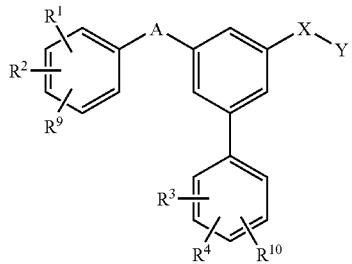

wherein

A is O, NH, S;

X is a bond or a group —CR$_5$R$_6$ wherein R$_5$ and R$_6$ are, independently of each other, selected from the group consisting of H; alkyl selected from the group CH$_3$, C$_2$H$_5$, i-C$_3$H$_7$, n-C$_3$H$_7$, i-C$_4$H$_9$, n-C$_4$H$_9$, sec-C$_4$H$_9$, tert-C$_4$H$_9$; alkenyl selected from C$_2$H$_3$, i-C$_3$H$_5$, n-C$_3$H$_5$, n-C$_4$H$_7$, i-C$_4$H$_7$, sec-C$_4$H$_7$; wherein in any of the alkyl or alkenyl groups one or more H atoms optionally can be substituted with one or more substituents independently selected from the group consisting of OH, F, Cl, Br, I and CF$_3$; or R$_5$, R$_6$ may jointly form together with the carbon atom to which they are attached a ring, either saturated or unsaturated, substituted or unsubstituted, having 3 to 6 C-atoms, and which may contain in the ring one or more heteroatoms from the group N, S or O, and which heteroatom may be identical or different if more than one heteroatom is present;

R$_1$, R$_2$, R$_3$ and R$_4$ are independently selected from the group consisting of H; F; Cl; Br; I; CN; OH; C(O)N (R$_7$R$_8$); S(O)$_2$R$_7$; SO$_2$N(R$_7$R$_8$); S(O)N(R$_7$R$_8$); N(R$_7$)S (O)$_2$R$_8$; N(R$_8$)S(O)R$_8$; S(O)$_2$R$_7$; N(R$_7$)S(O)$_2$N(R$_8$R$_{8a}$); SR$_7$; N(R$_7$R$_8$); N(R$_7$)C(O)R$_8$; N(R$_7$)C(O)N(R$_8$R$_{8a}$); N(R$_7$)C(O)OR$_8$; OC(O)N(R$_7$R$_8$); C(O)R$_7$; substituted and unsubstituted C$_1$-C$_4$-alkyl and substituted and unsubstituted C$_1$-C$_4$-alkoxy, and wherein the substituents of both groups C$_1$-C$_4$-alkyl and C$_1$-C$_4$-alkoxy are selected from F, Cl, Br, I, CF$_3$;

R$_7$, R$_8$, R$_{8a}$ are independently selected from the group consisting of H; C$_1$-C$_4$-alkyl; heterocyclyl; and C$_{3-7}$ cycloalkyl, wherein C$_1$-C$_4$-alkyl; heterocyclyl; and C$_{3-7}$ cycloalkyl are optionally substituted with one or more substituents independently selected from the group consisting of F, Cl, Br, I and CF$_3$;

Y is a carboxy group —C(O)OH or a substututed or unsubstituted tetrazole group;

R$_9$, and R$_{10}$ are independently H, F, or CF$_3$;

and solvates, hydrates, esters, and pharmaceutically acceptable salts thereof.

2. A compound according to claim 1, wherein:

A is O or NH;

X is —CR$_5$R$_6$ wherein R$_5$ and R$_6$ are independently selected from the group consisting of H, CH$_3$, C$_2$H$_5$, i-C$_3$H$_7$, n-C$_3$H$_7$, i-C$_4$H$_9$, n-C$_4$H$_9$, sec-C$_4$H$_9$, and tert-C$_4$H$_9$; wherein in any of the alkyl groups one or more H atoms optionally can be substituted with one or more substituents independently selected from the group consisting of OH, F, Cl, Br and I; or R$_5$, R$_6$ jointly form together with the carbon atom to which they are attached a cyclopropyl ring;

R$_1$, R$_2$, R$_3$ and R$_4$ are independently selected from the group consisting of H, OH, C$_{(1-4)}$alkyl, C$_{(1-4)}$alkoxy, —N(CH$_3$)$_2$, —SO$_2$CH$_3$, CN, OCF$_3$, —C(O)CH$_3$, OCH$_3$, CF$_3$, F, and Cl; wherein said C$_{(1-4)}$alkyl and C$_{(1-4)}$alkoxy are optionally independently substituted with one, two, or three substituents selected from the group consisting of I, Br, F, and Cl;

Y is CO$_2$H;

and solvates, hydrates, esters, and pharmaceutically acceptable salts thereof.

3. A compound according to claim 2, wherein:

X is —CR$_5$R$_6$ wherein R$_5$ and R$_6$ are H, CH$_3$, C$_2$H$_5$, i-C$_3$H$_7$, n-C$_3$H$_7$, i-C$_4$H$_9$, n-C$_4$H$_9$, sec-C$_4$H$_9$, or tert-C$_4$H$_9$;

and solvates, hydrates, esters, and pharmaceutically acceptable salts thereof.

4. A compound according to claim 3, wherein:

R$_1$, and R$_2$ are independently selected from the group consisting of CF$_3$, H, F, Cl, OCH$_3$, C$_{(1-4)}$alkyl, and CN.

R$_3$ and R$_4$ are independently selected from the group consisting of H, CF$_3$, F, and Cl;

R$_9$ is H or F;

R$_{10}$ is H;

and solvates, hydrates, esters, and pharmaceutically acceptable salts thereof.

5. A compound selected from the group consisting of 2-(5-(4-fluorophenoxy)-4'-trifluoromethyl-biphenyl-3-yl)-pentanoic acid;

2-(5-(phenoxy)-4'-trifluoromethyl-biphenyl-3-yl)-pentanoic acid and solvates, hydrates, esters, and pharmaceutically acceptable salts thereof.

6. A compound selected from the group consisting of:

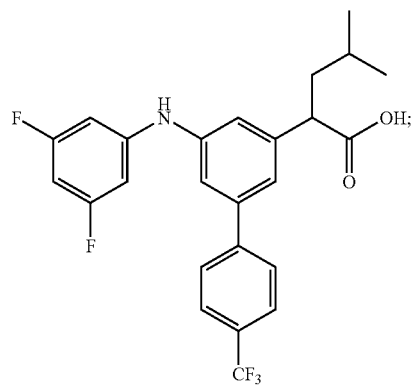

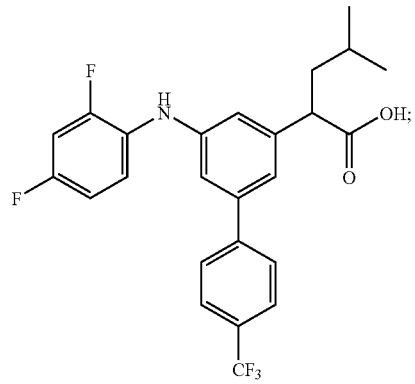

-continued
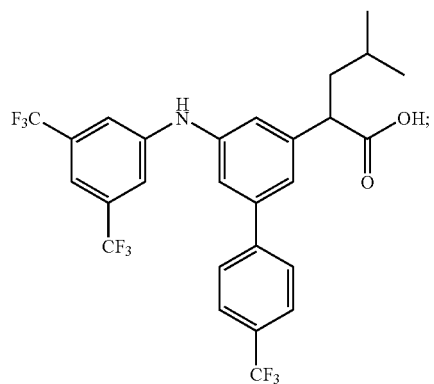
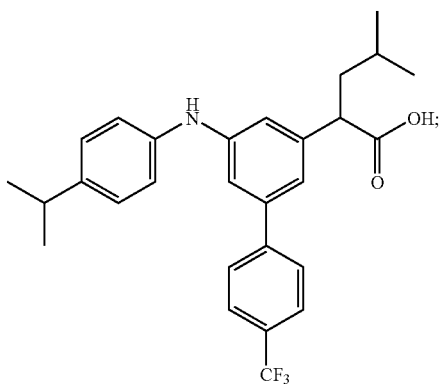
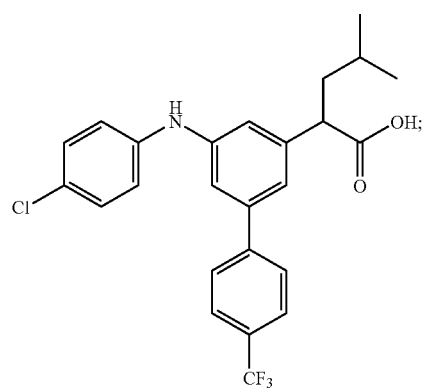
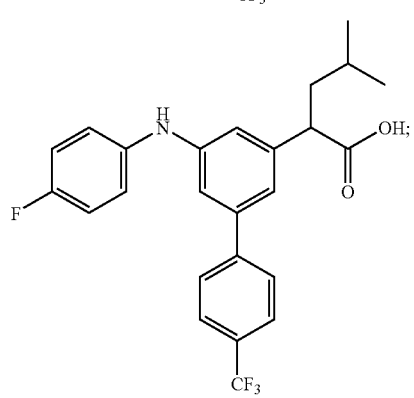
-continued
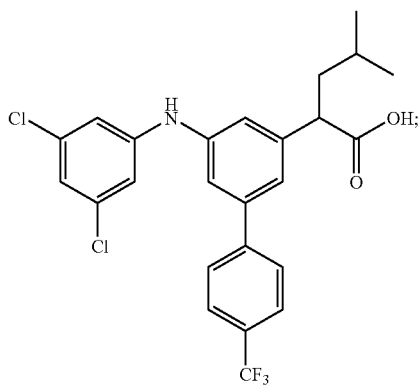
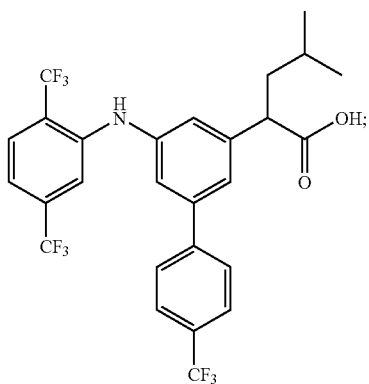
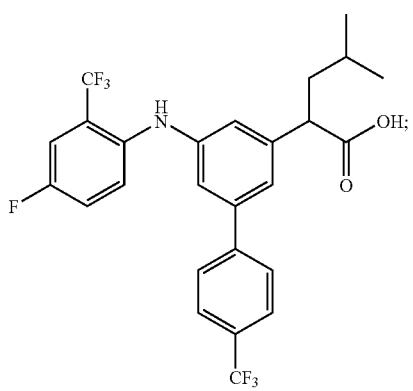
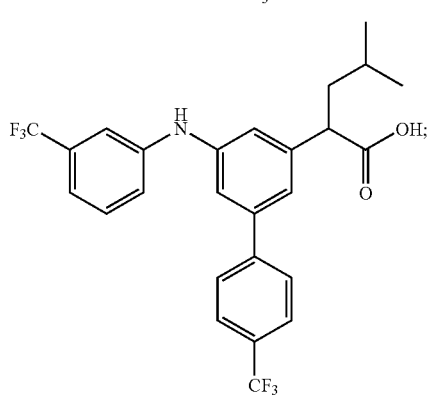

-continued
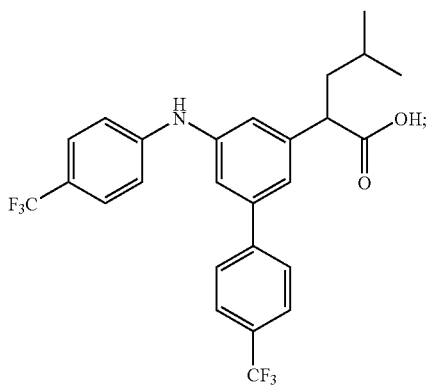
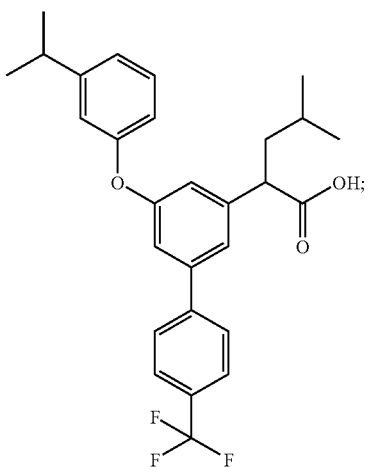

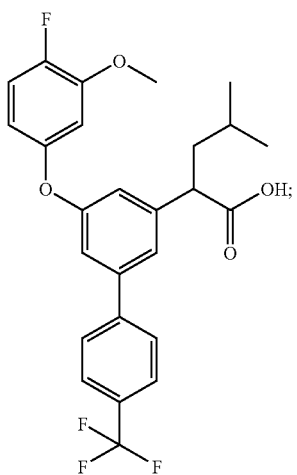
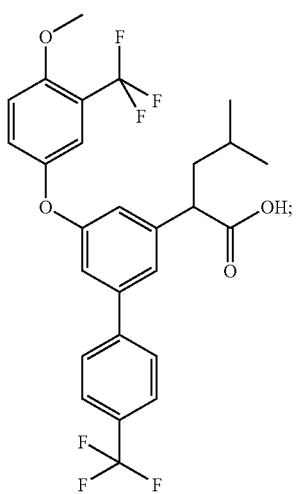
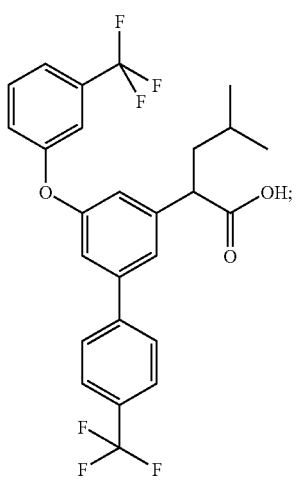
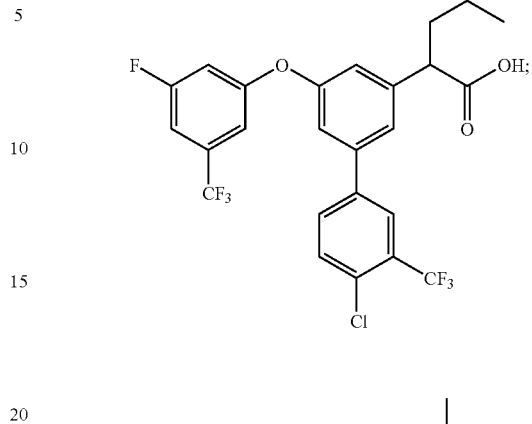
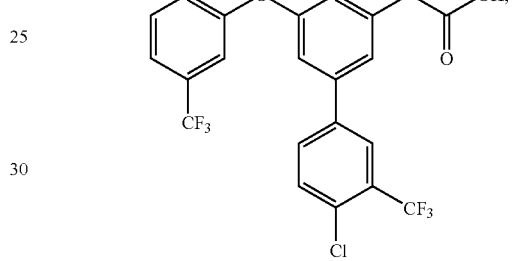
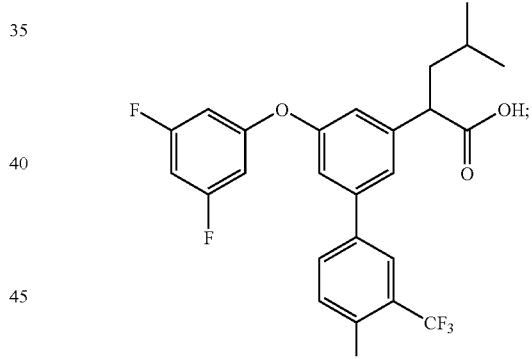
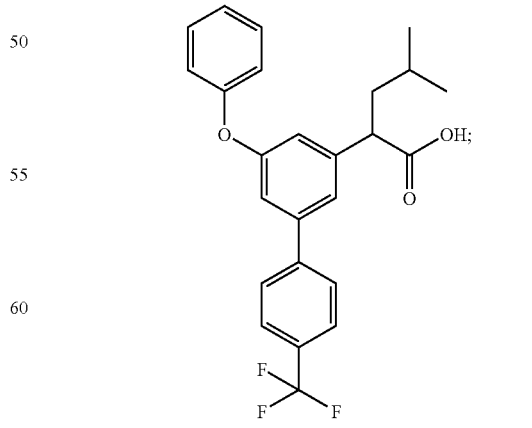

-continued
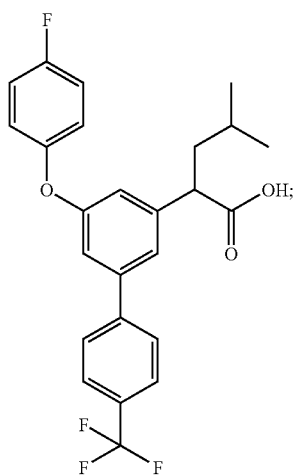
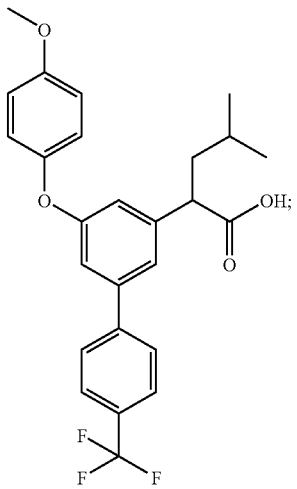
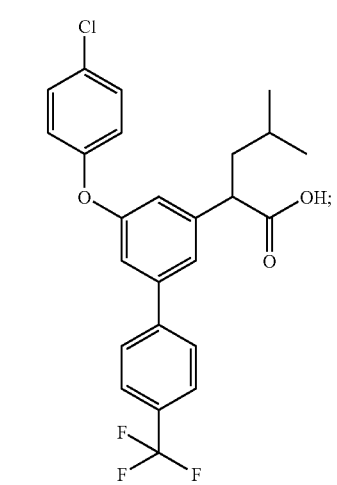
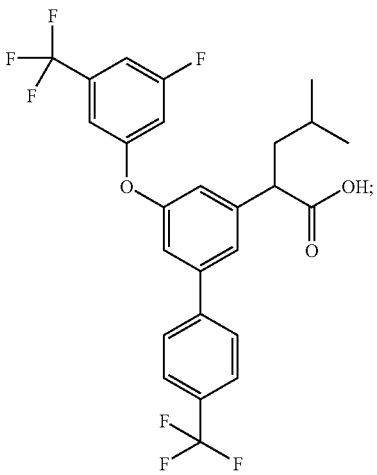

-continued
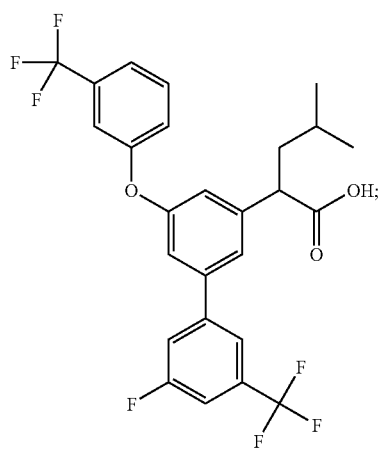
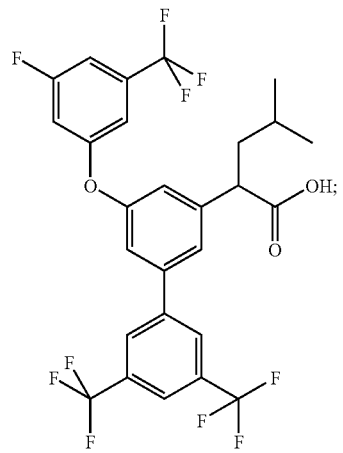

-continued
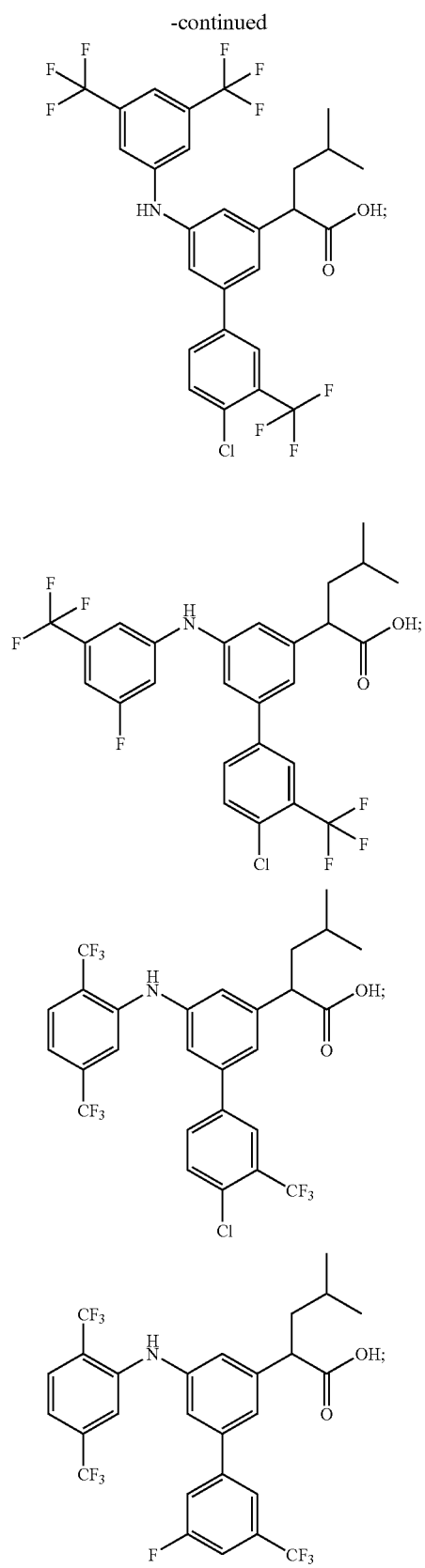
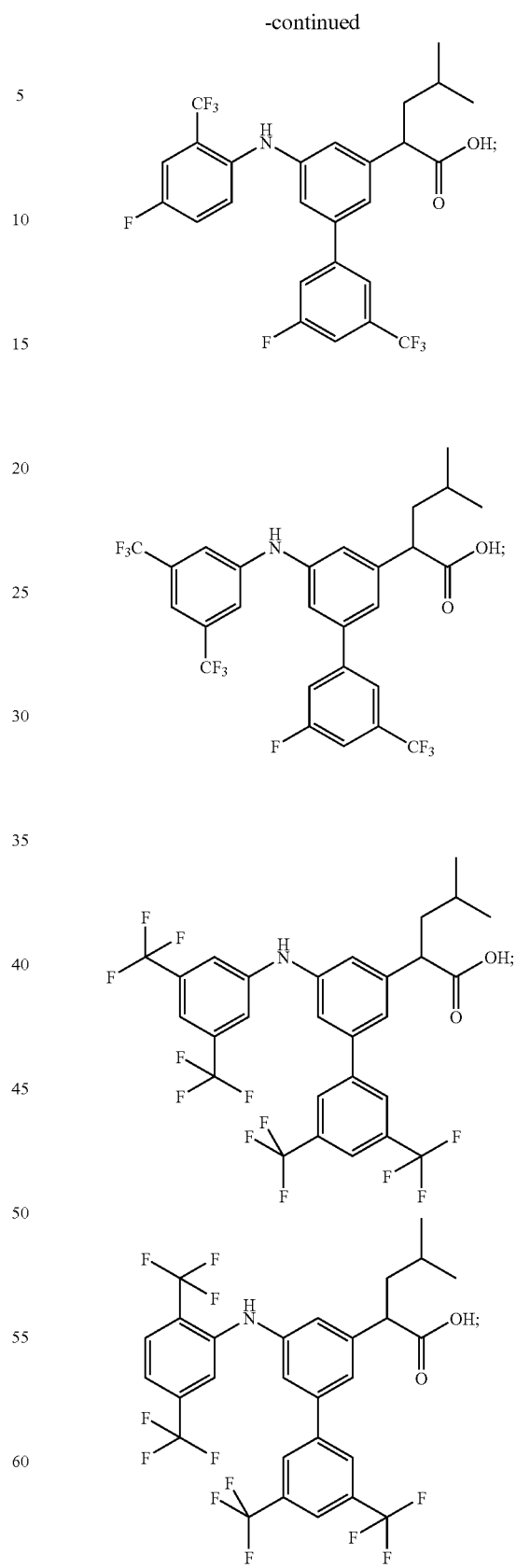

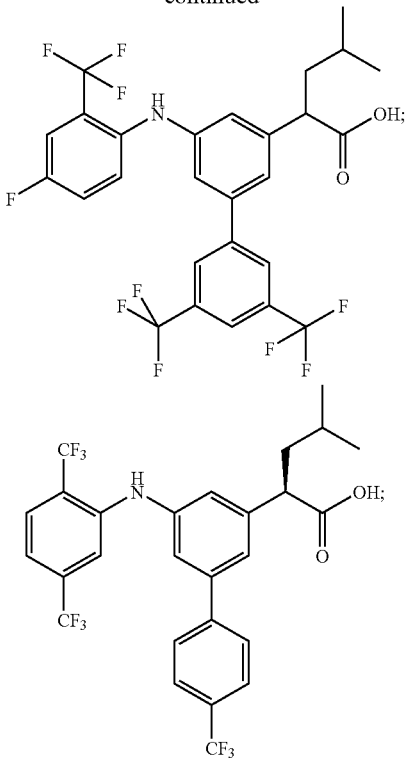

and solvates, hydrates, esters, and pharmaceutically acceptable salts thereof.

7. A pharmaceutical composition comprising a compound according to any of claims 1 to 6 in admixture with an inert carrier.

8. A process for the preparation of a compound according to any of claims 1 to 6 with A being O, comprising the following steps:
   a) treating a dihalidefluorobenzene compound, preferably dibromofluorobenzene, with a benzyl alcohol in the presence of an alkali metal hydride;
   b) treating the product with a suitable malonic ester derivative in the presence of an alkali metal hydride and a metal halide;
   c) treatment in an acidic solvent;
   d) coupling to a boronic acid derivative;
   e) removal of the benzyl ether protecting group;
   f) converting the resulting hydroxycompound to a triflate and coupling to a boronic acid;
   g) optionally alkylating the resulting compound;
   h) removal of the benzyl protecting group;
   i) converting the phenol to a biphenyl ether;
   j) conversion of the ester to the acid.
   k) optional resolution of racemic mixture into enantiomers.

9. A process for the preparation of a compound according to any of claims 1 to 6 with A being S, comprising the steps as laid out in claim 8, with the exception that the alkali metal hydride is replaced by a suitable base and the benzyl alcohol is replaced by an aryl thiol.

10. A process for the preparation of a compound according to any of claims 1 to 6 with A being NH, comprising the following steps:
    a) treating a dihalidefluorobenzene compound, preferably dibromofluorobenzene, with a benzyl alcohol in the presence of an alkali metal hydride;
    b) treating the product with a suitable malonic ester derivative in the presence of an alkali metal hydride and a metal halide;
    c) treatment in an acidic solvent;
    d) coupling to an aniline
    e) removal of the benzyl ether protecting group;
    f) converting the resulting hydroxycompound to a triflate and coupling to a boronic acid;
    g) optionally alkylating the resulting product;
    h) conversion of the ester to the acid.
    i) optional resolution of racemic mixture into enantiomers.

11. Method for the preparation of a medicament comprising the steps of:
    a) preparing a compound according to any of claims 1 to 6; and
    b) formulation of a medicament containing said compound.

12. A method of inhibiting γ-secretase, which method comprises administering to said mammal a therapeutically effective amount of a compound according to any of claims 1 to 6.

13. A method of treating in a mammal a disease associated with an elevated level of Aβ42-production by inhibiting γ-secretase, which method comprises administering to said mammal a therapeutically effective amount of a compound according to any of claims 1 to 6.

14. A method of treating Alzheimer's disease in a mammal inhibiting γ-secretase, which method comprises administering to said mammal a therapeutically effective amount of a compound according to any of claims 1 to 6.

15. A compound according to claim 1 as a base.

* * * * *